United States Patent
Copland, III et al.

(10) Patent No.: US 12,286,413 B2
(45) Date of Patent: Apr. 29, 2025

(54) COMPOUNDS AND METHODS FOR TREATING CANCER

(71) Applicant: Mayo Foundation for Medical Education and Research, Rochester, MN (US)

(72) Inventors: John A. Copland, III, Ponte Vedra Beach, FL (US); Han W. Tun, Jacksonville, FL (US); Thomas R. Caulfield, Jacksonville, FL (US); Christina Von Roemeling, Jacksonville, FL (US); Laura Ann Marlow, Jacksonville, FL (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 252 days.

(21) Appl. No.: 17/713,949

(22) Filed: Apr. 5, 2022

(65) Prior Publication Data
US 2022/0411389 A1    Dec. 29, 2022

Related U.S. Application Data

(63) Continuation of application No. 16/422,519, filed on May 24, 2019, now Pat. No. 11,325,892, which is a continuation of application No. 15/502,301, filed as application No. PCT/US2015/044278 on Aug. 7, 2015, now Pat. No. 10,301,273.

(60) Provisional application No. 62/034,429, filed on Aug. 7, 2014.

(51) Int. Cl.
| | |
|---|---|
| *C07D 295/192* | (2006.01) |
| *A61K 31/44* | (2006.01) |
| *A61K 31/495* | (2006.01) |
| *A61K 31/496* | (2006.01) |
| *A61K 45/06* | (2006.01) |
| *C07D 211/64* | (2006.01) |
| *C07D 211/66* | (2006.01) |
| *C07D 213/64* | (2006.01) |
| *C07D 213/75* | (2006.01) |

(52) U.S. Cl.
CPC .......... *C07D 295/192* (2013.01); *A61K 31/44* (2013.01); *A61K 31/495* (2013.01); *A61K 31/496* (2013.01); *A61K 45/06* (2013.01); *C07D 211/64* (2013.01); *C07D 211/66* (2013.01); *C07D 213/64* (2013.01); *C07D 213/75* (2013.01)

(58) Field of Classification Search
CPC .............. C07D 295/192; C07D 211/64; C07D 211/66; C07D 213/64; C07D 213/75; A61K 31/44; A61K 31/495; A61K 31/496; A61K 45/06
USPC ...................................... 514/253.12
See application file for complete search history.

(56) References Cited

U.S. PATENT DOCUMENTS

| | | | |
|---|---|---|---|
| 6,066,730 A | 5/2000 | Adams et al. | |
| 6,297,217 B1 | 10/2001 | Adams et al. | |
| 6,548,668 B2 | 4/2003 | Adams et al. | |
| 6,699,835 B2 | 3/2004 | Plamondon et al. | |
| 7,014,866 B2 | 3/2006 | Infeld et al. | |
| 7,109,323 B2 | 9/2006 | Plamondon et al. | |
| 7,531,526 B2 | 5/2009 | Adams et al. | |
| 7,547,698 B2 | 6/2009 | Kamboj et al. | |
| 7,592,343 B2 | 9/2009 | Kamboj et al. | |
| 7,687,456 B2 | 3/2010 | Zhou et al. | |
| 7,691,852 B2 | 4/2010 | Shenk et al. | |
| 7,767,677 B2 * | 8/2010 | Kamboj ............... | A61P 5/50 514/252.02 |
| 7,893,066 B2 | 2/2011 | Koltun et al. | |
| 7,944,263 B2 | 5/2011 | Suda | |
| 7,960,358 B2 | 6/2011 | Bhanot et al. | |
| 8,017,761 B2 | 9/2011 | McSwiggen et al. | |
| 8,026,360 B2 | 9/2011 | Kamboj et al. | |
| 8,030,488 B2 | 10/2011 | Sviridov et al. | |
| 8,071,603 B2 | 12/2011 | Kamboj et al. | |
| 8,080,545 B2 | 12/2011 | Shenk et al. | |
| 8,080,576 B2 | 12/2011 | Shenk et al. | |
| 8,088,741 B2 | 1/2012 | Smyth et al. | |
| 8,148,378 B2 | 4/2012 | Gschwend et al. | |
| 8,258,160 B2 | 9/2012 | Dales et al. | |
| 8,314,138 B2 | 11/2012 | Dales et al. | |
| 8,357,683 B2 | 1/2013 | Shenk et al. | |
| 8,431,571 B2 | 4/2013 | Shenk et al. | |

(Continued)

FOREIGN PATENT DOCUMENTS

| | | |
|---|---|---|
| EP | 2266569 | 12/2010 |
| EP | 2269610 | 1/2011 |

(Continued)

OTHER PUBLICATIONS

Abramson, "The lipogenesis pathway as a cancer target," J. Med. Chem., 54(16):5615-38, Aug. 2011.

(Continued)

*Primary Examiner* — Yevgeny Valenrod
(74) *Attorney, Agent, or Firm* — Fish & Richardson P.C.

(57) ABSTRACT

This document provides compounds, compositions, and methods for treating cancers including renal cancer (e.g., renal cell carcinoma) as well as ovarian, breast, prostate, colon, pancreatic, bladder, liver, lung, and thyroid cancers and melanoma. For example, compounds, compositions, and methods for using one or more inhibitors of SCD1 to treat renal cell carcinoma (e.g., clear cell renal cell carcinoma (ccRCC)), thyroid cancer, or liver cancer; or to increase the efficacy of treatment for the same.

20 Claims, 27 Drawing Sheets
Specification includes a Sequence Listing.

(56) References Cited

U.S. PATENT DOCUMENTS

| | | |
|---|---|---|
| 9,233,102 B2 | 1/2016 | Copland, III et al. |
| 9,358,250 B2 | 6/2016 | Ashkenazi |
| 10,160,972 B2 | 12/2018 | Copland, III et al. |
| 10,301,273 B2 | 5/2019 | Copland, III et al. |
| 11,243,207 B2 | 2/2022 | Copland, III et al. |
| 11,325,892 B2 | 5/2022 | Copland, III et al. |
| 11,596,629 B2 | 3/2023 | Copland, III et al. |
| 11,833,144 B2 * | 12/2023 | Copland, III .......... A61P 37/06 |
| 2003/0064950 A1 | 4/2003 | Ntambi et al. |
| 2005/0130193 A1 | 6/2005 | Luxon et al. |
| 2006/0079502 A1 | 4/2006 | Lang |
| 2006/0094744 A1 | 5/2006 | Maryanoff et al. |
| 2008/0182851 A1 | 7/2008 | Thomas et al. |
| 2010/0081666 A1 | 4/2010 | Coughlin et al. |
| 2010/0160323 A1 | 6/2010 | Bischoff et al. |
| 2010/0249192 A1 | 9/2010 | Li et al. |
| 2011/0021532 A1 | 1/2011 | Powell et al. |
| 2011/0046134 A1 | 2/2011 | Bischoff et al. |
| 2011/0166152 A1 | 7/2011 | Leclerc et al. |
| 2011/0183958 A1 | 7/2011 | Powell et al. |
| 2011/0213136 A1 | 9/2011 | Bhanot et al. |
| 2011/0301143 A1 | 12/2011 | Isabel et al. |
| 2012/0010186 A1 | 1/2012 | Lachance et al. |
| 2012/0219623 A1 | 8/2012 | Meinicke |
| 2012/0277280 A1 | 11/2012 | Li et al. |
| 2013/0096181 A1 | 4/2013 | Ashkenazi et al. |
| 2015/0045418 A1 | 2/2015 | Copland, III et al. |
| 2015/0218274 A1 | 8/2015 | Sabatos-Peyton et al. |
| 2016/0067336 A1 | 3/2016 | Fand et al. |
| 2016/0152986 A1 | 6/2016 | Copland, III et al. |
| 2017/0015654 A1 | 1/2017 | Imamura et al. |
| 2017/0362595 A1 | 12/2017 | Copland, III et al. |
| 2019/0127805 A1 | 5/2019 | El-Helali et al. |
| 2019/0302121 A1 | 10/2019 | Copland, III |
| 2019/0345123 A1 | 11/2019 | Copland, III |
| 2020/0061055 A1 | 2/2020 | Von Roemeling |
| 2022/0062259 A1 | 3/2022 | Copland, III et al. |
| 2023/0201192 A1 | 6/2023 | Copland, III et al. |
| 2023/0310419 A1 | 10/2023 | Copland, III et al. |

FOREIGN PATENT DOCUMENTS

| | | |
|---|---|---|
| WO | WO 2003/006009 | 1/2003 |
| WO | WO 2006/015621 | 2/2006 |
| WO | WO 2006/034312 | 3/2006 |
| WO | WO 2006/034338 | 3/2006 |
| WO | WO 2006/034440 | 3/2006 |
| WO | WO 2006/034441 | 3/2006 |
| WO | WO 2006/101521 | 9/2006 |
| WO | WO 2006/121250 | 11/2006 |
| WO | WO 2006/130986 | 12/2006 |
| WO | WO 2007/005763 | 1/2007 |
| WO | WO 2007/009236 | 1/2007 |
| WO | WO 2007/056846 | 5/2007 |
| WO | WO 2007/071023 | 6/2007 |
| WO | WO 2007/130075 | 11/2007 |
| WO | WO 2007/134457 | 11/2007 |
| WO | WO 2007/143823 | 12/2007 |
| WO | WO 2007/143824 | 12/2007 |
| WO | WO 2008/017161 | 2/2008 |
| WO | WO 2008/020435 | 2/2008 |
| WO | WO 2008/046226 | 4/2008 |
| WO | WO 2008/064474 | 6/2008 |
| WO | WO 2008/074824 | 6/2008 |
| WO | WO 2008/074832 | 6/2008 |
| WO | WO 2008/074834 | 6/2008 |
| WO | WO 2008/089580 | 7/2008 |
| WO | WO 2008/120759 | 10/2008 |
| WO | WO 2009/019566 | 2/2009 |
| WO | WO 2009/020448 | 2/2009 |
| WO | WO 2009/051581 | 4/2009 |
| WO | WO 2009/060053 | 5/2009 |
| WO | WO 2009/060054 | 5/2009 |
| WO | WO 2009/106991 | 9/2009 |
| WO | WO 2009/147125 | 12/2009 |
| WO | WO 2009/154737 | 12/2009 |
| WO | WO 2010/025553 | 3/2010 |
| WO | WO 2010/036357 | 4/2010 |
| WO | WO 2010/079197 | 7/2010 |
| WO | WO 2010/086411 | 8/2010 |
| WO | WO 2010/092163 | 8/2010 |
| WO | WO 2010/094120 | 8/2010 |
| WO | WO 2010/149640 | 12/2010 |
| WO | WO 2011/011872 | 2/2011 |
| WO | WO 2011/030312 | 3/2011 |
| WO | WO 2011/064352 | 6/2011 |
| WO | WO 2011/123502 | 10/2011 |
| WO | WO 2012/151451 | 11/2012 |
| WO | WO 2013/134546 | 9/2013 |
| WO | WO 2014/153150 | 9/2014 |
| WO | WO 2016/022955 | 2/2016 |
| WO | WO 2016/141299 | 9/2016 |
| WO | WO 2016/183326 | 11/2016 |
| WO | WO 2018/160717 | 9/2018 |

OTHER PUBLICATIONS

Ackerman and Simon, "Hypoxia, lipids, and cancer: surviving the harsh tumor microenvironment, "Trends Cell Biol., 24(8):472-8, Aug. 2014.

Ahn, "An evaluation of phase I cancer clinical trial designs," Stat. Med., 17(14):1537-49, Jul. 1998.

Angelucci et al., "Stearoyl-CoA desaturase 1 and paracrine diffusible signals have a major role in the promotion of breast cancer cell migration induced by cancer-associated fibroblasts," Br. J. Cancer. 112(10):1675-86, Apr. 2015.

Aparicio et al., "Examining the utility of patient-derived xenograft mouse models," Nat. Rev. Cancer, 15(5):311-6, Apr. 2015.

Baenke et al., "Hooked on fat: the role of lipid synthesis in cancer metabolism and tumour development," Dis. Model Mech., 6(6):1353-63, Nov. 2013.

Bankaitis, "Unsaturated fatty acid-induced non-canonical autophagy: unusual? or unappreciated?" EMBO J., 34(8);978-80, Apr. 2015.

Bansal et al., "Stearoyl-CoA desaturase plays an important role in proliferation and chemoresistance in human hepatocellular carcinoma," J. Surg. Res., 186(1):29-38, Jan. 2014.

Beloribi-Djefaflia et al., "Lipid metabolic reprogramming in cancer cells," Oncogenesis, 5(1):e189, Jan. 2016.

Ben-David et al., "Selective Elimination of Human Pluripotent Stem Cells by an Oleate Synthesis Inhibitor Discovered in a High-Throughput Screen," Cell Stem Cell, 12(2):167-79, Feb. 2013.

Berge et al., "Pharmaceutical Salts", J Pharm Sci., 66(1):1-19, Jan. 1977.

Böhm et al., "Scaffold hopping," Drug Discov Today: Technologies., 1(3):217-224, 2004.

Brown "Bioisosterism in Medicinal Chemistry", 2012, Wiley-VCH Verlag GmbH & Co. KGaA, pp. 1-14 (Year: 2012).

Brown and Rudel, "Stearoyl-coenzyme A desaturase 1 inhibition and the metabolic syndrome: considerations for future drug discovery," Curr. Opin. Lipidol., 21(3):192-7, Jun. 2010.

Cao et al., "Sphereforming cell subpopulations with cancer stem cell properties in human hepatoma cell lines," BMC Gastroenterol., 11(1):71, Jun. 2011.

Cassidy et al., "Maintaining Tumor Heterogeneity in Patient-Derived Tumor Xenografts," Cancer Res., 75(15):2963-8, Aug. 2015.

Caulfield et al., "Motion of transfer RNA from the A/T state into the A-site using docking and simulations," Proteins., 80(11):2489-2500, Nov. 2012.

Chajès et al., "Association between Serum trans-Monounsaturated Fatty Acids and Breast Cancer Risk in the E3N-EPIC Study," Am. J. Epidemiol., 167(11):1312-20, Apr. 2008.

Chajès et al., "Riboli E. Fatty-acid composition in serum phospholipids and risk of breast cancer: An incident case-control study in Sweden," Intern. J. Cancer, 83(5):585-90, Nov. 1999.

Chang et al., "KGF induces lipogenic genes through a PI3K and JNK/SREBP-1 pathway in H292 cells," J. Lipid Res., 46(12):2624-35, Dec. 2005.

(56) References Cited

OTHER PUBLICATIONS

Chen et al., "Targeting oncogenic Myc as a strategy for cancer treatment," Signal transduction and targeted therapy, 3(1):1-7, Feb. 2018.
Chou and Talalay, "Quantitative analysis of dose-effect relationships: the combined effects of multiple drugs or enzyme inhibitors," Adv. Enzyme Regul., 22:27-55, 1984.
Chou et al., "Analysis of combined drug effects: a new look at a very old problem," Trends in Pharmacological Sciences., 4(11):450-454, 1983.
Chou et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., 86(20):1517-24, Oct. 1994.
Chou, "Drug Combination Studies and Their Synergy Quantification Using the Chou-Talalay Method," Cancer Res., 70(2):440-6, Jan. 2010.
Chow et al., "The Enhanced Metastatic Potential of Hepatocellular Carcinoma (HCC) Cells with Sorafenib Resistance," PLoS One, 8(11):e78675, Nov. 2013.
Conway et al., "Xenome—a tool for classifying reads from xenograft samples," Bioinformatics, 28(12):i172-8, Jun. 2012.
Cooper et al., "Current status of biomarker discovery in human clear cell renal cell carcinoma," J. Mol. Biomark Diagn., S2:1-10, 2012.
Copland et al., "Novel high-affinity PPARgamma agonist alone and in combination with paclitaxel inhibits human anaplastic thyroid carcinoma tumor growth via p21WAF1/CIP1," Oncogene., 25(16):2304-2317, Apr. 13, 2006.
Costello B. Navitoclax and Sorafenib Tosylate in Treating Patients with Relapsed or Refractory Solid Tumors. [http://www.cancer.gov/about-cancer/treatment/clinicaltrials/search/view?cdrid=761522&version=HealthProfessional&protocolsearchid=8215330 ]; 2014 [NCT02143401].
Currie et al., "Cellular Fatty Acid Metabolism and Cancer," Cell Metabolism, 18(2):153-61, Aug. 2013.
Database accession No. 1390035-79-6, [online] "1-Pi peraz i necarboxami de, 4-benzoyl-N-[2-[[(1,1 dimethylethyl)ami no] carbonyl]phenyl]-," Aug. 12, 2012, Abstract Only, 1 page.
Demoulin et al., "Platelet-derived Growth Factor Stimulates Membrane Lipid Synthesis Through Activation of Phosphatidylinositol 3-Kinase and Sterol Regulatory Element-binding Proteins," J. Biol. Chem., 279(34):35392-402, Aug. 2004.
Dholaria et al., "Emerging therapeutic agents for lung cancer," Journal of hematology & oncology, 9(1):138, Dec. 2016.
Du et al., "FGFR3 Stimulates Stearoyl CoA Desaturase 1 Activity to Promote Bladder Tumor Growth," Cancer Res., 72(22):5843-55, Nov. 2012.
Du Manoir et al., "Breast tumor PDXs are genetically plastic and correspond to a subset of aggressive cancers prone to relapse," Mol. Oncol., 8(2):431-43, Mar. 2014.
Einarsdottir et al., "Melanoma patient-derived xenografts accurately model the disease and develop fast enough to guide treatment decisions," Oncotarget, 5(20):9609-18, Oct. 2014.
Extended European Search Report in International Application No. EP15830331.3, dated Mar. 9, 2018, 11 pages.
Falvella et al., "Stearoyl-CoA desaturase 1 (Scd1) gene overexpression is associated with genetic predisposition to hepatocarcinogenesis in mice and rats," Carcinogenesis, 23(11):1933-6, Nov. 2002.
Friesner et al., "Extra Precision Glide: Docking and Scoring Incorporating a Model of Hydrophobic Enclosure for Protein-Ligand Complexes," Journal of medicinal chemistry., 49(21):6177-6196, Oct. 19, 2006.
Fritz et al., "Abrogation of De novo Lipogenesis by Stearoyl-CoA Desaturase 1 Inhibition Interferes with Oncogenic Signaling and Blocks Prostate Cancer Progression in Mice," Mol. Cancer Therap., 9(6):1740-54, Jun. 2010.
Fu et al., "Discovery of new non-steroidal FXR ligands via a virtual screening workflow based on Phase shape and induced fit docking," Bioorg Med Chem Lett., 22(22):6848-6853, Nov. 15, 2012.

Fucikovaet al., "Prognostic and predictive value of DAMPs and DAMP-associated processes in cancer," Front Immunol., 6:402, Aug. 2015.
Gao et al., "High-throughput screening using patient-derived tumor xenografts to predict clinical trial drug response," Nat. Med., 21(11):1318-25, Oct. 2015.
GenBank® Accession No. AF097514.1 (GI No. 4808600), "*Homo sapiens* stearoyl-CoA desaturase (SCD) mRNA, complete cds," May 19, 1999, 2 pages.
GenBank® Accession No. O00767 (GI No. 21431730), "Acyl-CoA desaturase," Jul. 15, 1998, 11 pages.
Goldberg and Drake, "LAG-3 in Cancer Immunotherapy," Curr. Top Microbiol. Immunol., 344:269-78, Nov. 2010.
Goodman et al., "Some practical improvements in the continual reassessment method for phase I studies," Stat. Med., 14(11):1149-61, Jun. 1995.
Gu et al., Autophagyrelated prognostic signature for breast cancer. Mol. Carcinogenesis, 55(3):292-9, Mar. 2016.
Guillou et al, "The key roles of elongases and desaturases in mammalian fatty acid metabolism: Insights from transgenic mice," Prog Lipid Res., 49(2):186-199, Apr. 2010.
Guo et al., "EGFR Signaling Through an Akt-SREBP-1-Dependent, Rapamycin-Resistant Pathway Sensitizes Glioblastomas to Antilipogenic Therapy," Sci. Signal., 2(101):ra82, Dec. 2009.
Guo et al., "Therapeutic cancer vaccines: past, present, and future," Adv. Cancer Res., 119:421-75, Jan. 2013.
Halgren., "Identifying and characterizing binding sites and assessing druggability," J Chem Inf Model., 49(2):377-389, Feb. 2009.
Halgren., "New method for fast and accurate binding-site identification and analysis," Chem Biol Dru Des., 69(2):146-148, Feb. 2007.
Hanahan and Weinberg, "Hallmarks of cancer: the next generation," Cell, 144(5):646-74, Mar. 2011.
Heitjan, "Biology, Models, and the Analysis of Tumor Xenograft Experiments," Clin. Cancer Res., 17(5):949-52, Jan. 2011.
Herr et al., "Drop-off during ribosome hopping," J Mol Biol., 311(3):445-452, Aug. 17, 2001.
Hess et al., "Inhibition of StearoylCoA Desaturase Activity Blocks Cell Cycle Progression and Induces Programmed Cell Death in Lung Cancer Cells," PLoS One, 5(6):e11394, Jun. 2010.
Hetz et al., "Targeting the unfolded protein response in disease," Nat Rev Drug Discov., 12(9):703-719, Sep. 2013.
Hidalgo et al., "Patient-Derived Xenograft Models: An Emerging Platform for Translational Cancer Research," Cancer Disc., 4(9):998-1013, Sep. 2014.
Hockla et al., "PRSS3/Mesotrypsin Is a Therapeutic Target for Metastatic Prostate Cancer," Mol. Cancer Res., 10(12):1555-66, Dec. 2012.
Holland et al., "Wnt signaling in stem and cancer stem cells," Curr. Opin. Cell Biol., 25(2):254-64., Apr. 2013.
Huang et al., "SCD1 negatively regulates autophagy-induced cell death in human hepatocellular carcinoma through inactivation of the AMPK signaling pathway," Cancer Lett.., 358(2):180-90, Mar. 2015.
Huard et al., "Cellular expression and tissue distribution of the human LAG-3-encoded protein, an MHC class II ligand," Immunogenetics, 39(3):213-217, Jan. 1994.
Ide et al., "Human breast cancer tissues contain abundant phosphatidylcholine (36: 1) with high stearoyl-CoA desaturase-1 expression," PLoS One, 8(4):e61204, 2013.
Igal, "Stearoyl-CoA desaturase-1: a novel key player in the mechanisms of cell proliferation, programmed cell death and transformation to cancer," Carcinogenesis, 31(9):1509-15, Jul. 2010.
International Preliminary Report on Patentability in International Application No. PCT/US2015/044278, Issued Feb. 7, 2017, 7 pages.
International Search Report and the Written Opinion in International Application No. PCT/US2015/044278, mailed Jan. 11, 2016, 14 pages.
Invitation to Pay Additional Fees in International Application No. PCT/US2015/044278, dated Oct. 26, 2015, 2 pages.

(56) References Cited

OTHER PUBLICATIONS

Izuishi et al., "Remarkable tolerance of tumor cells to nutrient deprivation: possible new biochemical target for cancer therapy," Cancer Res., 60(21):6201-7, Nov. 2000.
Janssens et al., "Emerging functions of the unfolded protein response in immunity," Nat. Immunol., 15(10):910-9, Oct. 2014.
Jemal et al., "Global cancer statistics," CA Cancer J. Clin., 61(2):69-90, Feb. 2011.
Jianli Wang, Scott Saffold, Xuetao Cao, John Krauss, Wei Chen, Eliciting T Cell Immunity Against Poorly Immunogenic Tumors by Immunization with Dendritic Cell-Tumor Fusion Vaccines, The Journal of Immunology, Nov. 15, 1998, 161 (10) 5516-5524 (Year: 1998).
Jorgensen et al., "The OPLS [optimized potentials for liquid simulations] potential functions for proteins, energy minimizations for crystals of cyclic peptides and crambin," J Am Chern Soc., 110(6):1657-1666, Mar. 1, 1988.
Kalari et al., "MAP-RSeq: Mayo Analysis Pipeline for RNA sequencing," BMC Bioinformatics, 15(1):1-11, Jun. 2014.
Kalid et al., "Consensus Induced Fit Docking (cIFD): methodology, validation, and application to the discovery of novel Crm1 inhibitors," J Comput Aided Mol Des., 26(11):1217-1228, Nov. 2012.
Kim et al., "Cell death and endoplasmic reticulum stress: disease relevance and therapeutic opportunities," Nat Rev Drug Discov., 7(12):1013-1030, Dec. 2008.
Kim et al., "Stearoyl CoA desaturase (SCD) facilitates proliferation of prostate cancer cells through enhancement of androgen receptor transactivation," Mol. Cells, 31(4):371-7, Apr. 2011.
Koltun et al., "Novel, potent, selective, and metabolically stable stearoyl-CoA desaturase (SCD) inhibitors," Bioorganic Medicinal Chem Lett., 19(7):2048-2052, Apr. 1, 2009.
Koltun et al., "Orally bioavailable, liver-selective stearoyl-CoA desaturase (SCD) inhibitors," Bioorg. Med. Chem. Letters, Apr. 8, 2009, 19(11):3050-3053.
Koltun et al., "Potent, orally bioavailable, liver-selective stearoyl-CoA desaturase (SCD) inhibitors," Bioorg. Med. Chem. Letters, Jun. 13, 2009, 19(15):4070-4074.
Krieger et al., "Assignment of protonation states in proteins and ligands: combining pKa prediction with hydrogen bonding network optimization.," Methods Mol Biol., 819:405-421, 2012.
Krieger et al., "Improving physical realism, stereochemistry, and side-chain accuracy in homology modeling: Four approaches that performed well in CASP8," Proteins., 77(Suppl S9):114-122, 2009.
Kuhajda et al., "Fatty acid synthesis: a potential selective target for antineoplastic therapy," Proc. Natl. Acad. Sci. USA, 91(14):6379-83, 1994.
Kupershmidt et al., Ontology-based meta-analysis of global collections of high-throughput public data, PLoS One., 5(9):e13066, 13 pages Sep. 2010.
Le DT et al., PD-1 Blockade in Tumors with Mismatch-Repair Deficiency. N Engl J Med. Jun. 25, 2015;372(26):2509-20. (Year: 2015).
Lee et al., "Nutrient-sensing nuclear receptors coordinate autophagy," Nature, 516(7529):112-5, Nov. 2014.
Lee et al., Patient-Derived Xenografts from Non-Small Cell Lung Cancer Brain Metastases Are Valuable Translational Platforms for the Development of Personalized Targeted Therapy. Clin. Cancer Res., 21(5):1172-82, Mar. 2015.
Leger et al., "Synthesis and biological activity of a potent and orally bioavailable SCD inhibitor (MF-438)," Bioorg Med Chem Lett., 20(2):499-502, Jan. 15, 2010.
Leung and Kim, "Stearoyl Co-A Desaturase 1 as a ccRCC Therapeutic Target: Death by Stress," Clin. Cancer Res., 19(12):1-3, May 2013.
Li et al., "Endocrine-Therapy-Resistant ESR1 Variants Revealed by Genomic Characterization of Breast-Cancer-Derived Xenografts," Cell Reports, 4(6):1116-30, Sep. 2013.
Li et al., "SCD1 expression is dispensable for hepatocarcinogenesis induced by AKT and ras oncogenes in mice," Plos one., 8(9):e75104, Sep. 19, 2013, 12 pages.
Li et al., "Targeted hepatocellular carcinoma proapoptotic BikDD gene therapy," Oncogene, 30(15):1773-83, 2011.
Li et al., "Thiazole analog as stearoyl-CoA desaturase 1 inhibitor," Bioorg Med Chem Lett., 19(17):5214-5217, Epub Jul. 9, 2009.
Liang and Sha, "Modeling antitumor activity by using a non-linear mixed-effects model," Math. Biosci., 189(1):61-73, May 2004.
Liu et al., "Discovery of potent, selective, orally bioavailable stearoyl-CoA desaturase 1 inhibitors," J Med Chem., 50(13):3086-3100, Jun. 28, 2007.
Liu., "Stearoyl-CoA desaturase inhibitors: update on patented compounds," Expert Opin Ther Pat., 19(9):1169-1191, 2009.
Llovet et al., "Sorafenib in Advanced Hepatocellular Carcinoma," N. Engl. J. Med., 359(4):378-90, Jul. 2008.
Loving et al., "Energetic analysis of fragment docking and application to structure-based pharmacophore hypothesis generation," J computer-aided molecular design., 23(8):541-554, Aug. 2009.
Luyimbazi et al., "Rapamycin regulates stearoyl CoA desaturase 1 expression in breast cancer," Mol. Cancer Ther., 9(10):2770-84, Oct. 2010.
Ma et al., "Stearoyl-CoA desaturase regulates sorafenib resistance via modulation of ER stress-induced differentiation," Journal of hepatology, 67(5):979-90, Nov. 2017.
Ma, Kin Fai, et al. "Stearoyl-CoA Desaturase (SCD1) regulates liver tumor initiating cells through modulating ER stress," Cancer Res., 77(13):A4772, 2017. (Abstract).
Marlow et al., "Detailed molecular fingerprinting of four new anaplastic thyroid carcinoma cell lines and their use for verification of RhoB as a molecular therapeutic target," J Clin Endocrinol Metab., 95(12):5338-5347, 2010.
Marlow et al., "FoxO3a drives proliferation in anaplastic thyroid carcinoma through transcriptional regulation of cyclin A1: a paradigm shift that impacts current therapeutic strategies," J. Cell Sci., 125(18):4253-63, Sep. 2012.
Mason et al., "SCD1 Inhibition Causes Cancer Cell Death by Depleting Mono-Unsaturated Fatty Acids," PLoS One, 7(3):e33823, Mar. 2012.
Mauvoisin et al., "Decreasing stearoyl-CoA desaturase-1 expression inhibits β-catenin signaling in breast cancer cells," Cancer Sci., 104(1):36-42, Jan. 2013.
MedicineNet.com (http://www.medterms.com, 2004).
Mellman et al., "Cancer immunotherapy comes of age," Nature, 480(7378):480-9, Dec. 2011.
Menendez and Lupu, "Fatty acid synthase and the lipogenic phenotype in cancer pathogenesis," Nat. Rev. Cancer, 7(10):763-77, Oct. 2007.
Minville-Walz et al., "Inhibition of Stearoyl-CoA Desaturase 1 Expression Induces CHOP-Dependent Cell Death in Human Cancer Cells," PLoS One, 5(12):e14363, Dec. 2010.
Mohamadi et al., "Macromodel-an integrated software system for modeling organic and bioorganic molecules using molecular mechanics," J Comput Chem., 11(4):440-467, May 1990.
Monsma et al., "Using a rhabdomyosarcoma patient-derived xenograft to examine precision medicine approaches and model acquired resistance," Pediatr. Blood Cance, 61(9):1570-7, Mar. 2014.
Mounier et al., "Lipogenesis in cancer progression (review)," Int. J. Oncol., 45:485-92, May 2014.
Muir et al., "Proteomic and Lipidomic Signatures of Lipid Metabolism in NASH-Associated Hepatocellular Carcinoma," Cancer Res., 73(15):4722-31, Aug. 2013.
Nanda et al., Pembrolizumab in Patients With Advanced Triple-Negative Breast Cancer: Phase 1b Keynote-012 Study, Journal of Clinical Oncology 34, No. 21 (Jul. 20, 2016) 2460-2467. (Year: 2016).
Naugler et al., "Gender Disparity in Liver Cancer Due to Sex Differences in MyD88-Dependent IL-6 Production," Science, 317(5834):121-4, Jul. 2007.
Nelson et al., "Transcriptional changes associated with reduced spontaneous liver tumor incidence in mice chronically exposed to high dose arsenic," Toxicol., 266(1-3):6-15, Dec. 2009.
Nile and Hannoush, "Fatty acylation of Wnt proteins," Nat. Chem. Biol., 12(2):60-9, Jan. 2016.
Niso-Santano et al., "Unsaturated fatty acids induce non-canonical autophagy," EMBO J., 34(8):1025-41, Jan. 2015.

(56) References Cited

OTHER PUBLICATIONS

Noto et al., "Stearoyl-CoA desaturase-1 is a key factor for lung cancer-initiating cells," Cell Death Dis., 4(12):e947, Dec. 2013.
Oballa et al., "Development of a liver-targeted stearoyl-CoA desaturase (SCD) inhibitor (MK-8245) to establish a therapeutic window for the treatment of diabetes and dyslipidemia," J Med Chem., 54(14):5082-5096, Epub Jun. 28, 2011.
Oesterreich et al., "Using Mice to Treat (WO)men: Mining Genetic Changes in Patient Xenografts to Attack Breast Cancer," Cell Reports, 4(6):1061-2, Sep. 2013.
Okuda, "Epidemiology of primary liver cancer," Primary Liver Cancer in Japan, Tobe T (ed)., Chapter 1, pp. 3-15, 1992.
O'Quigley et al., "Continual reassessment method: a practical design for phase 1 clinical trials in cancer," Biometrics, 46(1):33-48, Mar. 1990.
Pala et al., "Erythrocyte Membrane Fatty Acids and Subsequent Breast Cancer: a Prospective Italian Study," J. Natl. Cancer Institute, 93(14):1088-95, Jul. 2001.
Pala et al., "Structure-Based Virtual Screening of MT2 Melatonin Receptor: Influence of Template Choice and Structural Refinement," J Chem Inf Model., 53(4):821-835, Mar. 29, 2013.
Panaretakis et al., "Mechanisms of pre-apoptotic calreticulin exposure in immunogenic cell death," EMBO J., 28(5):578-90, Mar. 2009.
Patani and LaVoie, "Bioisosterism: A Rational Approach in Drug Design," Chem. Rev., 96(8):3147-3176, 1996.
Paton and Ntambi, "Biochemical and physiological function of stearoyl-CoA desaturase," Am. J. Physiol. Endocrinol. Metab., 297(1):E28-37, Jul. 2009.
Petrek et al., "Fatty acid composition of adipose tissue, an indication of dietary fatty acids, and breast cancer prognosis," J. Clin. Oncol., 15(4):1377-84, Apr. 1997.
Petrova et al., "TTI-621 (SIRPαFc): a CD47-blocking innate immune checkpoint inhibitor with broad antitumor activity and minimal erythrocyte binding," Clinical Cancer Research, 23(4):1068-79, Feb. 2017.
Porstmann et al., "PKB//Akt induces transcription of enzymes involved in cholesterol and fatty acid biosynthesis via activation of SREBP," Oncogene, 24(43):6465-81, Jun. 2005.
Porstmann et al., "SREBP Activity Is Regulated by mTORC1 and Contributes to Akt-Dependent Cell Growth," Cell Metab., 8(3):224-36, Sep. 2008.
Powell et al., "2-Aryl benzimidazoles: human SCD1-specific stearoyl coenzyme-A desaturase inhibitors," Bioorg Med Chem Lett., 20(22):6366-6369, Nov. 15, 2010.
Powers, "Cell Growth Control: mTOR Takes on Fat," Mol. Cell, 31(6):775-6, Sep. 2008.
Pubchem, Substance Record for SID 144964572, AKOS008653309, Available Oct. 18, 2012, retrieved on Oct. 30, 2015, Retrieved from the Internet, URL: https://pubchem.ncbi.nlm.nih.gov/substance/144964572/version/1>, 6 pages.
Rathert et al., "Transcriptional plasticity promotes primary and acquired resistance to BET inhibition.," Nature, 525(7570):543-7, Sep. 2015.
Reya and Clevers, "Wnt signalling in stem cells and cancer," Nature, 434(7035):843-50, Apr. 2005.
Rodvold et al., "Immune modulation by ER stress and inflammation in the tumor microenvironment," Cancer Letters, 380(1):227-36, Sep. 2016.
Roemeling et al., "Aberrant lipid metabolism in anaplastic thyroid carcinoma reveals stearoyl CoA desaturase 1 as a novel therapeutic target," J. Clin. Endocrinol. Metab., 100(5): E697-E709, May 2015.
Roemeling et al., "Stearoyl-CoA Desaturase 1 Is a Novel Molecular Therapeutic Target for Clear Cell Renal Cell Carcinoma", Clin Canc Res., 19(9):2368-2380, Apr. 30, 2013.
Roongta et al., "Cancer cell dependence on unsaturated fatty acids implicates stearoyl-CoA desaturase as a target for cancer therapy," Mol Cancer Res., 9(11):1551-1561, Nov. 2011.
Rosenberg, "Raising the bar: the curative potential of human cancer immunotherapy," Sci. Transl. Med., 4(127):127ps8, Mar. 2012.
Ruddigkeit et al., "Visualization and virtual screening of the chemical universe database GDB-17," J Chem Inf Model., 53(1):56-65, Dec. 23, 2012.
Rysman et al., "De novo lipogenesis protects cancer cells from free radicals and chemotherapeutics by promoting membrane lipid saturation," Cancer Res., 70(20):8117-26, Oct. 2010.
Sampath and Ntambi, "The role of stearoyl-CoA desaturase in obesity, insulin resistance, and inflammation," Ann. N.Y Acad. Sci., 1243(1):47-53, Dec. 2011.
Sandor et al., "Virtual Fragment Docking by Glide: a Validation Study on 190 Protein-Fragment Complexes," J Chem Inf Model., 50(6):1165-1172, Jun. 2010.
Santos and Schulze, "Lipid metabolism in cancer," FEBS J., 279(15):2610-23, Aug. 2012.
Sastry et al., "Boosting Virtual Screening Enrichments with Data Fusion: Coalescing Hits from Two-Dimensional Fingerprints, Shape, and Docking," J Chem Inf Model., 53(7):1531-1542, 2013.
Sastry et al., "Rapid Shape-Based Ligand Alignment and Virtual Screening Method Based on Atom/Feature-Pair Similarities and Volume Overlap Scoring," J Chem Inf Model., 51(10):2455-2466, Sep. 15, 2011.
Scaglia et al., "Inhibition of StearoylCoA Desaturase-1 Inactivates Acetyl-CoA Carboxylase and Impairs Proliferation in Cancer Cells: Role of AMPK," PLoS One, 4(8):e6812, Aug. 2009.
Schlaepfer et al., "Progestin modulates the lipid profile and sensitivity of breast cancer cells to docetaxel," Mol. Cell. Endocrin., 363(1-2):111-21, Aug. 2012.
Schmittgen et al., "Analyzing real-time PCR data by the comparative C(T) method," Nat Protoc., 3(6): 1101-1108, 2008.
Seok et al., "Transcriptional regulation of autophagy by an FXR-CREB axis," Nature, 516(7529):108-11, Dec. 2014.
Siolas and Hannon, "Patient-Derived Tumor Xenografts: Transforming Clinical Samples into Mouse Models," Cancer Res., 73(17):5315-9, Sep. 2013.
Song et al., "Hypoxia-induced autophagy contributes to the chemoresistance of hepatocellular carcinoma cells," Autophagy, 5(8):1131-44, Nov. 2009.
Sorafenib Package Insert and Prescribing Information. 2010.
Sperandio et al., "MED-SuMoLig: A New Ligand-Based Screening Tool for Efficient Scaffold Hopping," J Chem Inf Model., 47(3):1097-1110, 2007.
Sun, "Classification of scaffold-hopping approaches," Drug discovery today., 17(7-8):310-324, Apr. 2012.
Tun et al., "Pathway signature of clear cell renal cell carcinoma," PLoS One, 5:e10696, May 2010.
Tusher et al., "Significance analysis of microarrays applied to the ionizing radiation response," Proc. Natl. Acad. Sci. USA, 98(9):5116-21, Apr. 2001.
Uto et al., "Discovery of novel SCD1 inhibitors: 5-Alkyl-4,5-dihydro-3H-spiro[1,5-benzoxazepine-2,4'-piperidine] analogs," Eur J Med Chem., 46(5):1892-1896, May 2011.
Uto et al., "Novel and potent inhibitors of stearoyl-CoA desaturase-1. Part I: Discovery of 3-(2-hydroxyethoxy)-4-methoxy-N-[5-(3-trifluoromethylbenzyl)thiazol-2-yl]benzamide," Bioorg. Med. Chem. Letters, Jun. 2, 2009, 19(15):4151-4158.
Uto et al., "Novel and potent inhibitors of stearoyl-CoA desaturase-1. Part II: Identification of 4-ethylamino-3-(2-hydroxyethoxy)-N-[5-(3-trifluoromethylbenzyl)thiazol-2-yl]benzamide and its biological evaluation," Bioorg. Med. Chem. Letters, Jun. 6, 2009, 19(15):4159-4166.
Uto et al., "Synthesis and evaluation of novel stearoyl-CoA desaturase 1 inhibitors: 1'-{6-[5-(pyridin-3-ylmethyl)-1,3,4-oxadiazol-2-yl]pyridazin-3-yl}-3,4-dihydrospiro[chromene-2,4'-piperidine] analogs," Eur J Med Chem., 45(11):4788-4796, Nov. 2010.
Vivoli et al., "Inhibition of Prohormone Convertases PC1/3 and PC2 by 2,5-Dideoxystreptamine Derivatives," Mol Pharmacol., 81(3):440-454, Mar. 2012.
Von Roemeling and Copland, "Targeting lipid metabolism for the treatment of anaplastic thyroid carcinoma," Expert Opin. Ther. Targets, 20(2):159-66, Sep. 2015.

(56) References Cited

OTHER PUBLICATIONS

Von Roemeling et al, "Aberrant Lipid Metabolism in Anaplastic Thyroid Carcinoma Reveals Stearoyl CoA Desaturase 1 as a Novel Therapeutic Target," J. Clin. Endocrinol. Metab., 100(5):E697-709, May 2015.

Von Roemeling et al., "Accelerated bottom-up drug design platform enables the discovery of novel stearoyl-CoA desaturase 1 inhibitors for cancer therapy," Oncotarget, Oct. 6, 2017, 9(1):3-20.

Von Roemeling et al., "Functional genomics identifies novel genes essential for clear cell renal cell carcinoma tumor cell proliferation and migration," Oncotarget, 5(14):5320-34, Jun. 2014.

Von Roemeling et al., "Neuronal Pentraxin 2 is a regulator of clear cell renal cell carcinoma malignancy through activation of the AMPA-selective glutamate receptor-4," Cancer Res., 75(17):4796-810, Jun. 2014.

Von Roemeling et al., "Stearoyl-CoA Desaturase 1 Is a Novel Molecular Therapeutic Target for Clear Cell Renal Cell Carcinoma," Clin. Cancer Res., 19(9):2368-80, May 2013.

Voss et al., "Discovery and pharmacological characterization of SAR707 as novel and selective small molecule inhibitor of stearoyl-CoA desaturase (SCD1)," Eur. J. Pharmacol.,. 707(1-3):140-6, May 2013.

Walter., "The unfolded protein response: from stress pathway to homeostatic regulation," Science., 334(6059):1081-1086, Nov. 25, 2011.

Wang and Shen et al., "Activation of ATF6 and an ATF6 DNA binding site by the endoplasmic reticulum stress response," J Biol Chem., 275(35):27013-27020, Sep. 1, 2000.

Watts et al., "A Conformational Search Method for Efficient Generation of Bioactive Conformers," J Chem Inf Model., 50(4):534-546, Apr. 26, 2010.

Whittle et al., "Patient-derived xenograft models of breast cancer and their predictive power," Breast Cancer Res., 17(1):17, Feb. 2015.

Woo et al., "Innate immune recognition of cancer," Annual review of immunology, 33:445-74, Mar. 2015.

Wu and Irizarry, "Preprocessing of oligonucleotide array data," Nat. Biotechnol., 22(6):656-8, Jun. 2004.

Wurz et al., "Novel cancer antigens for personalized immunotherapies: latest evidence and clinical potential," Ther. Adv. Med. Oncology, 8(1):4-31, Jan. 2016.

Xin et al., "Discovery of piperidine-aryl urea-based stearoyl-CoA desaturase 1 inhibitors," Bioorg Med Chem Lett., 18(15):4298-4302, Aug. 1, 2008.

Xu et al., "Endoplasmic reticulum stress: cell life and death decisions," J Clin Invest., 115(10):2656-2664, Oct. 2005.

Yahagi et al., "Co-ordinate activation of lipogenic enzymes in hepatocellular carcinoma," European Journal of Cancer, 41(9):1316-22, Jun. 2005.

Zhang and Du, "Dysregulated lipid metabolism in cancer," World journal of biological chemistry, 3(8):167, Aug. 2012.

Zhang et al., "Positive feedback loop and synergistic effects on promoting tumorgenesis between HIF-2α and SCD1 in clear cell renal cell carcinoma," Cancer Sci., 104:416-22, Apr. 2013.

Zhang et al., "Proteomic Study Reveals That Proteins Involved in Metabolic and Detoxification Pathways Are Highly Expressed in HER-2/neu-positive Breast Cancer," Mol. Cell. Proteomics, 4(11):1686-96, Nov. 2005.

Zhang et al., "Screening of kinase inhibitors targeting BRAF for regulating autophagy based on kinase pathways," Mol. Med. Rep., 9(1):83-90, Jan. 2014.

Zhao et al., "Bayesian Hierarchical Changepoint Methods in Modeling the Tumor Growth Profiles in Xenograft Experiments," Clin. Cancer Res., 17(5):1057-64, Mar. 2011.

Zhou., "Improving threading algorithms for remote homology modeling by combining fragment and template comparisons," Proteins., 78(9):2041-2048, Jul. 2010.

Zhou., "Protein structure prediction by Pro-Sp3-TASSER," Biophys J., 96(6):2119-2127, Mar. 2009.

Zhou., "Template-based protein structure modeling using TASSER(VMT)," Proteins., 80(22);352-361, Feb. 2012.

Zureik et al., "Fatty acid proportions in cholesterol esters and risk of premature death from cancer in middle aged French men," BMJ. 311(7015):1251-4, Aug. 1995.

U.S. Appl. No. 16/368,477, filed Mar. 28, 2019, John A. Copland III, Issued as U.S. Pat. No. 11,243,207.

U.S. Appl. No. 16/489,133, filed Aug. 27, 2019, Christina Von Roemeling, Published as US. Publication No. 2020/0061055.

Economopoulou P, Kotsantis I, Psyrri A. The promise of immunotherapy in head and neck squamous cell carcinoma: combinatorial immunotherapy approaches. ESMO Open. Feb. 13, 2017;1(6):e000122. doi: 10.1136/esmoopen-2016-000122. PMID:28848660; PMCID: PMC5548974. (Year: 2017).

Akkaya et al., "Second signals rescue B cells from activation-induced mitochondrial dysfunction and death," Nat. Immunology, Jul. 9, 2018 19(8):871-884.

Aljohani et al., "Insights into stearoyl-CoA desaturase-1 regulation of systemic metabolism," Trends Endocrinol. Metabolism, Dec. 2017, 28(12):831-842.

Alwarawrah et al., "Changes in Nutritional Status Impact Immune Cell Metabolism and Function," Front. Immunology, May 16, 2018, 9:1055, 14 pages.

Balmer et al., "Memory CD8(+) T Cells Require Increased Concentrations of Acetate Induced by Stress for Optimal Function," Immunity, Jun. 21, 2016, 44(6):1312-1324.

BioVision [online], "SCD1 Inhibitor," archived Sep. 24, 2013. Retrieved from the Internet: <URL: http://www.biovision.com/scd1-inhibitor-3983.html>, 1 page.

Boothby et al., "Metabolic Regulation of the Immune Humoral Response," Immunity, May 16, 2017, 46(5):743-755.

Caro-Maldonado et al., "Metabolic reprogramming is required for antibody production that is suppressed in anergic but exaggerated in chronically BAFF-exposed B cells," J. Immunology, Apr. 15, 2014, 192(8):3626-3636.

Carter et al., "The global burden of SLE: prevalence, health disparities and socioeconomic impact," Nat. Rev. Rheumatology, Oct. 2016, 12(10):605-620.

Chan, "Targeting the mammalian target of rapamycin (mTOR): a new approach to treating cancer," Br J Cancer., 91(8):1420-1424, Oct. 18, 2004.

Chiba et al., "Tumor-infiltrating DCs suppress nucleic acid-mediated innate immune responses through interactions between the receptor TIM-3 and the alarmin HMGB1," Nat. Immunol., Sep. 2012, 13(9):832-842.

Cho et al., "Glycolytic rate and lymphomagenesis depend on PARP14, an ADP ribosyltransferase of the B aggressive lymphoma (BAL) family," Proc. Natl. Acad. Sci. USA, Sep. 20, 2011, 108(38):15972-15977.

ClinicalTrials.gov [online], "A Study to Assess the Safety and Efficacy of MK8245 in Patients With Type 2 Diabetes Mellitus and Inadequate Glycemic Control (MK8245-005 AM2)," NCT 00846391, Feb. 17, 2009 [retrived on Aug. 31, 2015]. Retrieved from the Internet <URL: https://www.clinicaltrials.gov/ct2/show/NCT00846391?term=mk-8245&rank=1>, 3 pages.

ClinicalTrials.gov [online], "A Study to Evaluate the Safety, Tolerability, Pharmacokinetics and Pharmacodynamics of MK8245 (8245-004)(Completed)," NCT 00790556, Nov. 7, 2008 [retrieved on Aug. 31, 2015]. Retrieved from the Internet: <https://www.clinicaltrials.gov/ct2/show/NCT00790556?term=mk-8245&rank-3>, 3 pages.

ClinicalTrials.gov [online], "Pharmacokinetics and Pharmacodynamics of MK-8245 in Participants With Type 2 Diabetes (MK-8245-012)," NCT 00972322, Sep. 3, 2009 [retrieved on Aug. 31, 2015]. Retrieved from the Internet: <URL: https://www.clinicaltrials.gov/ct2/show/NCT00972322?term=mk-8245&rank=2>, 3 pages.

Cohen et al., "Role for stearoyl-CoA desaturase-1 in leptin-mediated weight loss," Science, 297(5579):240-243, Jul. 12, 2002.

Cooper et al., "Reexpression of tumor suppressor, sFRP1, leads to antitumor synergy of combined HDAC and methyltransferase inhibitors in chemoresistant cancers," Mol Cancer Ther., 11(10):2105-2115, Epub Jul. 23, 2012.

(56) References Cited

OTHER PUBLICATIONS

Crouch et al., "Frontline science: a reduction in DHA-derived mediators in male obesity contributes toward defects in select B cell subsets and circulating antibody," J. Leukoc. Biology, Aug. 2019, 106(2):241-257.
De Boer et al., "Transgenic mice with hematopoietic and lymphoid specific expression of Cre," Eur. J. Immunology, Feb. 2003, 33(2):314-325.
DiMauro et al., "Structural modifications of N-arylamide oxadiazoles: Identification of N-arylpiperidine oxadiazoles as potent and selective agonists of CB2," Bioorg Med Chem Lett., 18(15):4267-4274, Epub Jul. 13, 2008.
Dobrzyn et al., "Loss of stearoyl-CoA desaturase 1 inhibits fatty acid oxidation and increases glucose utilization in the heart," Am J Physiol Endocrinol Metab., 294(2):E357-E364, Epub Nov. 27, 2007.
Dobrzyn et al., "Stearoyl-CoA desaturase 1 deficiency increases fatty acid oxidation by activating AMP-activated protein kinase in liver," Proc. Natl. Acad. Sci. USA, Apr. 27, 2004, 101(17):6409-6414.
Dondeti et al., "Integrative genomic analyses of sporadic clear cell renal cell carcinoma define disease subtypes and potential new therapeutic targets," Cancer Res., 72(1):112-121, Epub Nov. 17, 2011.
Dufort et al., "Cutting edge: IL-4-mediated protection of primary B lymphocytes from apoptosis via Stat6-dependent regulation of glycolytic metabolism," J. Immunology, Oct. 15, 2007, 179(8):4953-4957.
Dufort et al., "Glucose-dependent de novo lipogenesis in B lymphocytes: a requirement for atp-citrate lyase in lipopolysaccharide-induced differentiation," J. Biol. Chemistry, Mar. 7, 2014, 289(10):7011-7024.
Economopoulou et al., "The promise of immunotherapy in head and neck squamous cell carcinoma," Annals of Oncology, Jul. 2016, 27:1675-1685.
Fagarasan et al., "Adaptive immune regulation in the gut: T cell-dependent and T cell-independent IgA synthesis," Annu. Rev. Immunology, Mar. 1, 2010, 28:243-273.
Falvella et al., "Stearoyl-CoA desaturase 1 (Scd1) gene overexpression is associated with genetic predisposition to hepatocarcinogenesis in mice and rats," Carcinogenesis, Nov. 2002, 23(11):1933-1936.
Fritsche, "Fatty acids as modulators of the immune response," Annu. Rev. Nutrition, Aug. 21, 2006, 26:45-73.
Fritsche, "The science of fatty acids and inflammation," Adv. Nutrition, May 15, 2015, 6(3):293S-301S.
Fritz et al., "Abrogation of de novo lipogenesis by stearoyl-CoA desaturase 1 inhibition interferes with oncogenic signaling and blocks prostate cancer progression in mice," Mol Cancer Ther., 9(6):1740-1754, Epub Jun. 8, 2010.
Gally et al., "FABP5 deficiency enhances susceptibility to H1N1 influenza A virus-induced lung inflammation," Am. J. Physiol. Lung Cell Mol. Physiology, Jul. 1, 2013, 305(1):L64-72.
GenBank Accession No. AB032261.1, "*Homo sapiens* Scd mRNA for stearoyl-CoA desaturase, complete cds," dated Apr. 4, 2000, 2 pages.
GenBank Accession No. AB208982.1, "*Homo sapiens* mRNA for stearoyl-CoA desaturase variant protein," dated Jul. 26, 2016, 2 pages.
GenBank Accession No. NC_000010.11, "*Homo sapiens* chromosome 10, GRCh38.p13 Primary Assembly," dated Jun. 14, 2019, 3 pages.
GenBank Accession No. NM_005063.5, "*Homo sapiens* stearoyl-CoA desaturase (SCD), mRNA," dated Jul. 31, 2019, 5 pages.
GenBank Accession No. XM_001723785.1, "Predicted: *Homo sapiens* similar to Putative uncharacterized protein PRO1933 (LOC100133188), mRNA," dated Feb. 29, 2008, 2 pages.
GenBank Accession No. XM_001725202.1, "Predicted: *Homo sapiens* similar to Putative uncharacterized protein PRO1933 (LOC100133188), mRNA," dated Feb. 29, 2008, 2 pages.
GenBank Accession No. O00767.2, "Acyl-CoA desaturase," dated Feb. 8, 2011, 6 pages.
Gurzell et al., "DHA-enriched fish oil targets B cell lipid microdomains and enhances ex vivo and in vivo B cell function," J. Leukoc. Biology, Apr. 2013, 93(4):463-470.
Hertzel et al., "Lipid metabolism and adipokine levels in fatty acid-binding protein null and transgenic mice," Am. J. Physiol. Endocrinol. Metabolism, May 2006, 290(5):E814-823.
Hobeika et al., "Testing gene function early in the B cell lineage in mb1-cre mice," Proc. Natl. Acad. Sci. USA, Sep. 12, 2006, 103(37):13789-13794.
Hotamisligil et al., "Metabolic functions of FABPs—mechanisms and therapeutic implications," Nat. Rev. Endocrinology, Oct. 2015, 11(10):592-605.
International Preliminary Report on Patentability in International Application No. PCT/US2018/020257 dated Sep. 12, 2019, 11 pages.
International Preliminary Report on Patentability in International Appln. No. PCT/US2021/037625, mailed on Dec. 29, 2022, 7 pages.
International Search Report & Written Opinion in International Application No. PCT/US2018/020257 dated May 14, 2018, 16 pages.
International Search Report and Written Opinion in International Appln. No. PCT/US2021/037625, mailed on Oct. 12, 2021, 9 pages.
Issandou et al., "Pharmacological inhibition of stearoyl-CoA desaturase 1 improves insulin sensitivity in insulin-resistant rat models," Eur J Pharmacol., 618(1-3):28-36, Epub Jul. 17, 2009.
Iwata et al., "Conditional Disruption of Raptor Reveals an Essential Role for mTORC1 in B Cell Development, Survival, and Metabolism," J. Immunology, Sep. 15, 2016, 197(6):2250-2260.
Jones et al., "mTOR has distinct functions in generating versus sustaining humoral immunity," J. Clin. Investigation, Nov. 1, 2016, 126(11):4250-4261.
Kaestner et al., "Differentiation-induced gene expression in 3T3-L1 preadipocytes. A second differentially expressed gene encoding stearoyl-CoA desaturase," J. Biol. Chemistry, Sep. 5, 1989, 264(25):14755-14761.
Kedia-Mehta et al., "Competition for nutrients and its role in controlling immune responses," Nat. Communications, May 9, 2019, 10(1):2123.
Kim et al., "Identification of genes differentially expressed in the renal cell carcinoma by microarray," The Korean Society for Laboratory Medicine, [author manuscript], 2009, 1 page.
Kim et al., "mTOR: a pharmacologic target for autophagy regulation," J. Clin. Investigation, Jan. 2015, 125(1):25-32.
Kim et al., "TopHat2: accurate alignment of transcriptomes in the presence of insertions, deletions and gene fusions," Genome Biology, Apr. 25, 2013, 14(4):R36, 13 pages.
Kosaraju et al., "B Cell Activity Is Impaired in Human and Mouse Obesity and Is Responsive to an Essential Fatty Acid upon Murine Influenza Infection," J. Immunology, Jun. 15, 2017, 198(12):4738-4752.
Koutsari et al., "Measuring plasma fatty acid oxidation with intravenous bolus injection of 3H- and 14C-fatty acid," J. Lipid Research, Jan. 2013, 54(1):254-264.
Kunisawa et al., "Regulation of intestinal IgA responses by dietary palmitic acid and its metabolism," J. Immunology, Aug. 15, 2014, 193(4):1666-1671.
Kurmi et al., "Carnitine Palmitoyltransferase 1A Has a Lysine Succinyltransferase Activity," Cell Reports, Feb. 6, 2018, 22(6):1365-1373.
Le et al., "Glucose-independent glutamine metabolism via TCA cycling for proliferation and survival in B cells," Cell Metabolism, Jan. 4, 2012, 15(1):110-121.
Lee et al., "Requirement for Rictor in homeostasis and function of mature B lymphoid cells," Blood, Oct. 3, 2013, 122(14):2369-2379.
Li et al., "Partial characterization of a cDNA for human stearoyl-CoA desaturase and changes in its mRNA expression in some normal and malignant tissues," Int J Cancer., 57(3):348-352, May 1994.
Liou et al., "Microarray gene expression profiling and analysis in renal cell carcinoma," BMC Urol., 4:9, 11 pages, Jun. 22, 2004.

(56) References Cited

OTHER PUBLICATIONS

Ma et al., "Serine Is an Essential Metabolite for Effector T Cell Expansion," Cell Metabolism, Feb. 7, 2017, 25(2):345-357.

Marlow et al., "cMyc expression and glycolysis addiction are necessary for SCD1 inhibitor response," Poster presented at the proceedings of the AACR Annual Meeting, Jun. 2020, 1 page.

McAnuff et al., "Potency of siRNA versus shRNA mediated knockdown in vivo," J Pharm Sci., 96(11):2922-2930, Nov. 2007.

Miyazaki et al., "A lipogenic diet in mice with a disruption of the stearoyl-CoA desaturase 1 gene reveals a stringent requirement of endogenous monounsaturated fatty acids for triglyceride synthesis," J. Lipid Research, Jul. 2001, 42(7):1018-1024.

Miyazaki et al., "Hepatic stearoyl-CoA desaturase-1 deficiency protects mice from carbohydrate-induced adiposity and hepatic steatosis," Cell Metab., Dec. 2007, 6(6):484-496.

Miyazaki et al., "Targeted disruption of stearoyl-CoA desaturase1 gene in mice causes atrophy of sebaceous and meibomian glands and depletion of wax esters in the eyelid," J. Nutrition, Sep. 2001, 131(9):2260-2268.

Mizushima et al., "The role of Atg proteins in autophagosome formation," Annu. Rev. Cell Dev. Biology, Nov. 2011, 27:107-132.

Moore et al., "Loss of stearoyl-CoA desaturase expression is a frequent event in prostate carcinoma," Int J Cancer., 114(4):563-571, Apr. 20, 2005.

Morgan-Lappe et al., "Identification of Ras-related nuclear protein, targeting protein for xenopus kinesin-like protein 2, and stearoyl-CoA desaturase 1 as promising cancer targets from an RNAi-based screen," Cancer Res., 67(9):4390-4398, May 1, 2007.

Ntambi et al., "Loss of stearoyl-CoA desaturase-1 function protects mice against adiposity," Proc. Natl. Acad. Sci. USA, Aug. 20, 2002, 99(17):11482-11486.

Ogasawara et al., "Stearoyl-CoA desaturase 1 activity is required for autophagosome formation," J. Biol. Chemistry, Aug. 22, 2014, 289(34):23938-23950.

O'Sullivan et al., "Memory CD8(+) T cells use cell-intrinsic lipolysis to support the metabolic programming necessary for development," Immunity, Jul. 17, 2014, 41(1):75-88.

Persson et al., "Rapid measurement of plasma free fatty acid concentration and isotopic enrichment using LC/MS," J. Lipid Research, Sep. 2010, 51(9):2761-2765.

Pisanu et al., "Inhibition of Stearoyl-CoA desaturase 1 reverts BRAF and MEK inhibition-induced selection of cancer stem cells in BRAF-mutated melanoma," J. Exp Clin. Cancer Res., Dec. 2018, 37(1):318.

PR Newswire [online], "Xenon and Novartis Sign Drug Development Deal for Obesity and Metabolic Disorders," Sep. 20, 2004 [retrieved on Apr. 23, 2015]. Retrieved from the Internet: <URL: http://www.prnewswire.com/news-releases/xenon-and-novartis-sign-drug-development-deal-for-obesity-and-metabolic-disorders-73785902.html> 3 pages.

PubChem [online], "2-(4-(2-(Trifluoromethyl)benzoyl)piperazin-1-yl)thiazole-5-carboxamide," PubChem CID 11973722, created Jan. 3, 2007, modified Apr. 19, 2015 [retrieved on Apr. 23, 2015]. Retrieved from the Internet: <URL: http://pubchem.ncbi.nlm.nih.gov/compound/11973722>, 13 pages.

Ramon et al., "Specialized proresolving mediators enhance human B cell differentiation to antibody-secreting cells," J. Immunology, Jul. 15, 2012, 189(2):1036-1042.

Ramon et al., "The specialized proresolving mediator 17-HDHA enhances the antibody-mediated immune response against influenza virus: a new class of adjuvant?" J. Immunol., Dec. 2014, 193(12):6031-6040.

Ramtohul et al., "Bicyclic heteroaryl inhibitors of stearoyl-CoA desaturase: from systemic to liver-targeting inhibitors," Bioorg Med Chem Lett., 21(19):5692-5696, Epub Aug. 12, 2011.

Rangel-Moreno et al., "B cells promote resistance to heterosubtypic strains of influenza via multiple mechanisms," J. Immunology, Jan. 1, 2008, 180(1):454-463.

Rathi et al, "Piperazine derivatives for therapeutic use: a patent review (2010-present)," Expert Opin. Ther. Pat., Jul. 2016, 26(7):777-797.

Raybuck et al., "B Cell-Intrinsic mTORC1 Promotes Germinal Center-Defining Transcription Factor Gene Expression, Somatic Hypermutation, and Memory B Cell Generation in Humoral Immunity," J. Immunology, Apr. 15, 2018, 200(8):2627-2639.

Rickert et al., "B lymphocyte-specific, Cre-mediated mutagenesis in mice," Nucleic Acids Research, Mar. 1, 1997, 25(6):1317-1318.

Robinson et al., "edgeR: a Bioconductor package for differential expression analysis of digital gene expression data," Bioinformatics, Jan. 2010, 26(1):139-140.

Roper et al., "Prostaglandin E2 promotes B lymphocyte Ig isotype switching to IgE," J. Immunology, Jan. 1, 1995, 154(1):162-170.

Roy et al., "Methionine Metabolism Shapes T Helper Cell Responses through Regulation of Epigenetic Reprogramming," Cell Metabolism, Feb. 4, 2020, 31(2):250-266.e9.

RTT News [online], "Merck Discontinues MK-3207 Clinical Development—Quick Facts," RTT News [online] Sep. 10, 2009 [retrieved on Apr. 23, 2015]. Retrieved from the Internet: <URL: http://www.rttnews.com/1062949/merck-discontinues-mk-3207-clinical-development-quick-facts.aspx>, 3 pages.

Rytter et al., "The immune system in children with malnutrition—a systematic review," PLoS One, Aug. 25, 2014, 9(8):e105017, 19 pages.

Shin et al., "Analysis of the free fatty acid metabolome in the plasma of patients with systemic lupus erythematosus and fever," Metabolomics, Apr. 2018, 14:14, 10 pages.

Siegemund et al., "hCD2-iCre and Vav-iCre mediated gene recombination patterns in murine hematopoietic cells," PLoS One, Apr. 17, 2015, 10(4):e0124661, 17 pages.

Son et al., "Inhibition of Stearoyl-CoA desaturases suppresses follicular help T and germinal center B cell responses," Eur. J. Immunology, Jul. 2020, 50(7):1067-1077.

Tan et al., "Critical role of SCD1 in autophagy regulation via lipogenesis and lipid rafts-coupled AKT-FOXO1 signaling pathway," Autophagy, Feb. 2014, 10(2):226-242.

Uto et al., "Novel benzoylpiperidine-based stearoyl-CoA desaturase-1 inhibitors: Identification of 6-[4-(2-methylbenzoyl)piperidin-1-yl]pyridazine-3-carboxylic acid (2-hydroxy-2-pyridin-3-ylethyl)amide and its plasma triglyceride-lowering effects in Zucker fatty rats," Bioorg Med Chem Lett., 20(1):341-345, Epub Oct. 29, 2009.

Wang et al., "RSeQC: quality control of RNA-seq experiments," Bioinformatics, Aug. 15, 2012, 28(16):2184-2185.

Wang et al., "The transcription factor Myc controls metabolic reprogramming upon T lymphocyte activation," Immunity, Dec. 23, 2011, 35(6):871-882.

Waters et al., "Initial B Cell Activation Induces Metabolic Reprogramming and Mitochondrial Remodeling," iScience, Jul. 27, 2018, 5:99-109.

Wei et al., "Saturated fatty acids induce endoplasmic reticulum stress and apoptosis independently of ceramide in liver cells," Am. J. Physiol. Endocrinol. Metabolism, Aug. 2006, 291(2):E275-281.

Weisel et al., "Germinal center B cells selectively oxidize fatty acids for energy while conducting minimal glycolysis," Nat. Immunology, Mar. 2020, 21(3):331-342.

Zeng et al., "Discrete roles and bifurcation of PTEN signaling and mTORC1-mediated anabolic metabolism underlie IL-7-driven B lymphopoiesis," Sci. Advances, Jan. 31, 2018, 4(1):eaar5701.

Zeng et al., "mTORC1 and mTORC2 Kinase Signaling and Glucose Metabolism Drive Follicular Helper T Cell Differentiation," Immunity, Sep. 20, 2016, 45(3):540-554.

Zeng et al., "mTORC1 couples immune signals and metabolic programming to establish T(reg)-cell function," Nature, Jul. 25, 2013, 499(7459):485-490.

Zeng, "Metabolic regulation of lymphocytes in health and autoimmunity," Presented in Chile, Aug. 27, 2019, 41 pages.

Zhao et al., "Discovery of 1-(4-phenoxypiperidin-1-yl)-2-arylaminoethanone stearoyl-CoA desaturase 1 inhibitors," Bioorg Med Chem Lett., 17(12):3388-3391, Epub Apr. 5, 2007.

(56) References Cited

OTHER PUBLICATIONS

Zhou et al., "Stearoyl-CoA Desaturase-Mediated Monounsaturated Fatty Acid Availability Supports Humoral Immunity," Cell Reports, Jan. 5, 2021, 34(1):108601.
U.S. Appl. No. 15/692,491, filed Aug. 31, 2017, John A. Copland III, Issued as U.S. Pat. No. 10,160,972.
U.S. Appl. No. 17/410,137, filed Aug. 24, 2021, John A. Copland III, Issued as U.S. Pat. No. 11,833,144.
U.S. Appl. No. 17/928,503, filed Nov. 29, 2022, John A. Copland III, Published as U.S. Publication No. 2023/02011192.
U.S. Appl. No. 18/101,772, filed Jan. 26, 2023, John A. Copland III, Published as U.S. Publication No. 2023/0310419.

* cited by examiner

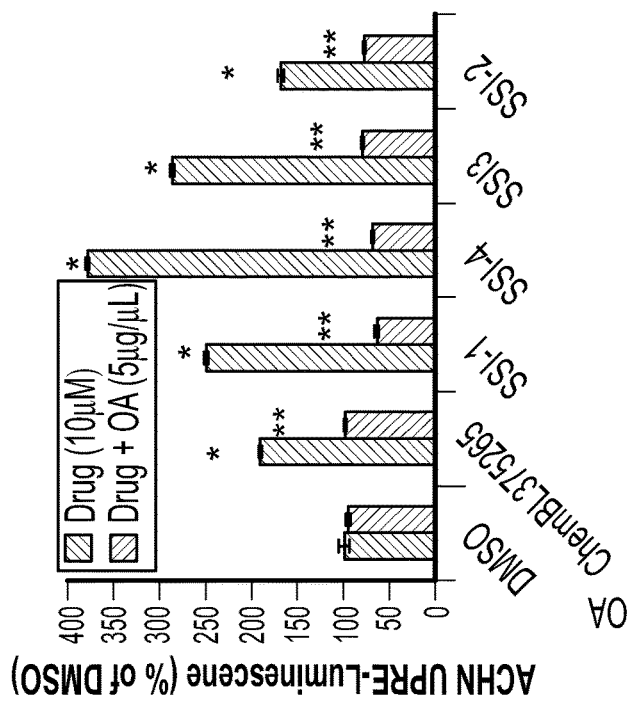
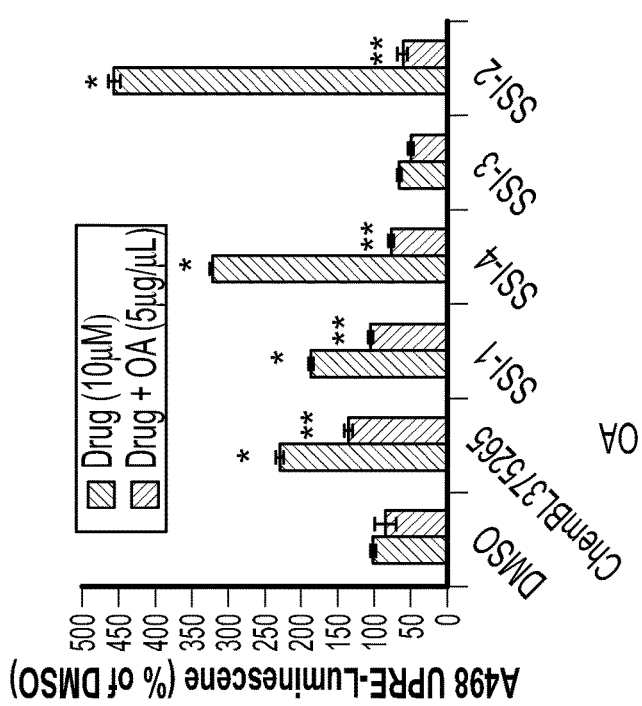
FIG. 3A
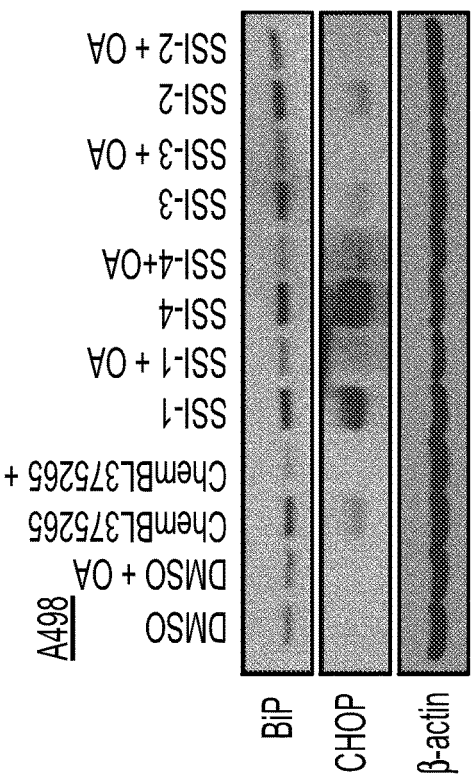
FIG. 3B

| Cancer Type | Score | | # Studies | Up or Down-regulated in Tumor |
|---|---|---|---|---|
| Kidney Cancer | 69 | RE | 22 | ▲Up-regulated |
| Liver Cancer | 53 | RE CN | 31 | ▲Up-regulated |
| Breast Cancer | 47 | RE | 40 | ▲Up-regulated |
| Other Leukemia | 45 | RE | 3 | ▼Down-regulated |
| Adrenal Cancer | 44 | RE | 5 | ▲Up-regulated |
| Other Lymphoma | 44 | RE | 5 | ▲Up-regulated |
| Other Cancer | 43 | RE CN | 27 | ▼Down-regulated |
| T-cell Lymphoma | 43 | RE CN | 8 | ▼Down-regulated |
| Myeloid Leukemia | 41 | RE CN | 21 | ▼Down-regulated |
| Malignant Tumor of Muscle | 40 | RE CN | 12 | ▲Up-regulated |
| Brain Cancer | 39 | RE CN | 35 | ▼Down-regulated |
| Malignant Tumor of Intestine | 39 | RE CN | 42 | ▲Up-regulated |
| Cancer of Thymus | 37 | RE | 2 | ▲Up-regulated |
| Uterine Cancer | 36 | RE SM CN | 7 | ▲Up-regulated |
| Prostate Cancer | 36 | RE SM CN | 16 | ▼Down-regulated |
| Gastric Cancer | 34 | RE | 9 | ▲Up-regulated |
| Bladder Cancer | 34 | RE SM CN | 12 | ▼Down-regulated |
| Thyroid Cancer | 33 | RE | 9 | ▲Up-regulated |
| Lymphoid Leukemia | 33 | RE CN | 13 | ▼Down-regulated |
| Secondary Malignant Neoplastic Disease | 31 | RE SM CN | 25 | ▲Up-regulated |
| Cancer of Head and Neck | 31 | RE | 6 | ▲Up-regulated |
| Lung Cancer | 30 | RE | 22 | ▲Up-regulated |
| Neuroendocrine Tumor | 30 | RE CN | 11 | ▼Down-regulated |
| Pancreatic Cancer | 28 | RE | 10 | ▲Up-regulated |
| Skin Cancer | 25 | RE SM CN | 15 | ▼Down-regulated |
| B-cell Lymphoma | 21 | RE | 8 | ▼Down-regulated |
| Esophageal Cancer | 17 | RE | 5 | ▼Down-regulated |
| Primary Malignant Neoplasm of Bone | 14 | RE CN | 6 | ▲Up-regulated |
| Ovarian Cancer | 11 | RE | 10 | ▲Up-regulated |
| Testicular Cancer | 10 | RE | 3 | ▼Down-regulated |
| Multiple Myeloma/Plasmacytoma | 0 | RE | 2 | ▼Down-regulated |

FIG. 4

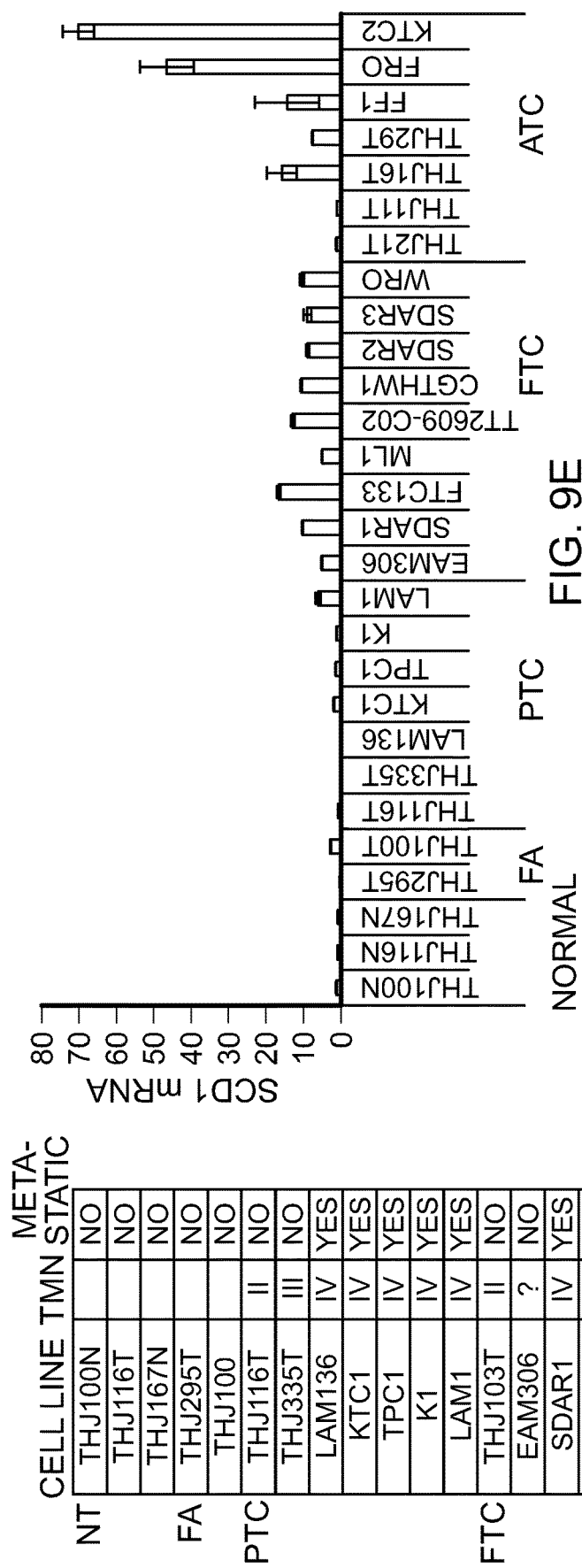
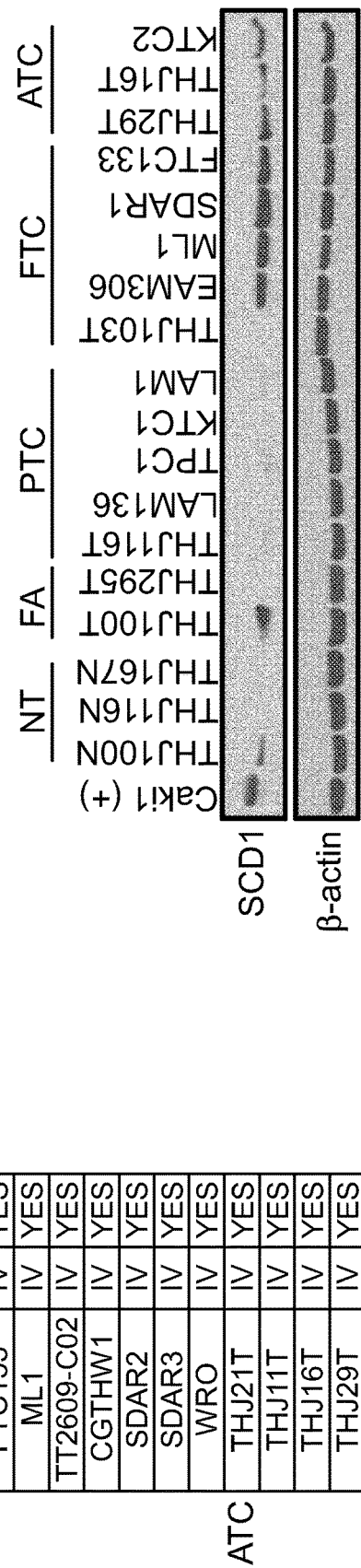
FIG. 9D
FIG. 9E
FIG. 9F

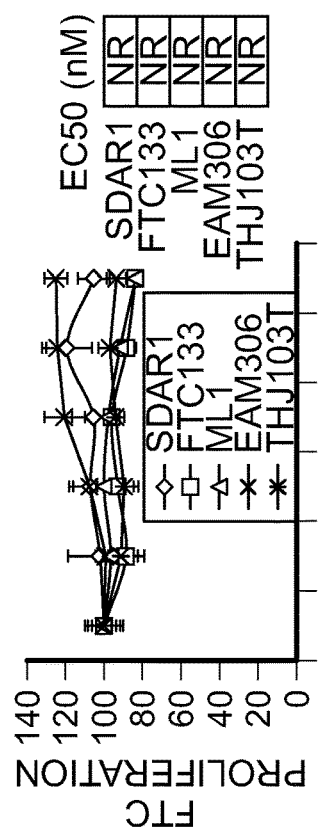
FIG. 10A
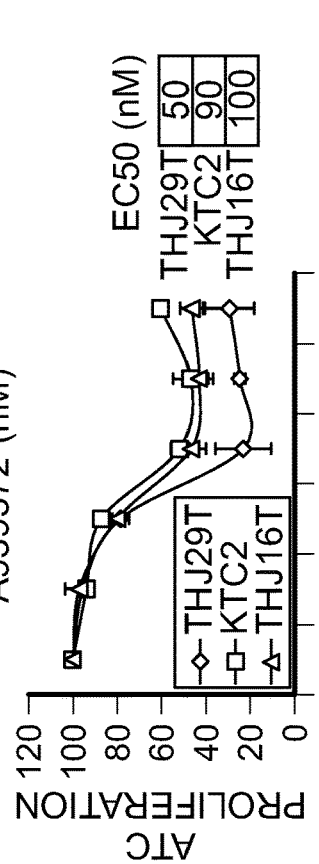
FIG. 10B
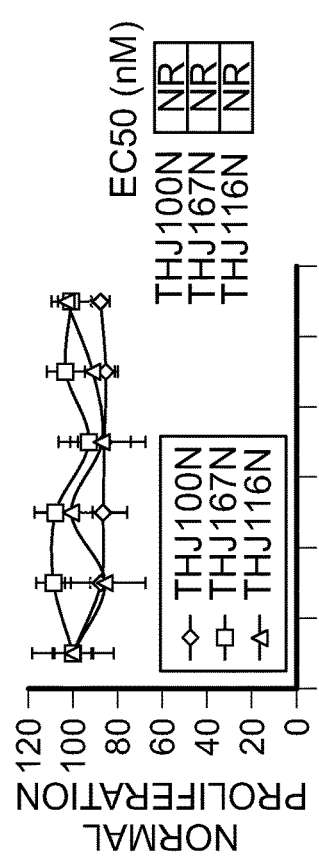
FIG. 10D
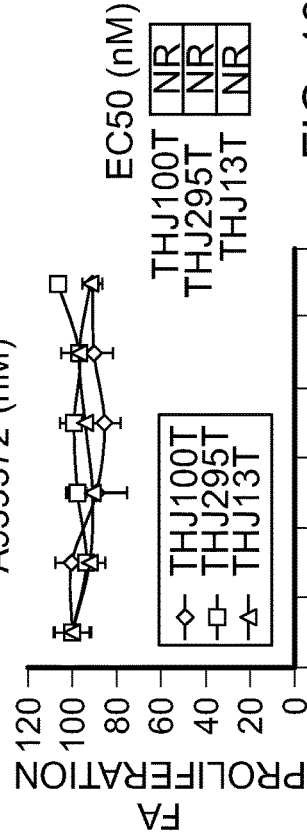
FIG. 10E
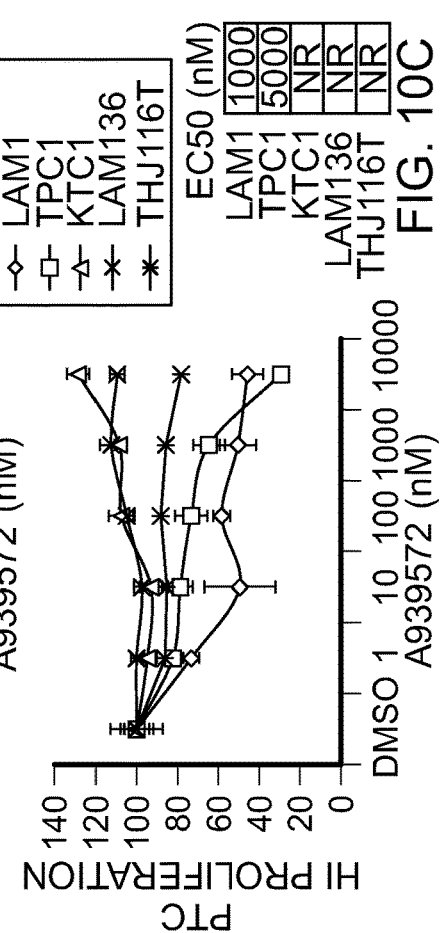
FIG. 10C / FIG. 10F
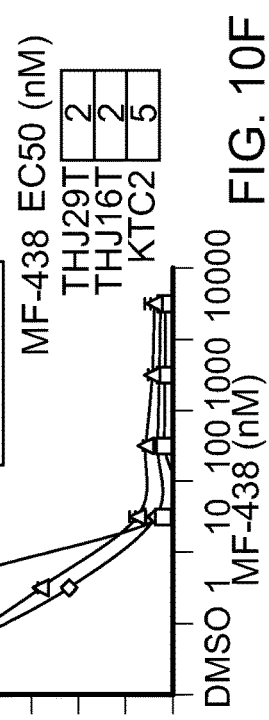

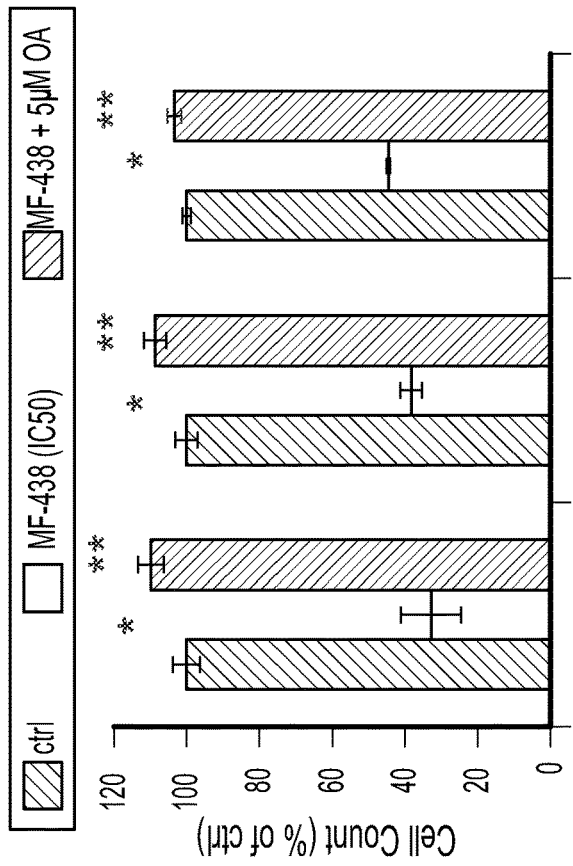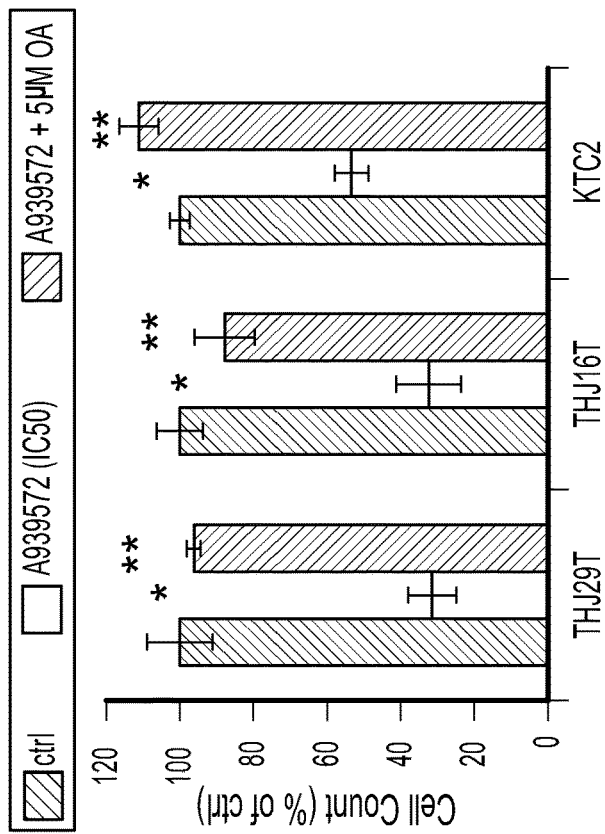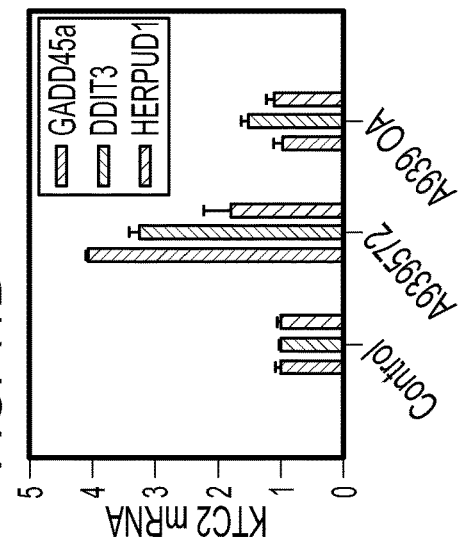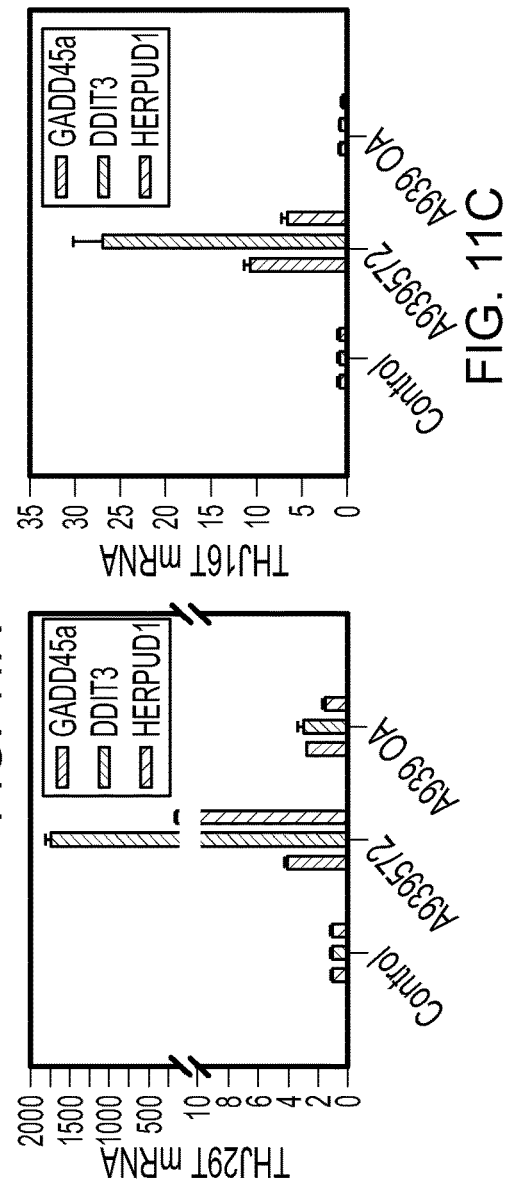
FIG. 11A
FIG. 11B
FIG. 11C

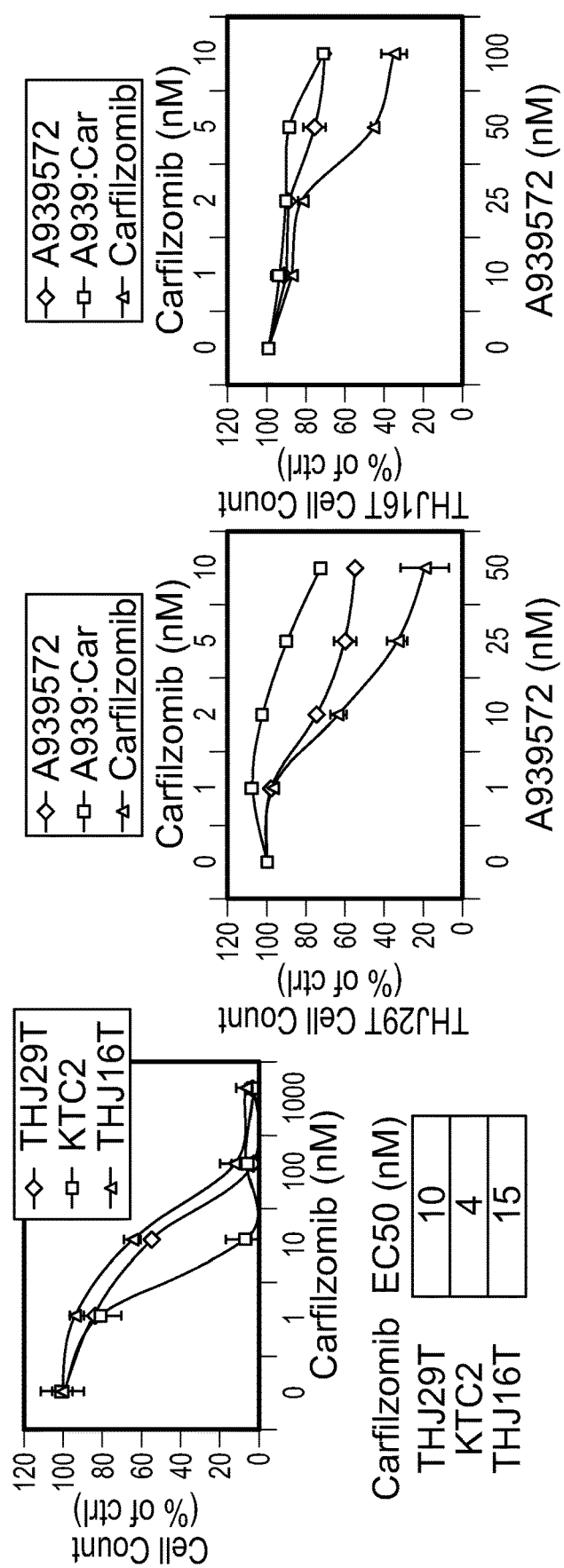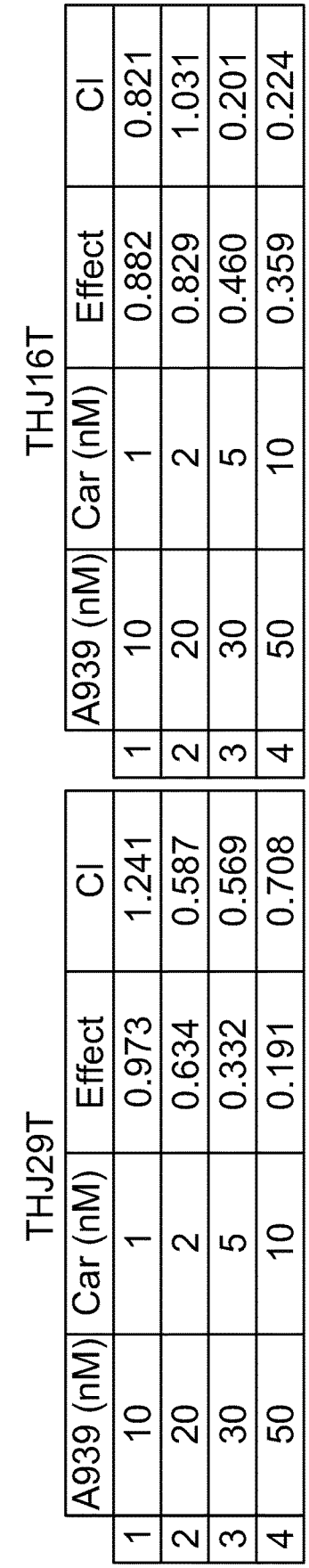
FIG. 12A
FIG. 12B
FIG. 12C

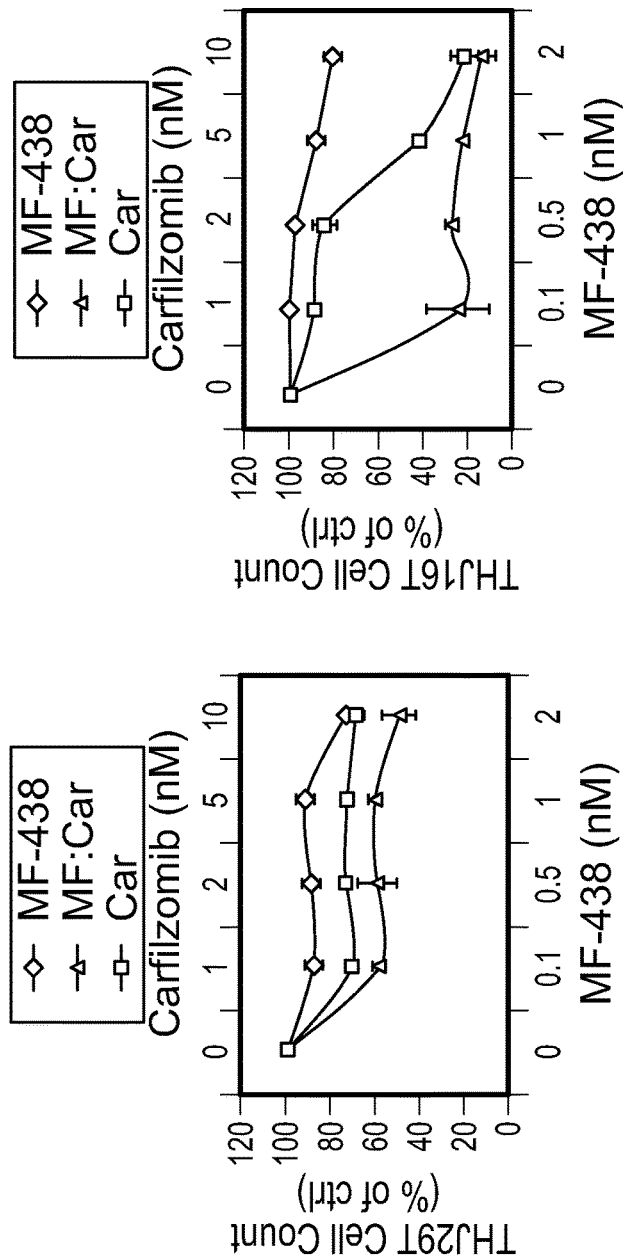
FIG. 12D
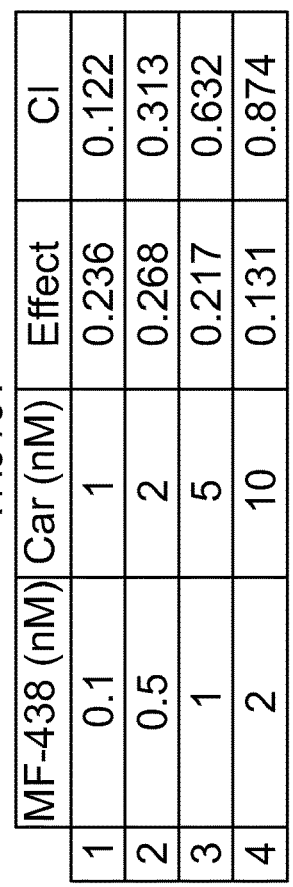
FIG. 12E
| | MF-438 (nM) | Car (nM) | Effect | CI |
|---|---|---|---|---|
| 1 | 0.1 | 1 | 0.236 | 0.122 |
| 2 | 0.5 | 2 | 0.268 | 0.313 |
| 3 | 1 | 5 | 0.217 | 0.632 |
| 4 | 2 | 10 | 0.131 | 0.874 |
THJ16T
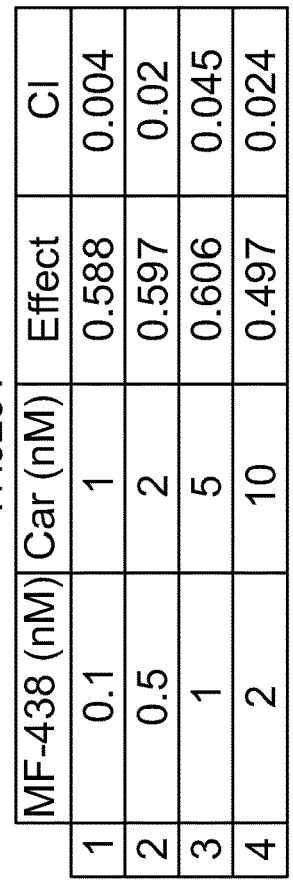
| | MF-438 (nM) | Car (nM) | Effect | CI |
|---|---|---|---|---|
| 1 | 0.1 | 1 | 0.588 | 0.004 |
| 2 | 0.5 | 2 | 0.597 | 0.02 |
| 3 | 1 | 5 | 0.606 | 0.045 |
| 4 | 2 | 10 | 0.497 | 0.024 |
THJ29T

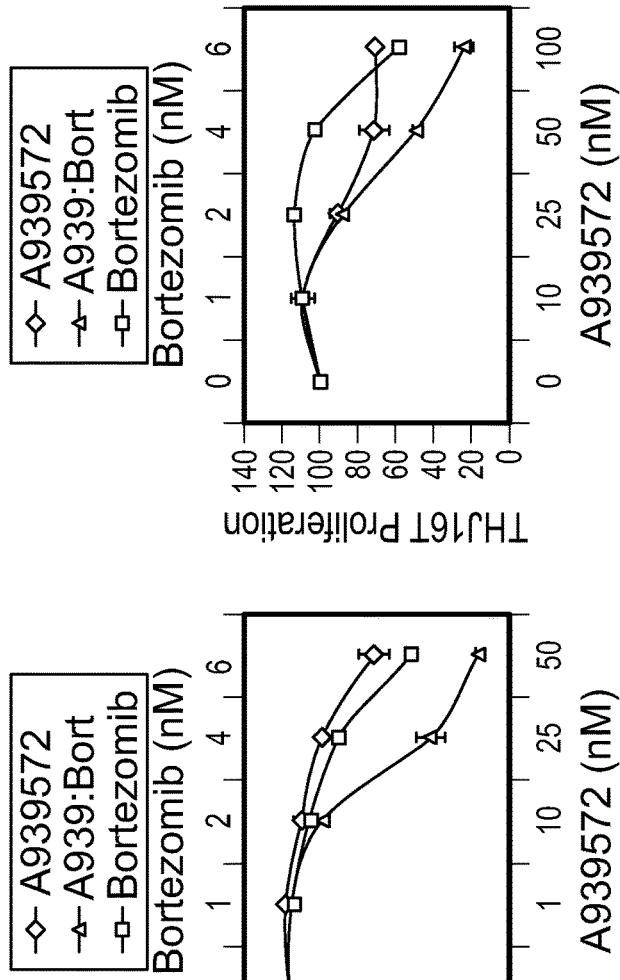
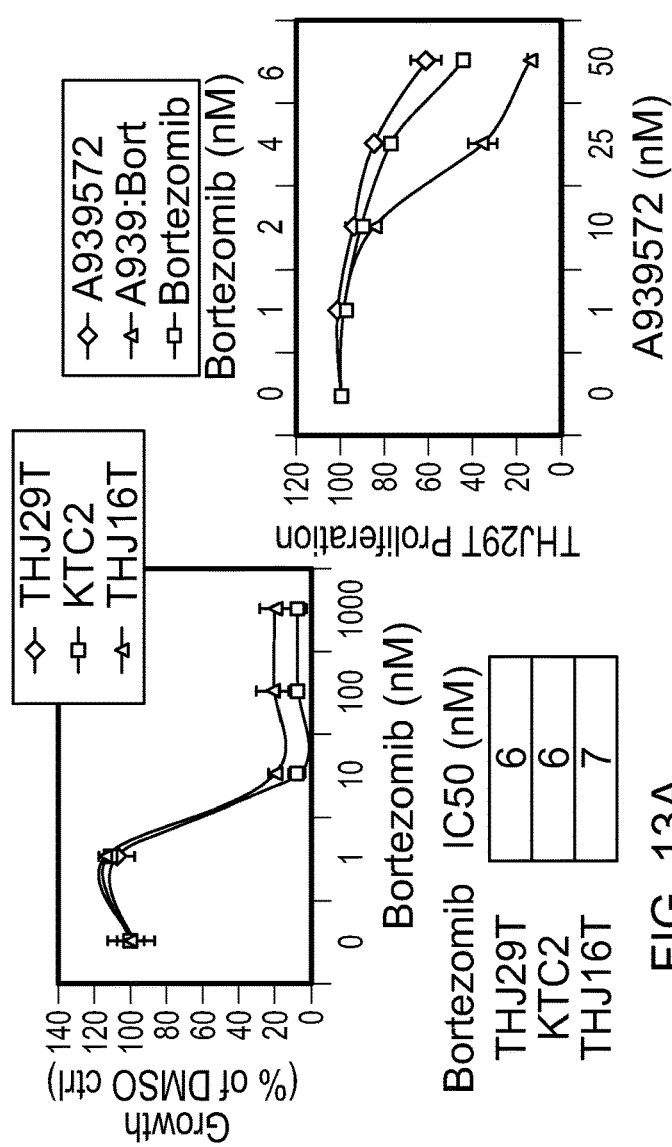
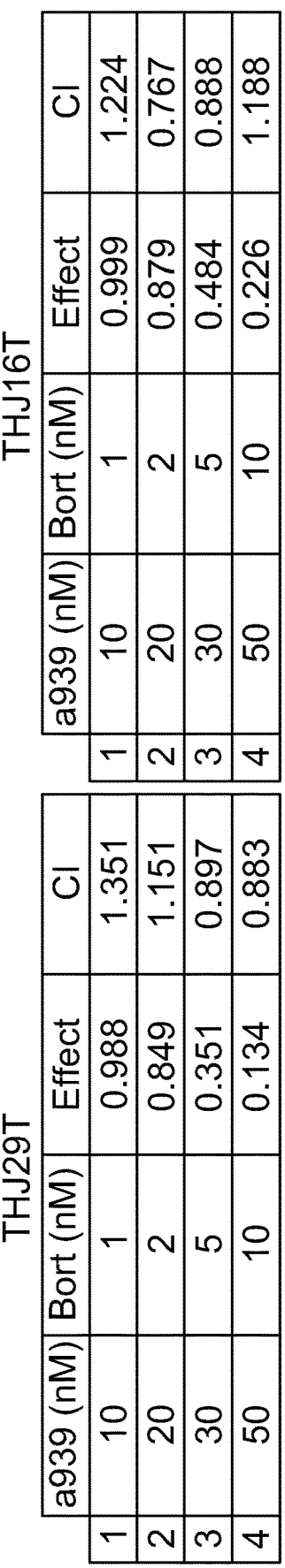
FIG. 13A
FIG. 13B
FIG. 13C

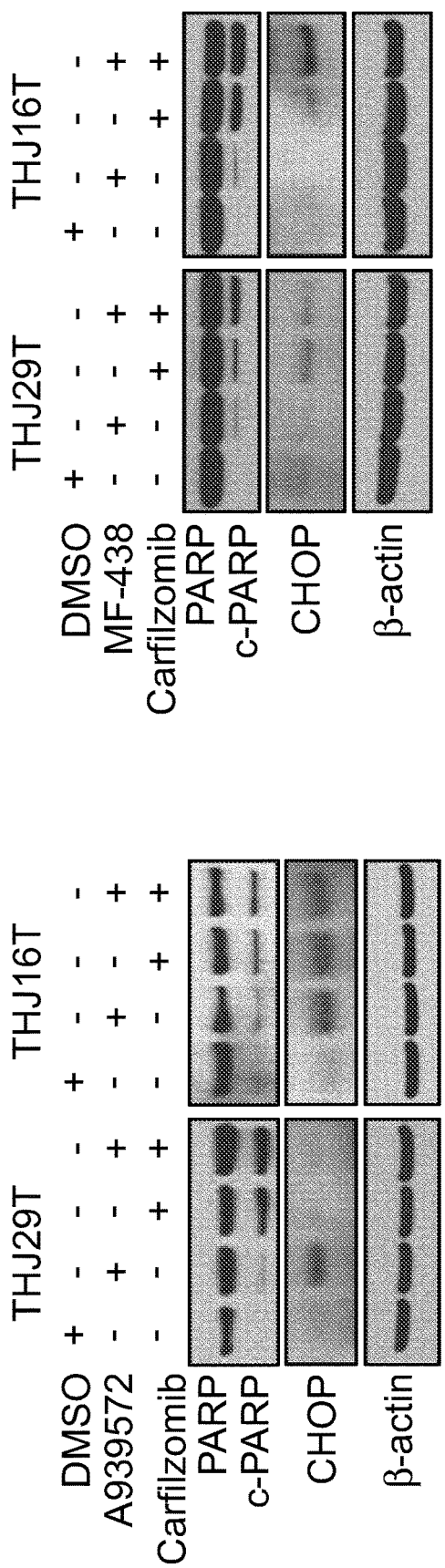
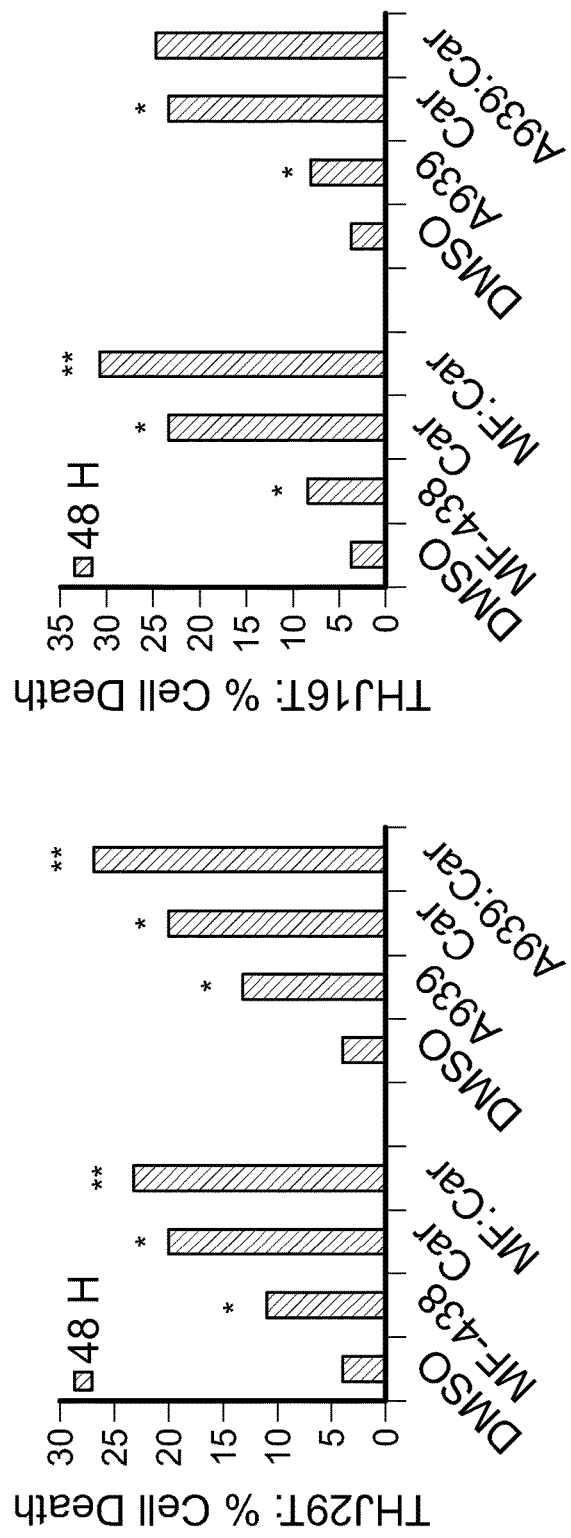
FIG. 14A
FIG. 14B
FIG. 14C

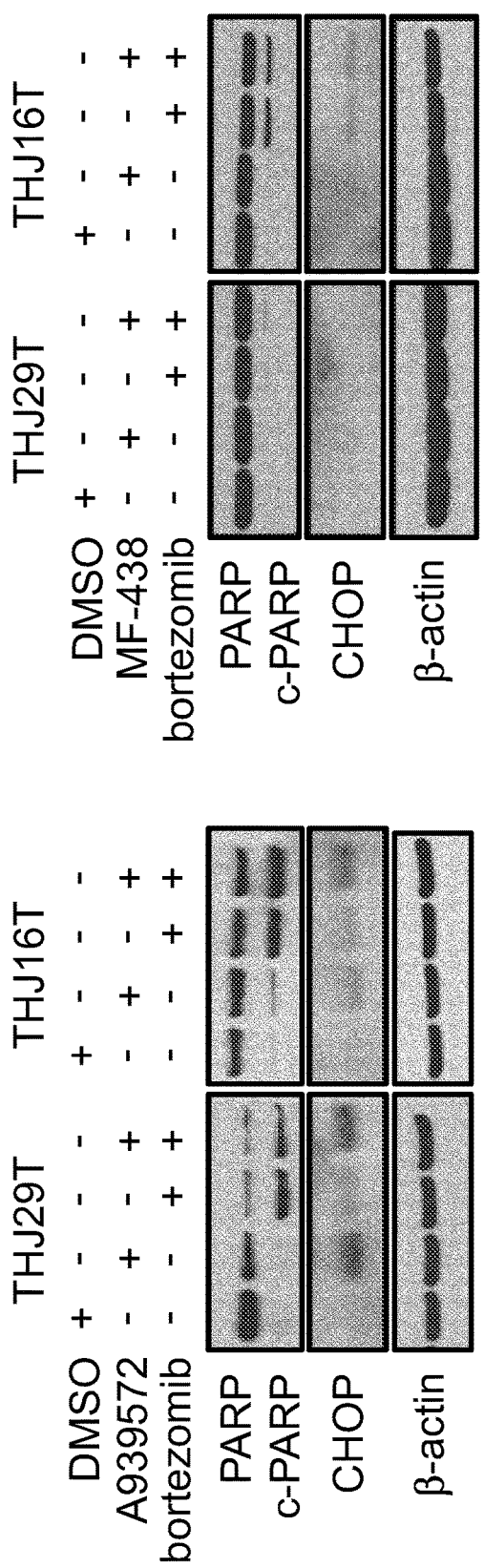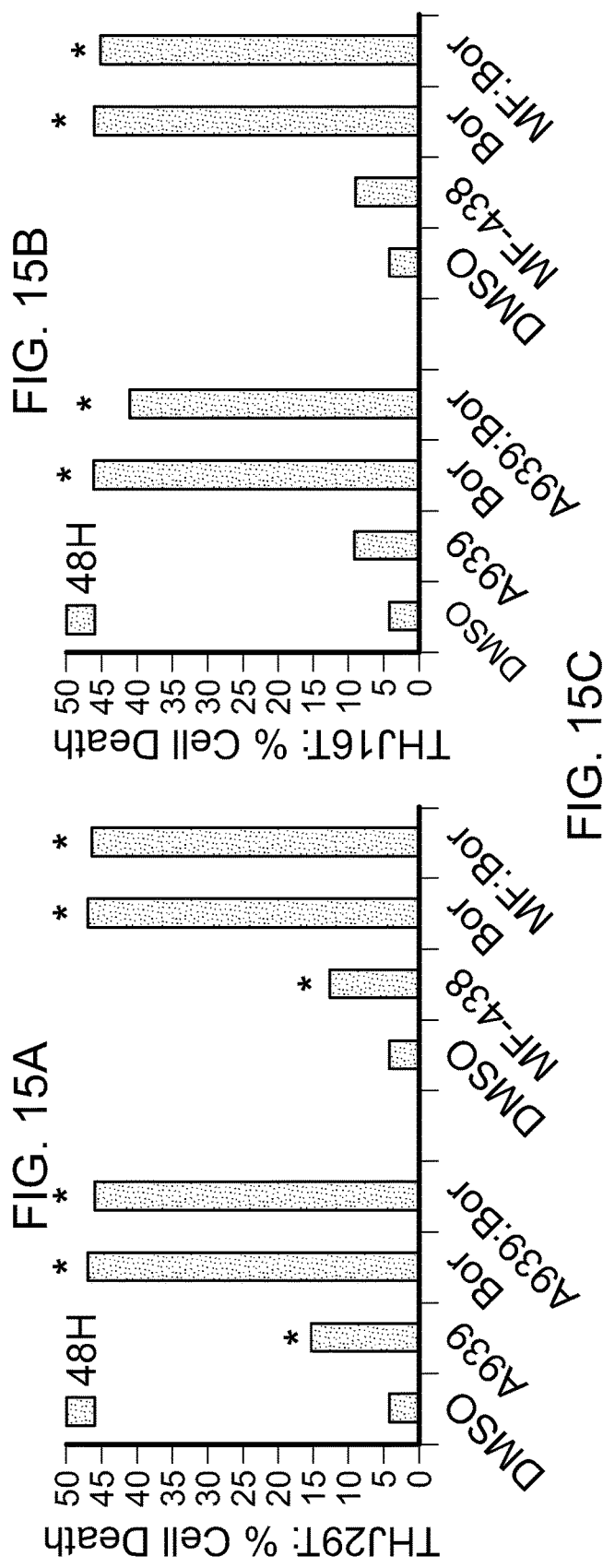
FIG. 15A
FIG. 15B
FIG. 15C

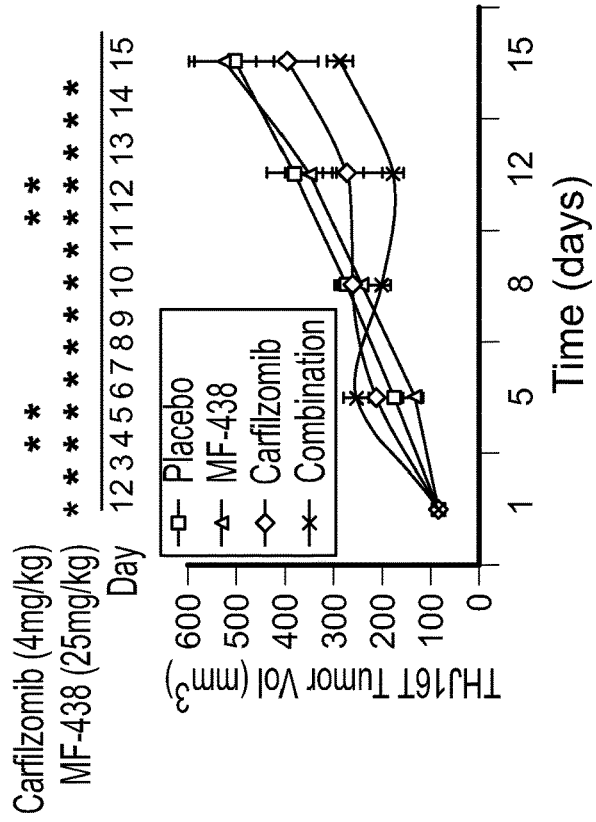
FIG. 17A
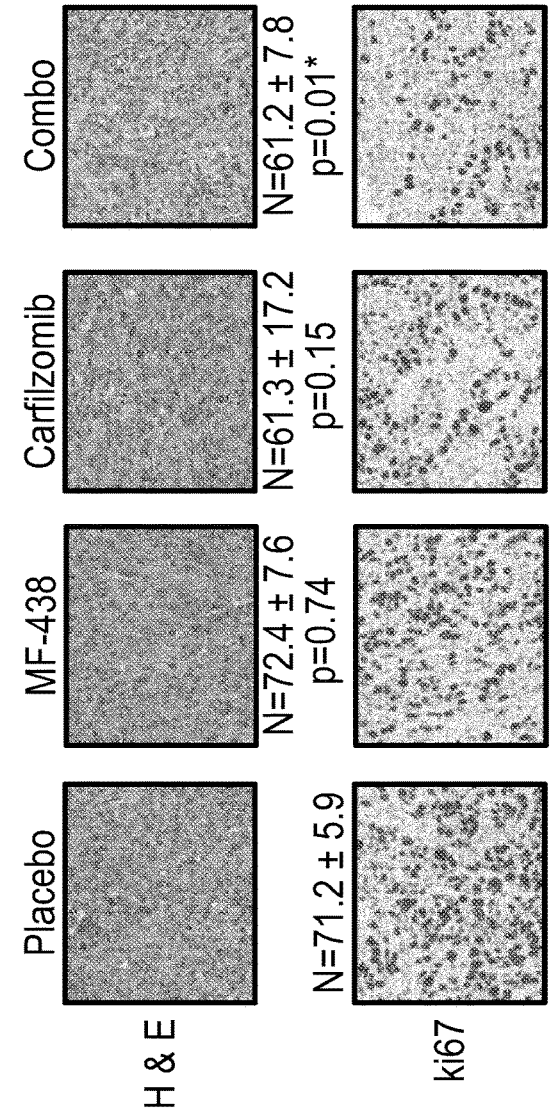
FIG. 17B
FIG. 17C

SEQUENCE LISTING

```
<160> NUMBER OF SEQ ID NOS: 1

<210> SEQ ID NO 1
<211> LENGTH: 359
<212> TYPE: PRT
<213> ORGANISM: Homo sapiens

<400> SEQUENCE: 1

Met Pro Ala His Leu Leu Gln Asp Asp Ile Ser Ser Tyr Thr Thr
1               5                   10                  15

Thr Thr Thr Ile Thr Ala Pro Pro Ser Arg Val Leu Gln Asn Gly Gly
                20                  25                  30

Asp Lys Leu Glu Thr Met Pro Leu Tyr Leu Glu Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Phe Val Ser Ala
                100                 105                 110

Leu Gly Ile Thr Ala Gly Ala His Arg Leu Trp Ser His Arg Ser Tyr
            115                 120                 125

Lys Ala Arg Leu Pro Leu Arg Leu Phe Leu Ile Ile Ala Asn Thr Met
        130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
            180                 185                 190

Val Lys Glu Lys Gly Ser Thr Leu Asp Leu Ser Asp Leu Glu Ala Glu
        195                 200                 205

Lys Leu Val Met Phe Gln Arg Arg Tyr Tyr Lys Pro Gly Leu Leu Met
    210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
            260                 265                 270

Tyr Arg Pro Tyr Asp Lys Asn Ile Ser Pro Arg Glu Asn Ile Leu Val
        275                 280                 285

Ser Leu Gly Ala Val Gly Glu Gly Phe His Asn Tyr His His Ser Phe
    290                 295                 300
```

-continued

```
Pro Tyr Asp Tyr Ser Ala Ser Glu Tyr Arg Trp His Ile Asn Phe Thr
305             310             315                 320

Thr Phe Phe Ile Asp Cys Met Ala Ala Leu Gly Leu Ala Tyr Asp Arg
                325             330                 335

Lys Lys Val Ser Lys Ala Ala Ile Leu Ala Arg Ile Lys Arg Thr Gly
                340             345             350

Asp Gly Asn Tyr Lys Ser Gly
            355
```

COMPOUNDS AND METHODS FOR TREATING CANCER

CROSS REFERENCE TO RELATED APPLICATIONS

This application is a continuation of U.S. application Ser. No. 16/422,519 filed May 24, 2019, which is a continuation of U.S. application Ser. No. 15/502,301, filed Feb. 7, 2017, which is a National Stage Application under 35 U.S.C. § 371 of International Application No. PCT/US2015/044278, filed Aug. 7, 2015, which claims the benefit of U.S. Provisional Ser. No. 62/034,429 filed Aug. 7, 2014. This disclosures of the prior applications are considered part of (and are incorporated by reference in) the disclosure of this application.

BACKGROUND

Technical Field

This document relates to methods and materials involved in treating cancer, for example, renal cell carcinoma, melanoma, and ovarian, breast, prostate, colon, pancreatic, bladder, liver, lung, and thyroid cancers. For example, this document provides methods and material for using one or more inhibitors of a stearoyl-Coenzyme A desaturase 1 (SCD1) enzyme to treat cancer.

Background Information

The incidence and deaths caused by renal cell carcinoma are increasing in the United States. Indeed, mortality from renal cell carcinoma has increased over 37% since 1950.

SCD1 is an enzyme that catalyzes the de novo lipogenesis of Δ-9 monounsaturated fatty acids (MUFA) oleic acid (OA) and palmitoleic acid (PA). These MUFAs are essential for the synthesis of triglycerides, sphingolipids, ceramides, glycolipids, phospholipids, and other lipoproteins which influence membrane fluidity, membrane raft formation and receptor clustering, second messenger signaling, fatty acid oxidation, energy storage, cell division, inflammation, and a number of other biological functions. SCD1 has been implicated as pro-tumorigenic in a multitude of cancers, such as clear cell renal cell carcinoma (ccRCC).

SUMMARY

Provided herein is a compound according to Formula (I):

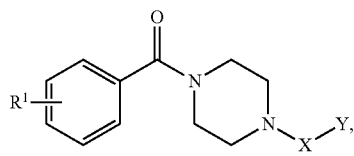

(I)

or a pharmaceutically acceptable salt thereof, wherein:

$R^1$ is an unsubstituted $C_{1-6}$alkyl or $C_{1-6}$haloalkyl;

X is

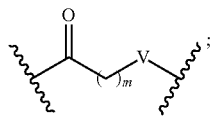

Y is selected from the group consisting of:

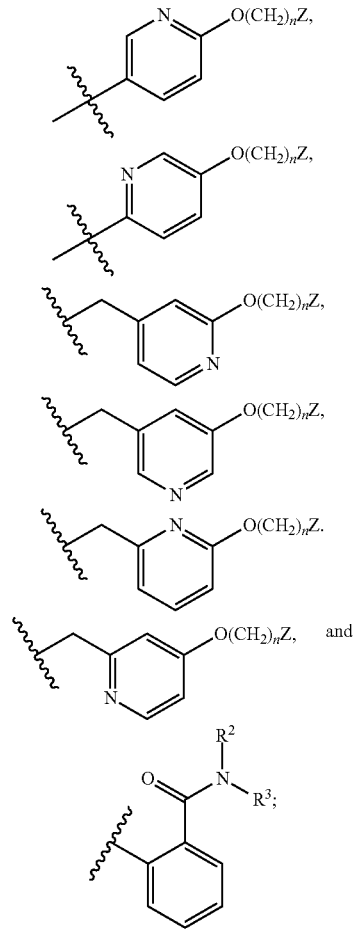

m is 0 or 1;
n is 0, 1, or 2;
V is $NR^4$ or O;
$R^2$, $R^3$, and $R^4$ are each independently H or an unsubstituted $C_{1-6}$alkyl; and
Z is an unsubstituted aryl.

In some embodiments, the compound according to Formula (I) has the structure of Formula (Ia):

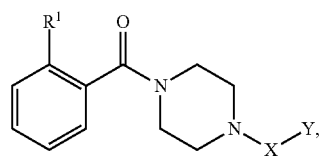

(Ia)

or a pharmaceutically acceptable salt thereof.

In some embodiments, $R^1$ is $CF_3$.

In some embodiments, $R^2$ is H; and $R^3$ is $CH_3$.

In some embodiments, m is 0. In some embodiments, m is 1.

In some embodiments, n is 1.

In some embodiments, V is NH. In some embodiments, V is O.

In some embodiments, Y is

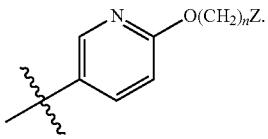

In some embodiments, Y is

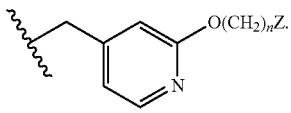

In some embodiments, Y is

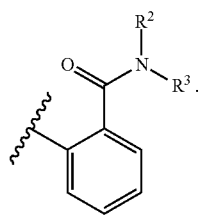

In some embodiments, Z is phenyl.

In some embodiments, the compound according to Formula (I) is selected from the group consisting of:

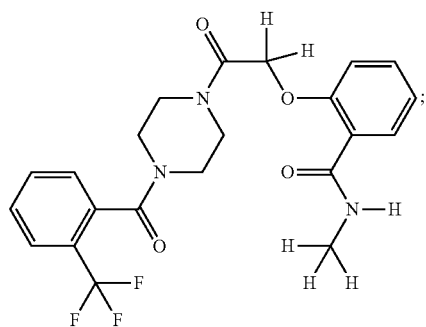

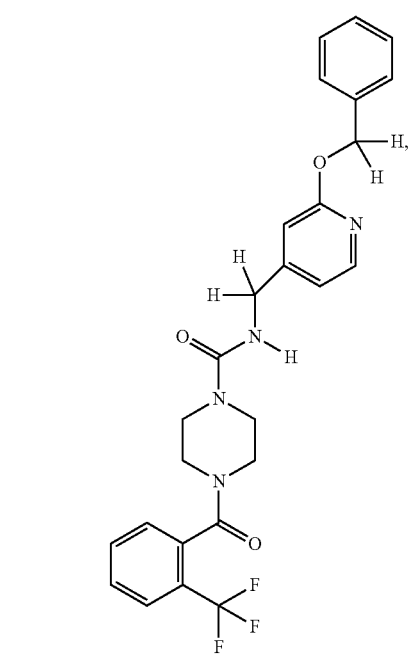

or a pharmaceutically acceptable salt thereof.

The disclosure also provides a compound according to Formula (II):

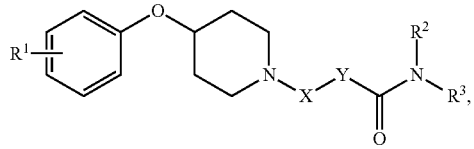

or a pharmaceutically acceptable salt thereof, wherein $R^1$ is halo;

X is —(C=O)$NR^4$—;

Y is

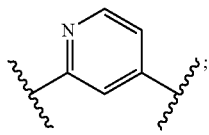 [SMILES: *c1ccnc(*)c1]

and

R², R³, and R⁴ are each independently H or an unsubstituted $C_{1-6}$alkyl.

In some embodiments, the compound according to Formula (II) has the structure of Formula (IIa):

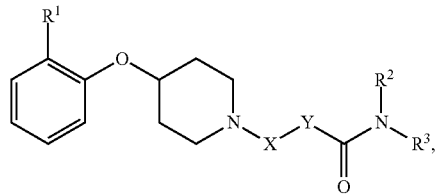

(IIa)

or a pharmaceutically acceptable salt thereof.

In some embodiments, R¹ is Cl.

In some embodiments, R² is H; and R³ is $CH_3$.

In some embodiments, R⁴ is H.

In some embodiments, the compound according to Formula (II) is

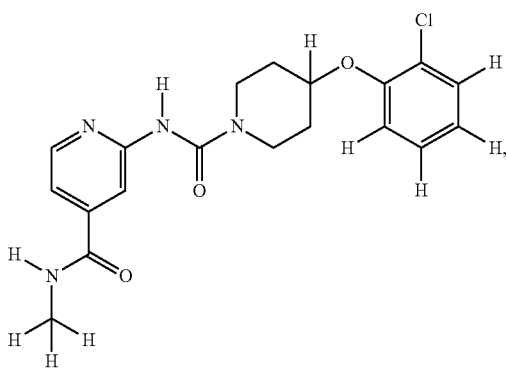

or a pharmaceutically acceptable salt thereof.

Provided herein is also a pharmaceutical composition comprising a compound as described herein and a pharmaceutically acceptable carrier.

The disclosure also provides a method for inhibiting SCD1 in a cell, comprising contacting the cell with an effective amount of a compound, a pharmaceutically acceptable salt thereof, or a pharmaceutical composition as described herein.

In some embodiments, the cell is a cancer cell. In some embodiments, the cancer cell is selected from the group consisting of a kidney cancer cell, a liver cancer cell, a breast cancer cell, a lung cancer cell, a pancreatic cancer cell, a bladder cancer cell, a colon cancer cell, a melanoma cell, a thyroid cancer cell, an ovarian cancer cell, and a prostate cancer cell. For example, the cancer cell can be a kidney cancer cell.

In some embodiments, the contacting is in vitro. In some embodiments, the contacting is in vivo.

The disclosure further provides a method for treating a cancer in a subject in need thereof, comprising administering to the subject a therapeutically effective amount of a compound or a pharmaceutical composition as described herein.

In some embodiments, the subject is a mammal. In some embodiments, the subject is human.

In some embodiments, the cancer comprises a solid tumor. In some embodiments, the cancer is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer. In some embodiments, the cancer is a kidney cancer or a bladder cancer. In some embodiments, the cancer is a kidney cancer. For example, the kidney cancer can be clear cell renal cell carcinoma. In some embodiments, the cancer is a bladder cancer. In some embodiments, the bladder cancer is selected from the group consisting of: transitional cell carcinoma, urothelial carcinoma, papillary carcinoma, flat carcinoma, squamous cell carcinoma, adenocarcinoma, small-cell carcinoma, and sarcoma. For example, the bladder cancer can be transitional cell carcinoma. In some embodiments, the cancer is a thyroid cancer.

The disclosure further provides a method of treating a cancer as described herein in a subject in need thereof, comprising administering to the subject a therapeutically effective amount of an SCD1 inhibitor and a proteasome inhibitor, or pharmaceutically acceptable salts thereof, or a composition comprising the SCD1 inhibitor and the proteasome inhibitor.

In some embodiments, the SCD1 inhibitor and the proteasome inhibitor are admixed prior to administration. In some embodiments, the SCD1 inhibitor and the proteasome inhibitor are administered concurrently. In some embodiments, the SCD1 inhibitor and the proteasome inhibitor are administered sequentially. In some embodiments, the SCD1 inhibitor is administered prior to the administration of the proteasome inhibitor. In some embodiments, the proteasome inhibitor is administered prior to the administration of the SCD1 inhibitor. In some embodiments the cancer is a thyroid cancer (e.g., anaplastic thyroid cancer).

The disclosure further provides a method of treating a cancer as described herein in a subject in need thereof, comprising administering to the subject a therapeutically effective amount of a compound as described herein and an mTor inhibitor, or pharmaceutically acceptable salts thereof, or a composition as described herein and the mTor inhibitor.

In some embodiments, the compound and the mTor inhibitor are admixed prior to administration. In some embodiments, the compound and the mTor inhibitor are administered concurrently. In some embodiments, the compound and the mTor inhibitor are administered sequentially. In some embodiments, the compound is administered prior to the administration of the mTor inhibitor. In some embodiments, the mTor inhibitor is administered prior to the administration of the compound.

The disclosure further provides a method of treating a cancer as described herein in a subject in need thereof, comprising administering to the subject a therapeutically effective amount of a compound as described herein and sorafenib, or pharmaceutically acceptable salts thereof, or a composition as described herein and sorafenib.

In some embodiments, the compound and sorafenib are admixed prior to administration. In some embodiments, the compound and sorafenib are administered concurrently. In some embodiments, the compound and sorafenib are administered sequentially. In some embodiments, the compound is administered prior to the administration of sorafenib. In some embodiments, sorafenib is administered prior to the administration of the compound. In some embodiments, the cancer is a liver cancer (e.g., hepatobiliary carcinoma (HCC)).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2A shows the Oleic acid rescue assay in A498, ACHN, and Caki1 cells treated with the $EC_{50}$ doses of known (MF-438, ChemBL375265 [ChemBL]) and SCD1 inhibitors of the disclosure. (*) indicates significant decrease in proliferation in $EC_{50}$ treated cells as compared to DMSO control, and () indicates significant increase in cell proliferation with $EC_{50}$ treated concomitantly with OA as compared to $EC_{50}$ treated cells alone. FIG. 2B** shows representative phase-contrast images of A498 ccRCC cells depicting cell morphology and density in response to $EC_{50}$ treatment with indicated SCD1 inhibitors+/−OA.

FIGS. 3A-3B show the effect of SCD1 inhibitors in ccRCC cells. Selective SCD1 inhibitors (SSI) are shown in the Figure as follows: FIG. 3A shows luciferase assay of A498 and ACHN transfected with an ATF6-UPRE luciferase reporter treated with the $EC_{50}$ doses of ChemBL375265, +/−OA supplementation. Results are presented as relative luminescence. (*) indicates significant increase in luciferase activity in $EC_{50}$ treated cells as compared to DMSO control, and () indicates significant reduction in luciferase activity in $EC_{50}$ treated concomitantly with OA as compared to $EC_{50}$ treated cells alone. FIG. 3B** shows a Western blot for protein expression of UPR markers BiP and CHOP in A498 and ACHN cells treated with the $EC_{50}$ doses of ChemBL375265, +/−OA supplementation.

FIG. 4 depicts the types of cancers in relation to levels of SCD1 gene expression found in patient tumors.

FIGS. 9A-9F show SCD1 expression profile in thyroid malignancy. (9A) Heatmap of fatty acid metabolism in ATC versus normal thyroid subject tissue samples. Black arrows indicate SCD1 and SCD5 expression. (9B) Results of QPCR for SCD1 mRNA expression in normal, FA, PTC, FTC, and ATC subject tissue samples. (9C) IHC expression of SCD1 in normal, FA, PTC, FTC, and ATC subject tissue samples quantitated using the H-score method as described in the Materials/Methods section. FTC samples are further sorted into low grade and high grade malignancy. (9D) TMN status of subject-derived cells used in this study. (9E) QPCR for SCD1 mRNA expression in normal, FA, PTC, FTC, and ATC subject-derived cells. (9F) Western blot analysis of SCD1 protein expression in normal, FA, PTC, FTC, and ATC subject-derived cells.

FIGS. 10A-10F show effects of pharmacologic SCD1 inhibition in thyroid cells. Proliferative dose response of thyroid cells to the SCD1 small molecule inhibitor A939572 in (10A) normal thyroid cells, (10B) FA cells, (10C) PTC cells, (10D) FTC cells, and (10E) ATC cells. (10F) Proliferative dose response of ATC cells to the small molecule SCD1 inhibitor MF-438. Results are presented as percent cell number relative to DMSO treated control.

FIG. 11A shows SCD1 inhibitor is rescued when oleic acid (OA) is added to A939572 treatment. In FIG. 11B, the same is shown but MF-438 is used as the SCD1 inhibitor. FIG. 11C-E shows SCD1 inhibitor induced ER stress and the UPR response in ATC cells. ER stress is induced by A939572 and not induced and blocked when oleic acid is added prior to A939572 treatment.

FIGS. 12A-12E show (12A) Mono-therapeutic dose response of carfilzomib in ATC cells. $EC_{50}$ values are listed. Combinatorial dose response of carfilzomib with (12B) A939572 or (12D) MF-438 in THJ29T and THJ16T cells are shown. (12C, 12E) Combination index values evaluating drug synergy generated using CalcuSyn software as described in the text in THJ29T and THJ16T cells.

FIGS. 13A-13E show the evaluation of combinatorial drug treatment on tumor cell proliferation. (13A) Mono-therapeutic dose response of bortezomib in ATC cells. $EC_{50}$ values are listed. Combinatorial dose response of bortezomib with (13B) A939572 or (13D) MF-438 in THJ29T and THJ16T cells. (13C, 13E) Combination index values evaluating drug synergy generated using CalcuSyn software as described in the text in THJ29T and THJ16T cells.

FIGS. 14A-14C show the evaluation of tumor cell viability in response to combinatorial therapy. Western blot for PARP cleavage and CHOP expression in THJ29T and THJ16T ATC cells treated with (14A) A939572 or (14B) MF-438 in combination with carfilzomib. (14C) Cell death analysis using flow cytometry sorting of propidium iodide stained cells treated with the EC50 dose of indicated drugs after a 48 hour treatment. Graphical results are shown, where (*) indicates a 5% or greater increase in cell death as compared to DMSO control, and (**) indicates a 5% or greater increase in cell death as compared to monotherapy.

FIGS. 15A-15C show the evaluation of tumor cell viability in response to combinatorial therapy. Western blot for PARP cleavage and CHOP expression in THJ29T and THJ16T ATC cells treated with (15A) A939572 or (15B) MF-438 in combination with bortezomib. (15C) Graphical results of cell death analysis using flow cytometry sorting of propidium iodide stained cells treated with the EC50 dose of indicated drugs after a 48 hour treatment, where (*) indicates a 5% or greater increase in cell death as compared to DMSO control, and (**) indicates a 5% or greater increase in cell death as compared to monotherapy.

FIGS. 17A-17G show the results of combinatorial therapy in an in vivo model of ATC. (17A) Mean THJ16T cell xenograft tumor volume of mice treated with MF-438 and carfilzomib independently or in combination. A treatment map depicting drug administration is included. (17B-17G) H&E staining was performed as well as ki67 (proliferative index), cleaved caspase 3 (CC3, apoptosis marker), CD31 (endothelial cell marker), HERPUD1 (ER stress marker), and Survivin (inhibitor of apoptosis, IAP family). Asterisks indicate statistically significant changes in IHC scores as compared to placebo control where p≤0.05.

FIG. 18A provides photographs showing immunohistochemistry staining using an antibody specific for SCD1 and shows elevated SCD1 in HCC (brown staining and bar graph). FIG. 18B provides the results of a Western Blot analysis technique where ten HCC cell lines were used to show variable expression of SCD1 protein with most showing elevated levels.

DETAILED DESCRIPTION

Figure 1:
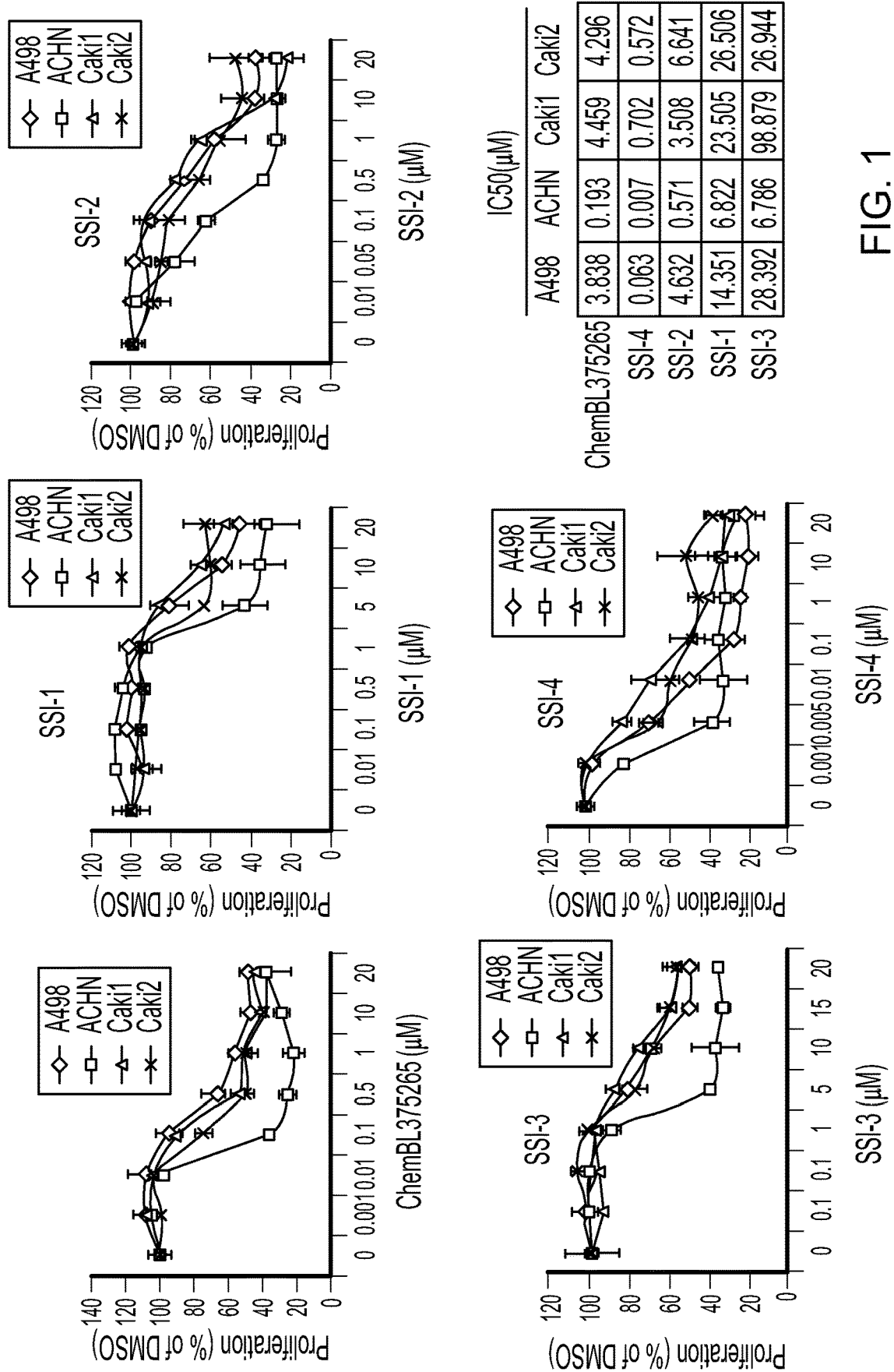
FIG. 1 shows the $EC_{50}$ values in four ccRCC cell lines of known (ChemBL375265) and SCD1 inhibitors generated using linear regression modeling.

SCD1 is an enzyme that catalyzes the de novo lipogenesis of Δ-9 monounsaturated fatty acids (MUFA) oleic acid (OA) and palmitoleic acid (PA). These MUFAs are essential for the synthesis of triglycerides, sphingolipids, ceramides, glycolipids, phospholipids, and other lipoproteins which influence membrane fluidity, membrane raft formation and receptor clustering, second messenger signaling, fatty acid oxidation, energy storage, cell division, inflammation, and a number of other biological functions (Guillou H, Zadravec D, Martin P G, Jacobsson A. The key roles of elongases and desaturases in mammalian fatty acid metabolism: Insights from transgenic mice. *Prog Lipid Res.* April 2010; 49(2): 186-199).

Aberrant upregulation of SCD1 has been implicated in the development of certain types of cancer, for example, renal cancer. Inhibitors of SCD1, compositions, and methods of use are provided in this disclosure.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "halo" refers to fluoro, chloro, bromo or iodo.

The term "alkyl" refers to a straight or branched chain alkyl group, having from 1-20 carbon atoms. The alkyl is unsubstituted unless otherwise indicated. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "$C_{x-y}$ alkyl" refers to an alkyl group between x and y carbon atoms in size. For example, $C_1$-8 alkyl refers to an alkyl of 1 to 8 carbon atoms.

The term "aryl" as used herein includes 5-, 6-, and 7-membered unsubstituted single-ring aromatic groups in which each atom of the ring is carbon. The term "aryl" also includes polycyclic ring systems having two cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. The aryl group may be optionally substituted where indicated. Aryl groups include benzene, naphthalene, tetralin, and the like.

The term "haloalkyl" refers to an alkyl group that is substituted with one or more (e.g., 1, 2, 3, 4, or 5) halo substituents. The group is otherwise unsubstituted unless as indicated. Examples include chloroethyl, chloromethyl, difluoromethyl, trifluoromethyl, and the like.

A "pharmaceutically acceptable carrier" refers to any pharmaceutically acceptable solvent, suspending agent, or other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, without limitation, water, saline solutions, dimethyl sulfoxide, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate).

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases.

Compounds

Provided herein are compounds according to Formula (I):

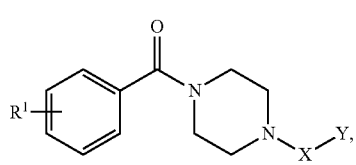

(I)

or a pharmaceutically acceptable salt thereof, wherein:

$R^1$ is an unsubstituted $C_{1-6}$alkyl or $C_{1-6}$haloalkyl;

X is

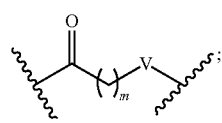

Y is selected from:

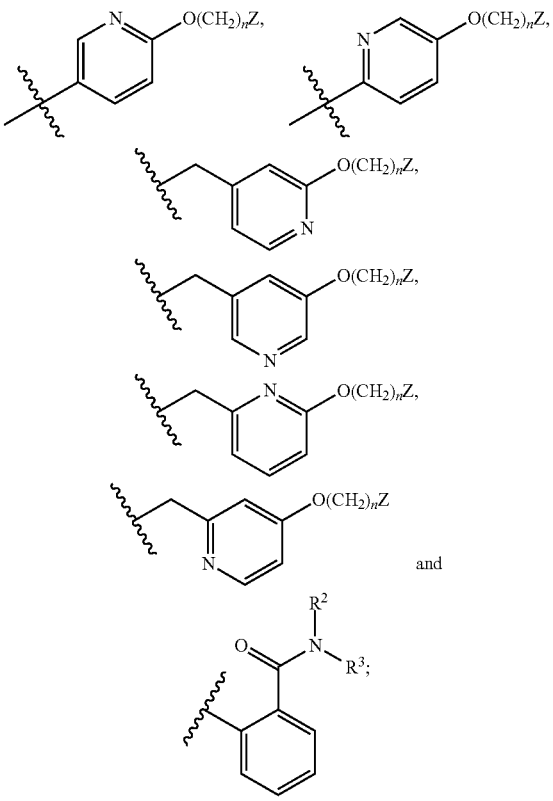

and m is 0 or 1;

n is 0, 1, or 2;

V is $NR^4$ or O;

$R^2$, $R^3$, and $R^4$ are each independently H or an unsubstituted $C_{1-6}$alkyl; and Z is an unsubstituted aryl.

In some embodiments, the compound according to Formula (I) has the structure of Formula (Ia):

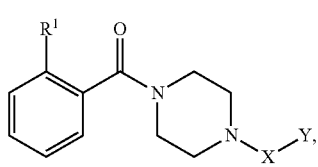

(Ia)

or a pharmaceutically acceptable salt thereof.

In some embodiments, V is $NR^4$. In some embodiments, V is NH. In some embodiments, V is O.

In some embodiments, X is

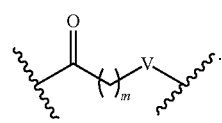

In some embodiments, Y is

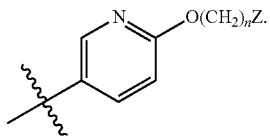

In some embodiments, Y is

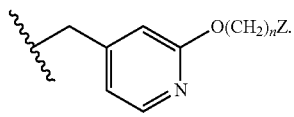

In some embodiments, Y is

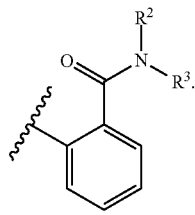

In some embodiments, Z is selected from the group consisting of: phenyl and naphthyl. For example, Z can be phenyl.

In some embodiments, m is 0. In some embodiments, m is 1.

In some embodiments, n is 0. In some embodiments, n is 1. In some embodiments, n is 2.

In some embodiments, $R^1$ is an unsubstituted $C_{1-6}$alkyl. In some embodiments, $R^1$ is an unsubstituted $C_{1-3}$alkyl. For example, $R^1$ can be $CH_3$. In some embodiments, $R^1$ is a $C_{1-6}$haloalkyl. In some embodiments, $R^1$ is a $C_{1-3}$haloalkyl. For example, $R^1$ can be $CF_3$.

In some embodiments, $R^2$ is an unsubstituted $C_{1-6}$alkyl. For example $R^2$ can be $CH_3$. In some embodiments, $R^2$ is H.

In some embodiments, $R^3$ is an unsubstituted $C_{1-6}$alkyl. For example $R^3$ can be $CH_3$. In some embodiments, $R^3$ is H.

In some embodiments, $R^4$ is an unsubstituted $C_{1-6}$alkyl. For example $R^4$ can be $CH_3$. In some embodiments, $R^4$ is H.

In some embodiments, $R^2$ is H; and $R^3$ is $CH_3$.

Non-limiting examples of a compound according to Formula (I) and/or Formula (Ia) include:

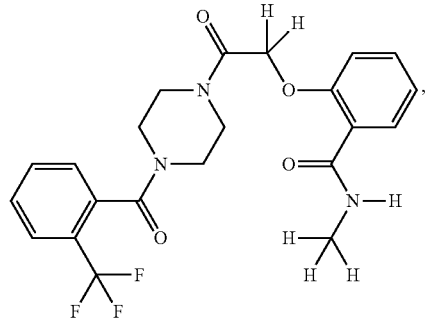

N-Methyl-2-(2-oxo-2-{4-[2-(trifluoromethyl)benzoyl]piperazin-1-yl}ethoxy)benzamide;

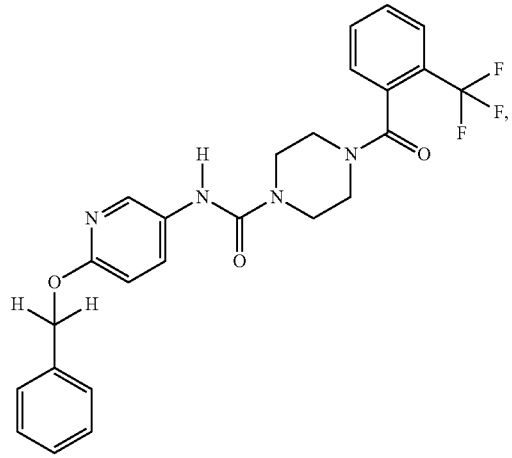

2-(benzyloxy)-5-{[hydroxy({4-[2-(trifluoromethyl)benzoyl]piperazin-1-yl})methyl]amino}-1,2-dihydropyridin-2-ylium-1-ide; and

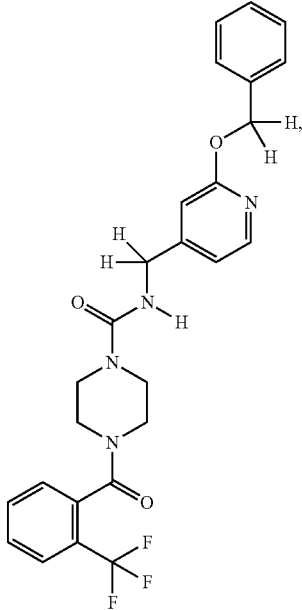

2-(benzyloxy)-4-({[hydroxy({4-[2-(trifluoromethyl)benzoyl]piperazin-1-yl})methyl]azanidyl}methyl)-1,2-dihydropyridin-2-ylium-1-ide, or a pharmaceutically acceptable salt thereof.

Also provided herein is a compound according to Formula (II):

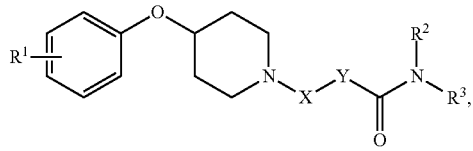

(II)

or pharmaceutically acceptable salt thereof,
wherein
$R^1$ is halo;
X is —(C=O)NR$^4$—;
Y is

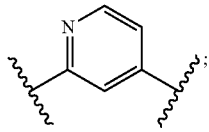 [SMILES: *c1ccnc(*)c1]

;

$R^2$, $R^3$, and $R^4$ are each independently H or an unsubstituted $C_{1-6}$alkyl.

In some embodiments, a compound according to Formula (II) has the structure of Formula (IIa):

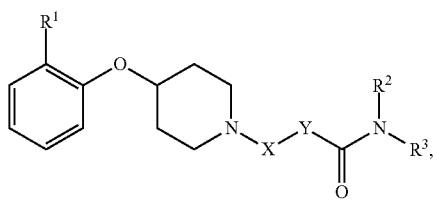

(IIa)

or pharmaceutically acceptable salt thereof.
In some embodiments, X is —(C=O)NR$^4$—.
In some embodiments, Y is

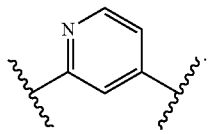 [SMILES: *c1ccnc(*)c1]

.

In some embodiments, $R^1$ is Cl. In some embodiments, $R^1$ is F.
In some embodiments, $R^2$ is an unsubstituted $C_{1-6}$alkyl. For example $R^2$ can be $CH_3$. In some embodiments, $R^2$ is H.
In some embodiments, $R^3$ is an unsubstituted $C_{1-6}$alkyl. For example $R^3$ can be $CH_3$. In some embodiments, $R^3$ is H.
In some embodiments, $R^4$ is an unsubstituted $C_{1-6}$alkyl. For example $R^4$ can be $CH_3$. In some embodiments, $R^4$ is H.
In some embodiments, $R^2$ is H; and $R^3$ is $CH_3$.

Non-limiting examples of a compound according to Formula (II) and/or Formula (IIa) include:

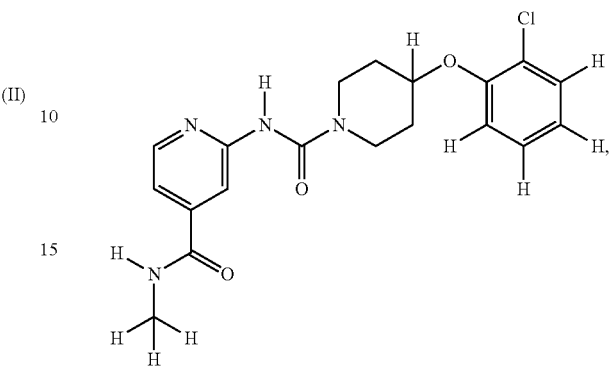

SSI-4

2-{[4-(2-Chlorophenoxy)piperidine-1-carbonyl]amino}-N-methylpyridine-4-carboxamide,
or pharmaceutically acceptable salt thereof.

Administration

Compounds as described herein can be administered in various forms, depending on the disorder to be treated and the age, condition, and body weight of the subject, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the subject, the nature and severity of the disorder to be treated or prevented, the route of administration and the form of the drug, in general, a daily dosage of from 0.01 to 2000 mg of the compound is recommended for an adult human subject, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the subject (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In solid dosage forms for oral administration (capsules, tablets, pills, dragées, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragées, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Methods of Use

This disclosure provides methods for treating cancer, for example, renal cell carcinoma, ovarian, breast, prostate, colon, pancreatic, bladder, liver, lung, thyroid cancers, and melanoma. In some embodiments, this document provides methods and material for using a compound of the disclosure to treat cancer (e.g., clear cell renal cell carcinoma (ccRCC), hepatobiliary carcinoma (HCC), and anaplastic thyroid cancer) or to increase the efficacy of a cancer treatment. In some embodiments, the cancer is associated with overexpression of an SCD1 protein, an SCD1 enzyme (e.g., "a SCD1-associated cancer") (see, e.g., von Roemeling, C. A. et al. *J. Clin. Endocrinol. Metab.* (May 2015) 100(5): E697-E709). The term "SCD1-associated cancer" as used herein refers to cancers associated with or having a dysregulation of a SCD1 protein (SCD1 enzyme), or expression or activity or level of the same. Non-limiting examples of a SCD1-associated cancer are described herein.

Accordingly, provided herein are methods for treating a patient diagnosed with (or identified as having) a cancer (e.g., a SCD1-associated cancer) that include administering to the patient a therapeutically effective amount of a compound provided herein or a pharmaceutically acceptable salt thereof. Also provided herein are methods for treating a patient identified or diagnosed as having a SCD1-associated cancer (e.g., a patient that has been identified or diagnosed as having a SCD1-associated cancer through the use of a regulatory agency-approved, e.g., FDA-approved test or assay for identifying dysregulation of a SCD1 protein, or expression or activity or level of the same, in a patient or a biopsy sample from the patient) (e.g., any of the SCD1-associated cancer described herein or known in the art) that include administering to the patient a therapeutically effective amount of a compound provided herein or a pharmaceutically acceptable salt thereof. In some embodiments, the test or assay is provided as a kit.

Also provided are methods for treating cancer in a patient in need thereof, the method comprising: (a) determining if the cancer in the patient is a SCD1-associated cancer (e.g., using a regulatory-agency approved, e.g., FDA-approved, kit for identifying dysregulation of a SCD1 protein or expression or activity or level of the same, in a patient or a biopsy sample from the patient); and (b) if the cancer is determined to be a SCD1-associated cancer, administering to the patient a therapeutically effective amount of a compound provided herein or a pharmaceutically acceptable salt thereof.

Also provided are methods of treating a patient (e.g., a patient suspected of having a SCD1-associated cancer, a patient presenting with one or more symptoms of a SCD1-associated cancer, or a patient having an elevated risk of developing a SCD1-associated cancer) that include performing an assay (e.g., an assay that utilizes next generation sequencing, pyrosequencing, immunohistochemistry, or break apart FISH analysis) (e.g., using a regulatory agency-approved, e.g., FDA-approved kit) on a sample obtained from the patient to determine whether the patient has dysregulation of a SCD1 protein or expression or activity or level of the same, and administering (e.g., specifically or selectively administering) a therapeutically effective amount of a compound provided herein or a pharmaceutically acceptable salt thereof to a patient determined to have dysregulation of a SCD1 protein or expression or activity or level of the same. Additional assays, non-limiting assays that may be used in these methods are described herein. Additional assays are also known in the art.

In some embodiments of any of the methods or uses described herein, an assay used to determine whether the patient has dysregulation of a SCD1 protein or expression or activity or level of any of the same, using a sample (e.g., a biological sample or a biopsy sample (e.g., a paraffin-embedded biopsy sample) from a patient (e.g., a patient suspected of having a SCD1-associated cancer, a patient having one or more symptoms of a SCD1-associated cancer, and/or a patient that has an increased risk of developing a SCD1-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a SCD1 protein or expression or activity or levels of any of the same.

In some embodiments, the subject is a mammal. In some embodiments, the mammal can be a mouse, a rat, a guinea pig, a dog, a cow, a goat, a monkey, or a human. For example, the mammal can be a cynomolgus monkey. In some embodiments, the mammal can be a human.

As described herein, one or more (e.g., one, two, three, four, or more) compounds of the disclosure can be administered to a mammal (e.g., a human) having cancer (e.g., a SCD1-associated cancer, renal cancer, liver cancer, thyroid cancer) under conditions wherein the number of cancer cells within the mammal is reduced. In some embodiments, one or more (e.g., one, two, three, four, or more) compounds of the disclosure can be administered to a mammal (e.g., a human) having renal cancer (e.g., ccRCC) under conditions wherein the number of renal cancer cells within the mammal is reduced.

An SCD1 enzyme can be a humSCD1 having the amino acid sequence set forth in GenBank® Accession No. 000767 (GI No. 21431730) or a humSCD1 encoded by nucleic acid having the nucleic acid sequence set forth in GenBank® Accession No. AF097514.1 (GI No. 4808600). Examples of inhibitors of an SCD1 include, without limitation, inhibitory anti-SCD1 antibodies, siRNA molecules, shRNA molecules, nucleic acid vectors designed to express siRNA or shRNA molecules, anti-sense molecules, and small molecule antagonists such as A939572 (Biofine International Inc., Urvashi et al., *Mol. Cancer Res.*, 9:1551 (2011); Bristol-Myers Squibb R&D, Roongta et al., *Mol. Cancer Res.*, 9(11):1551-61 (2011)), MK-8245 (Merck Research Laboratories, Oballa et al., *J. Med. Chem.*, 54(14):5082-96 (2011)), CVT-11127, MF-152 (Merck, Li et al., *Bioorganic & Medicinal Chemistry Letters*, 19:5214 (2009)), LCF369, CVT-11,563, CVT-12,012, DSR-4029, and GSK993 (Uto et al., *Eur. J. Med. Chem.*, 45:4788-4796 (2010)), MF-438 (Leger, S. et al., *Bioorg Med Chem Lett.* 20(2):499-502 (2010)), and HYR-061 (Medchem Express, Koltun et al., *Bioorganic & Medicinal Chemistry Letters*, 19(7):2048-2052 (2009), and Xin et al., *Bioorganic & Medicinal Chemistry Letters*, 18(15):4298-4302 (2008)). In some cases, an inhibitor of an SCD1 polypeptide can be an inhibitor described elsewhere (Igal, *Carcinogenesis*, 31(9):1509-1515 (2010); Oballa, *J. Med. Chem.*, 54:5082-5096 (2011); Li et al., *Bioorganic & Medicinal Chemistry Letters*, 19:5214-5217 (2009); Uto et al., *Eur. J. Med. Chem.*, 46:1892-1896 (2011); Uto et al., *Eur. J. Med. Chem.*, 45:4788-4796 (2010); Liu, G. *Expert Opin Ter Pat*, 19(9):1169-91 (2009); Powell, D. A., *Bioorg Med Chem Lett.* 20(22):6366-9 (2010), Mason P, et al., *PLoS ONE* 7(3): 33823 (2012), and Roongta et al., *Mol. Cancer Res.,* 9:1551-1561 (2011)).

In some embodiments, the methods for inhibiting an SCD1 enzyme can be performed in a cell. In some embodiments, the method comprises inhibiting an SCD1 enzyme in a cell with an effective amount of a compound, pharmaceutically acceptable salt, or a pharmaceutical composition thereof, as described herein. The cell can be a cancer cell, for example, a kidney cancer cell, a liver cancer cell, a breast cancer cell, a lung cancer cell, a pancreatic cancer cell, a bladder cancer cell, a colon cancer cell, a melanoma cell, a thyroid cancer cell, an ovarian cancer cell, or a prostate cancer cell. For example, the cancer cell can be a kidney cancer cell. In some embodiments, the contacting is in vitro. For example, the method for inhibiting the SCD1 enzyme can be used in an in vitro ELISA assay. In some embodiments, the contacting is in vivo. For example, the method for inhibiting the SCD1 enzyme can be used in an in vivo rat model or in treating a cancer in a subject as described herein.

Cancers that may be treated by an inhibitor of SCD1, compositions and methods described herein include, but are not limited to, the following:

Breast cancers, including, for example $ER^+$ breast cancer, $ER^-$ breast cancer, $her2^-$ breast cancer, her2+ breast cancer, stromal tumors such as fibroadenomas, phyllodes tumors, and sarcomas, and epithelial tumors such as large duct papillomas; carcinomas of the breast including in situ (non-invasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score;

Hematopoietic cancers, including, for example, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sézary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, and myeloma bone disease;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

kidney (renal) cancers, including, for example, clear cell renal cell carcinoma, papillary renal cell carcinoma, chromophobe renal cell carcinoma, collecting duct renal cell carcinoma, unclassified renal cell carcinoma, transitional cell carcinoma, and renal sarcoma;

bladder cancers, including, for example, transitional cell carcinoma, urothelial carcinoma, papillary carcinoma, flat carcinoma, squamous cell carcinoma, adenocarcinoma, small-cell carcinoma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, epithelial cancer, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis;

thyroid cancers, including, for example, papillary thyroid cancer, follicular thyroid cancer, anaplastic thyroid carcinoma, and medullary thyroid cancer; and adrenal gland cancers, including, for example, neuroblastoma.

In some cases, one or more (e.g., one, two, three, four, or more) compounds of the disclosure can be used as described herein to treat cancer, including renal cancer, ovarian, breast, prostate, colon, pancreatic, bladder, liver, lung, and thyroid cancer as well as melanoma. In some embodiments, the cancer is a kidney cancer or a bladder cancer. For example, the cancer can be a kidney cancer. In some embodiments, the cancer is a bladder cancer. In some embodiments, the cancer is a liver cancer such as hepatocellular carcinoma. In some embodiments, the cancer is a thyroid cancer such as anaplastic thyroid carcinoma.

For example, a subject having cancer can be administered one or compounds of the disclosure under conditions that result in reduced tumor size or stable disease. In some cases, one or more (e.g., one, two, three, four, or more) compounds of the disclosure can be used as described herein to increase the efficacy of a cancer treatment. In some embodiments (e.g., when compositions comprising one or more (e.g., one, two, three, four, or more) compounds of the disclosure are administered in conjunction with another anticancer agent), one can create a synergistic effect among the agents administered and thereby improve the outcome for a subject. In some embodiments, one or more (e.g., one, two, three, four, or more) compounds of the disclosure (or a pharmaceutically acceptable salt form thereof) can be administered in combination with (i.e., before, during, or after) administration of a pain relief agent (e.g., a nonsteroidal anti-inflammatory drug such as celecoxib or rofecoxib), an antinausea agent, or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine, oxaliplatin/5 FU, abiraterone, letrozole, 5-aza/romidepsin, or procarbazine). In certain embodiments, the anticancer agent is paclitaxel or docetaxel. In other embodiments, the anticancer agent is cisplatin or irinotecan.

For example, a subject having ccRCC can be administered one or more compounds of the disclosure under conditions that result in reduced tumor size or stable disease. In some cases, one or more (e.g., one, two, three, four, or more) compounds of the disclosure can be used as described herein to increase the efficacy of a renal cell carcinoma treatment (i.e. administered in combination with one or more renal cell carcinoma treatments). Examples of such renal cell carcinoma treatments include, without limitation, treatment with Nexavar®, Sutent®, Torisel®, Afinitor® (everolimus), axitinib, pazopanib, levatinib, interleukin-2, and combinations thereof.

In some embodiments, one or more compounds provided herein can be administered to a subject having a thyroid cancer (e.g. anaplastic thyroid carcinoma, or a SCD1-associated thyroid cancer). In some cases, the one or more compounds provided herein can be administered in combination with one or more proteasome inhibitors. Exemplary proteasome inhibitors include lactacystin, bortezomib, dislfiram, salinosporamide A, carfilzomib, ONX0912, CEP-18770, MLN9708, epoxomicin, and MG132). In some embodiments, the combination of a compound provided herein (e.g., SSI-4) and a proteasome inhibitor have a synergistic effect on the treatment of the cancer.

In some embodiments, one or more compounds provided herein can be administered to a subject having a liver cancer (e.g. hepatobiliary carcinoma (HCC), or a SCD1-associated liver cancer). In some cases, the one or more compounds provided herein can be administered in combination with one or more multikinase inhibitors (e.g., tyrosine kinase inhibitors, RAF kinase inhibitors, serine/threonine kinase inhibitors). In some embodiments, the multikinase inhibitor is sorafenib. In some embodiments, the combination of a compound provided herein (e.g., SSI-4) and sorafenib have a synergistic effect on the treatment of the cancer.

In some cases, one or more (e.g., one, two, three, four, or more) compounds of the disclosure as described herein can be used in combination with one or more (e.g., one, two, three, four, or more) inhibitors of mammalian target of rapamycin (mTor). Non-limiting examples of mTor inhibitors include: sirolimus (RAPAMUNE®), temsirolimus (CCI-779), everolimus (RAD001), ridaforolimus (AP-23573).

Accordingly, provided herein is a method for reducing the number of cancer cells within a subject, wherein the method comprises administering, to the subject, a compound of the disclosure and an inhibitor of an mTor polypeptide under conditions wherein the number of viable cancer cells present within said subject is reduced. In some embodiments, the one or more mTor inhibitor can include a standard of care drug for a particular cancer cell type. For example, a compound of the disclosure can be administered with paclitaxel and/or platin (cisplatin, carboplatin, or oxaliplatin) for the treatment of ovarian cancer. In some embodiments, the following standard of care drugs can be combined with an SCD1 inhibitor for the following cancers:

Lung—paclitaxel, nivolumab, ceritinib, afatinib
Colon—capecitabine
Breast
    Metastatic breast—capecitabine, paclitaxel, and/or gemcitabine
    Hormonally responsive breast—aromatase inhibitors such as letrazole and/or antiestrogens such as tamoxifen
    HER2 positive—Her2 inhibitors such as trastuzumab; palbociclib, ado-trastuzumab emtansine
Melanoma—temozolomide, and/or BRAF inhibitors, pembrolizumab, nivolumab, pomalidomide, dabrafenib
Prostate—androgen receptor inhibitors such as abiraterone
Bladder—gemcitabine and/or paclitaxel
Thyroid—paclitaxel, cisplatin, a proteasome inhibitor, sorafenib, lenvatinib
Pancreatic—gemcitabine
Liver—sorafenib
Mantle cell lymphoma—bortezomib
Multiple myeloma—panobinostat
    Relapsed and/or refractory—carfilzomib, bortezomib and/or an immunomodulatory agent such as dexamethasone In some embodiments, the combination of one or more compounds of the disclosure and one or more inhibitors of mTor exhibit a synergistic response. In some embodiments, the one or more inhibitors of an SCD1 (i.e. one or more compounds of the disclosure) can be administered before, during, or after administration of the one or more inhibitors of mTor.

In some cases, one or more (e.g., one, two, three, four, or more) inhibitors of an SCD1 enzyme as described herein can be used in combination with one or more (e.g., one, two, three, four, or more) proteasome inhibitors. Non-limiting examples of proteasome inhibitors include marizomib (NPI-0052), bortezomib (Velcade), and carfilzomib (Kyprolis®). Other suitable proteasome inhibitors can be found in U.S.

Pat. Nos. 8,431,571; 8,357,683; 8,088,741; 8,080,576; 8,080,545; 7,691,852; 7,687,456; 7,531,526; 7,109,323; 6,699,835; 6,548,668; 6,297,217; 6,066,730, and published PCT applications WO 2011/123502; WO 2010/036357; WO 2009/154737; WO 2009/051581; WO 2009/020448, each of which is incorporated by reference in its entirety.

Accordingly, provided herein is a method for reducing the number of cancer cells within a mammal, wherein the method comprises administering, to the mammal, inhibitors of an SCD1 enzyme and a proteasome inhibitor under conditions wherein the number of viable cancer cells present within said mammal is reduced. In some embodiments, the one or more proteasome inhibitors can include a standard of care drug for a particular cancer cell type. For example, an SCD1 inhibitor can be administered with carfilzomib for the treatment of refractory multiple myeloma.

In some embodiments, the combination of one or more inhibitors of an SCD1 enzyme and one or more proteasome inhibitors exhibit a synergistic response. In some embodiments, the one or more inhibitors of SCD1 (i.e. one or more compounds of the disclosure) can be administered before, during, or after administration of the one or more proteasome inhibitors. The administration can be an intratumoral, oral, intraperitoneal, intramuscular, or intravenous administration. In some embodiments, the SCD1 inhibitor and the proteasome inhibitor are admixed prior to administration.

A compound of the disclosure can also be administered to a subject in combination with surgical methods to treat cancers, e.g., resection of tumors. The compound can be administered to the individual prior to, during, or after the surgery. The compound can be administered parenterally, intravenous or injected into the tumor or surrounding area after tumor removal.

Typically, one or more of the compounds provided herein can be formulated into a pharmaceutical composition that can be administered to a mammal (e.g., rat, dog, horse, cat, mouse, rabbit, pig, cow, monkey, or human). For example, SSI-1 or a pharmaceutically acceptable salt thereof can be in a pharmaceutically acceptable carrier or diluent. The invention will be further described in the following examples, which do not limit the scope of the invention described in the claims.

EXAMPLES

Computational Methods

Example 1— De Novo Ligand Generation

Using methodology of combining multiple data sources for an accelerated drug discovery process, multiple new compounds using core generation were generated. First, all the cores were separated ("core separation") from each known scaffold, leaving the binding features from the edges of each compound. Then, potential core fragments were combined from varied sources (core libraries, in-house fragment libraries, and de novo scaffold manipulations), which are then inserted back into the core slots ($Core_1$, $Core_2$, or $Core_3$). Each new core is fused with the existing chemistry on the edges and placed into the appropriate pool ($pool_1$, $pool_2$, or $pool_3$). Each pool is filtered using energy minimization, correct bond orders, and ligand preparation with LigPrep. These three pools are then combined into a common de novo ligand pool. The entire pool of ligands is expanded to allow for generation of tautomers where appropriate, ionization states over a valid range of pH values, and isomerizations. Reactive functional groups are screened and removed from the dataset. At this point, Z-scoring filtering is applied as a reductive filter for SCD1 specificity.

Shape Fitting Algorithms

Shape similarity models were generated for each compound versus the known inhibitor, SAR707 or A939572, such that upon superposition of the known compound (A) and the de novo compound (B), the following measurement for jointly occupied volume $V_{A \cap B}$ is obtained, which is normalized by the total volume $V_{A \cup B}$, thus giving the normalized shape similarity Sim ranging from 0 to 1. Thus $Simm_{AB} = V_{A \cap B}/V_{A \cup B}$, where A is the known inhibitor SAR707 or A939572 and B is the unknown, de novo compound, were computed for 1000s of generated compounds. Finally, a pairwise method was employed for faster calculations (600 conformers per second) (Sastry, G. M. et al. *J. Chem. Inf. Model.* 2013; 53:1531-1542; Pala, D. et al. *J. Chem. Inf. Model.* 2013; 53(4):821-835; Kalid, O. et al. *J. Comput. Aided Mol. Des.* 2012; 26:1217-1228; Fu, J. et al. *Bioorg. Med. Chem. Lett.* 2012; 22(2):6848-6853; Sastry, G. M. et al. *J. Chem. Inf. Model.* 2011; 51:2455-2466). Each compound is allowed to generate 500 conformers, retaining 20 conformers per rotatable bond, allowing the amide bonds to vary conformation, to maximize shape matching likelihood. Volume was also computed for both Pharmacophore types and Atom types using the Macromodel definition for atom typing. Four alignments per ligand were used, filtering out conformers with similarity below 0.7 and then compiled all the shape data together selecting the top shape matching compounds for retention and excluding all lower scoring hits. Various models for chemical shape can also be employed to screen both shape and chemical information simultaneously.

Computational Docking

Initial docking was performed using Glide (v. 5.6) within the Schrödinger software suite (Schrödinger, LLC) (Mohamadi, F. et al. *J Comput Chem.* 1990; 11(4):440-467). The origin of the compounds is described in *De Novo Library Design*. The starting conformation of ligands was obtained by the method of Polak-Ribière conjugate gradient (PRCG) energy minimization with the Optimized Potentials for Liquid Simulations (OPLS) 2005 force field (Jorgensen, W L et al. *J Am Chem Soc. Mar.* 16, 1988; 110(6):1657-1666) for 5000 steps, or until the energy difference between subsequent structures was less than 0.001 kJ/mol-Å units. The docking methodology has been described previously (Caulfield, T. et al. *Proteins. November* 2012; 80(11):2489-2500; Loving, K. et al. *Journal of computer-aided molecular design. August* 2009; 23(8):541-554; Vivoli, M. et al. *Mol Pharmacol. March* 2012; 81(3):440-454), and the scoring function utilized is described elsewhere (Friesner, R A et al. *Journal of medicinal chemistry.* Oct. 19, 2006; 49(21):6177-6196).

Molecular Modeling of SCD1

Molecular models were generated for the human protein stearoyl-CoA desaturase 1, or acyl-CoA desaturase (SCD1) (NP_005054.3), which has the following 359 amino acid protein sequence:

(SEQ ID NO: 1)
MPAHLLQDDISSSYTTTTTITAPPSRVLQNGGDKLETMPLYLEDDIRPD

IKDDIYDPTYKDKEGPSPKVEYVWRNIILMSLLHLGALYGITLIPTCKF

YTWLWGVFYYFVSALGITAGAHRLWSHRSYKARLPLRLFLIIANTMAFQ

NDVYEWARDHRAHHKFSETHADPHNSRRGFFFSHVGWLLVRKHPAVKEK

-continued

GSTLDLSDLEAEKLVMFQRRYYKPGLLMMCFILPTLVPWYFWGETFQNS

VFVATFLRYAVVLNATWLVNSAAHLFGYRPYDKNISPRENILVSLGAVG

EGFHNYHHSFPYDYSASEYRWHINFTTFFIDCMAALGLAYDRKKVSKAA

ILARIKRTGDGNYKSG.

The modeling for this protein was completed using three combined methods, Schrodinger Prime modeling, TASSER, and Yasara structural and homology modeling program (Krieger E, Dunbrack R L, Jr., Hooft R W, Krieger B. Assignment of protonation states in proteins and ligands: combining pKa prediction with hydrogen bonding network optimization. *Methods Mol Biol.* 2012; 819:405-421; Krieger E, Joo K, Lee J, et al. Improving physical realism, stereochemistry, and side-chain accuracy in homology modeling: Four approaches that performed well in CASP8. *Proteins.* 2009; 77 Suppl 9:114-122; Prime, version 2.1 [computer program]. Schrodinger, LLC, New York, N.Y. 20092014; Zhou H, Skolnick J. Protein structure prediction by pro-Sp3-TASSER. *Biophys J.* Mar. 18, 2009; 96(6):2119-2127; Zhou H, Skolnick J. Improving threading algorithms for remote homology modeling by combining fragment and template comparisons. *Proteins.* July 2010; 78(9):2041-2048; Zhou H, Skolnick J. Template-based protein structure modeling using TASSER(VMT). *Proteins.* Sep. 14, 2011).

Several models were generated and compared for hybrid modeling, which resulted in best scoring portions from each program and validated for dihedrals, packing, and other metrics like Phi-Psi space.

From these final models for SCD1 were mapped using the SiteMap module to score highest confidence binding sites on SCD1, which resulted in a deep internal pocket that would correspond with lipophilic substrate binding, required for stearoyl-coA binding (Schrödinger Suite 2014 [computer program]. BioLuminate, version 1.0. New York, N.Y.: Schrödinger, LLC; 2014; Halgren T. New method for fast and accurate binding-site identification and analysis. *Chem. Biol. Drug Des.* 2007; 69(146-148); Halgren T. Identifying and characterizing binding sites and assessing druggability. *J. Chem. Inf. Model.* 2009; 49:377-389).

Prior to mapping out potential grid surfaces for an active site region surrounding residues, the ProteinPreparationWizard contained in Schrödinger (*Protein Preparation Wizard; Epik version 2.8; Impact version 6.3; Prime version 3.5* [computer program]: Schrödinger, LLC, New York, N.Y., USA; 2014) was used. The top regions identified using SiteMap region were then mapped for grid generation and decomposition of the protein's three-dimensional space for docking experiments. Using this grid, initial placement for A939572, SAR707, and other known inhibitors were docked using the Glide algorithm within the Schrodinger suite as a virtual screening workflow (VSW). The docking was accomplished using a scheme that proceeds from single-precision (SP) through extra-precision (XP) with the Glide algorithm (Glide, v. 5.6, Schrödinger, LLC). The top seeded poses were ranked for best scoring pose and unfavorable scoring poses were discarded. Each conformer was allowed multiple orientations in the site. Site hydroxyls, such as in serines and threonines, were allowed to move with rotational freedom. Docking scores were not retained as useful, since covalent bonding is the outcome. Hydrophobic patches were utilized within the virtual screening workflow (VSW) as an enhancement. Top favorable scores from initial dockings of yielded thousands of poses with the top five poses retained. XP descriptors were used to obtain atomic energy terms like hydrogen bond interaction, electrostatic interaction, hydrophobic enclosure and pi-pi stacking interaction that result during the docking run. VSW docking was completed for all novel generated compounds from the de novo design process described in the QSAR section and the docking utilized both hydrophobic constraints and the seeding generated from known inhibitor docking poses. Molecular modeling for importing and refining the known inhibitor compounds and generation of the small molecule compounds were prepared with LigPrep module (LigPrep 2.2 [computer program]. Schrodinger, LLC, New York, N.Y., 2008: Schrödinger; 2010). All image rendering used for figures was completed with Maestro (Maestro 9.4 [computer program]. New York, N.Y.: Schrödinger, LLC; 2014).

Example 2— QSAR Methods

Active, Inactive, Unknown Ligand Preparation

Twenty active compounds that ranged from 3 nM to 400 nM and eight inactives ranging from 2.68 micromolar to >10 micromolar were built into our pharmacophore modeling system. Conformers were generated for all actives, inactives, and test set compounds using ConfGen and Mixed MCMM/LCMOD within Schrodinger (Watts K S, Dalal P, Murphy R B, Sherman W, Friesner R A, Shelley J C. ConfGen: A Conformational Search Method for Efficient Generation of Bioactive Conformers. *J. Chem. Inf. Model.* 2010; 50:534-546). For ConfGen the number of conformers per rotatable bond was set at 100, maximum number of conformers per structure was set at 1000, sampling was set on "Thorough" mode and included preprocess minimization of 100 steps and postprocess minimization of 50 steps and eliminate high-energy/redundant conformers. The MacroModel options for conformer generation used the OPLS2005 force field, GB/SA water solvation treatment and default setting for the maximum relative energy difference and maximum allowed atom deviation.

Pharmacophore Hypothesis Generation

A common pharmacophore was determined over a variant list that ranged from 5-6 sites and required a match from at least 6 of the 17 actives built into the model. The variant list included 187 selections based on sites created for all the actives chosen. The following letter code was used for the pharmacophore sites/features: hydrogen bond acceptor (A), hydrogen bond donor (D), hydrophobic group (H), negatively charged group (N), positively charged group [P], aromatic ring [R], and no custom features for X, Y, or Z designation were assigned. For images with pharmacophore models, the following appearance is given: (A) is light red sphere located at atom with lone pair and arrow point toward the lone pair, (D) is light blue sphere centered on hydrogen atom with arrow in direction of the potential H-bond, (H) is green sphere, (N) is red sphere, [P] is blue sphere, and [R] is orange torus in plane of aromatic ring. Our search method employed for finding common pharmacophores is identified using a tree-based partitioning technique that groups according to inter-site distances (k-points). Using a binary decision tree, a tree depth of five was allowed and partition into bins based on a 2.0 Å width, while partition continues to either eliminate or survive the procedure.

Variant motifs that were included were AAAAAA, AAAAAD, AAAAAH, AAAAAR, AAAADD, AAAADH, AAAADR, AAAAHH, . . . , HNPRRR, which resulted in the following top variant hypotheses AAAHHR, AAAHRR, AAHHRR with 45, 1, and 57 maximum hypotheses, respectively. The initial pharmacophore modeling considered >20, 000 hypotheses. Actives were scored using vector and site filtering to keep RMSD below 1.200 Å, keep vectors with scores above 0.500, keep the top 30%, keep at least 10 and at most 50 using feature matching tolerances of A 1.00, D 1.00, H1.50, N 0.75, P 0.75, R 1.50, X 1.0, Y 1.0, and Z 1.0. The unweighted survival score formula is 1.0*(vector score)+1.0*(site score)+1.0*(volume score)+1.0–(number of matches–1), however to take advantage of existing active compounds, the adjusted scoring function is 1.0*(vector score)+1.0*(site score)+1.0*(volume score)–0.001*(reference ligand(s) relative conformational energy)+1.0–(number of matches 1)–0.001*(reference ligand activity).

This scoring metric resulted in eight qualified hypotheses for further examination, including: AAHHRR.2632, AAHHRR.2667, AAHHRR.2641, AAHHRR.2669, AAAHHR.5952, AAHHRR.2361, and AAAHHR.5952. All hypotheses had actives scored, inactives scored, then rescored for post-hoc analysis, which has the following formula: 1.0*(vector score)+1.0*(site score)+1.0*(volume score)+1.0–(number of matches–1)–0.001*(reference ligand relative conformational energy)+0.001*(reference ligand activity). Then the "adjusted survival score" becomes the survival score–1.0*(inactive match score).

The scoring hypotheses were bases on the identified pharmacophores from each surviving n-dimensional box for the chosen actives and additional information from partial matching of ligand alignments. The quality alignments were determined using three metrics, namely, the alignment score (via root-mean-squared-deviation (RMSD)), vector score (average cosine of the angles formed by corresponding pairs of vector features (A, D, R), and volume score (overlap of van der Waals models of non-hydrogen atoms in each pair of structures). As well, site scores for each alignment were computed to augment the alignment score with a cutoff Calign, which combined the site score, vector score, and volume score with separate weights to yield a combined alignment score for each non-reference pharmacophore that was aligned with reference. All pharmacophores within a box were treated as a reference and the highest one selected as a hypothesis during multi-ligand alignment optimization. The final scoring function (survival score) was:
$S = W_{site}S_{site} + W_{vec}S_{vec} + W_{vol}S_{vol} + W_{sel}S_{sel} + W_{rew}{}^m - W_E \Delta E + W_{act}{}^A$, where W's represented the weights and S's represented the scores. Inactives were penalized by adjusting their alignment score, such that, when an inactive matches only k out of n sites, an effective n-point alignment score was computed as follows: $S_{align,n} = \sqrt[n]{W_k S_{align,k}^2 + (1-W_k)C_{align}^2}$, where $W_k = k/n$. The final adjusted score mentioned above became $S_{adjusted} = S_{actives} - W_{inactives}S_{inactives}$. Default weights were used with all equations, as shown above. Hypotheses were clustered for to tease out pharmacophore model variants with similar scores.

Generation of 3D QSAR Models

The 3D QSAR models were built by mapping the chemical features of ligand structures onto a cubic three-dimensional grid space with the smallest grid spacing of 1 Å per side. As above, the ligands are first aligned to the set of pharmacophore features for the selected hypothesis using a standard least-squares approach, which utilizes regression of the independent variables with binary-valued bits in the cubes by structural components and the dependent variables are the activities. The regression was performed via a partial least squares (PLS) method, where a series of models generated with increasing number of PLS factors. T-value filter (t-value <2.0) was used to eliminate independent variables overly sensitive to incremental changes from the training set. For structural components, both atom-based and pharmacophore features based were examined. The regression with m PLS factors, fitted to activities is given as:

$$\hat{y} = \mu^y + \sum_{i=1}^{m} b_i t_i,$$

where m=number of PLS factors, b is regression coefficient, vector y represents activity values in the training set. For the prediction of activities for the new ligands, the following was used:

$$\hat{y} = \mu^y + \sum_{i=1}^{m}(X_{k,i} - \mu_i^x)b_i^x,$$

where k=1, . . . , $n_T$. Models with high stability were preferred.

Z-Score Matrix

A final Z-filtering mechanism was applied to reduce the dataset to a few select compounds for synthesis and experimental screening by using combined normalized scoring. The final Z-score for each compound was determined as:

$$Z_{scr} = \frac{(Shape_{norm} + Dock_{norm} + QSAR_{norm})}{3},$$

which averages average of the sums the normalization of each individual Shape, the Dock, and 3D-QSAR score De Novo Compounds Shape Scoring with SAR707

Figure 2A:
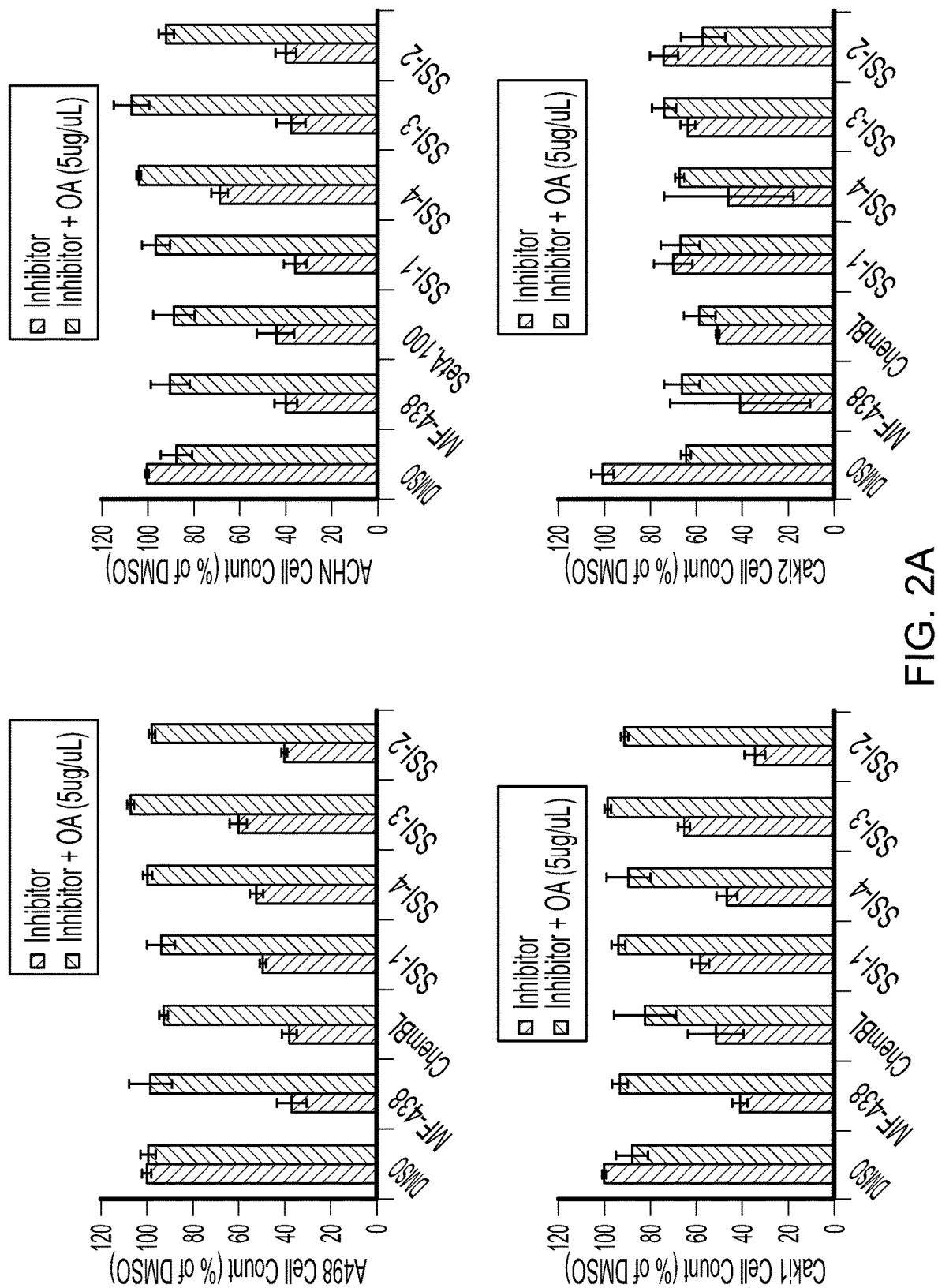
FIGS. 2A-2B show the analysis of SCD1 specificity using OA rescue assay.

SAR707 resulted in the best yield in shape matching with our generated de novo ligands (FIG. 2A). These de novo ligands were decomposed from A939572, MF-238 and SAR707, which had the cores stripped away and only the periphery edges retained. The best fitting SCD1 de novo compound, SSI-2, had a shape score of 88.1%. Top inhibitor shape scores were 0.881, 0.803, 0.660, and 0.642, for SSI-2, SSI-3, SSI-4 and SSI-1, respectively.

De Novo Compounds Docked with SCD1

Over 500 top generated compounds using scaffold/core hopping technologies were docked with SCD1 protein (Sun H, Tawa G, Wallqvist A. Classification of scaffold-hopping approaches. *Drug discovery today.* April 2012; 17(7-8):310-324; Ruddigkeit L, Blum L C, Reymond J L. Visualization and virtual screening of the chemical universe database GDB-17. *J Chem Inf Model.* Dec. 23, 2012; Sperandio O, Andrieu O, Miteva M A, et al. MED-SuMoLig: A New Ligand-Based Screening Tool for Efficient Scaffold Hopping. *Journal of Chemical Information and Modeling.* 2007; 47(3):1097-1110; Bohm H J, Flohr A, Stahl M. Scaffold Hopping. *Drug Discov Today: Technologies.* 2004; 1(3): 217-224; Herr A J, Wills N M, Nelson C C, Gesteland R F, Atkins J F. Drop-off during ribosome hopping. *J Mol Biol.* 2001; 311(3):445-452; Core Hopping [computer program]: Schrodinger, LLC, New York, N.Y.; 2014). Using the VSW docking process the highest level of Glide precision, XP level docking was used (Sandor M, Kiss R, Keseru G M. Virtual Fragment Docking by Glide: a Validation Study on 190 Protein-Fragment Complexes. *Journal of Chemical Information and Modeling.* June 2010; 50(6):1165-1172; Docking: HTVS, SP, XP [computer program]. Glide5.5, Schrödinger, LLC, New York, N.Y. 2009: Schrödinger; 2010).

The complete results from this demonstrated a set of high affinity compounds based upon docking scores. Top binding inhibitors included high scoring SSI-3 (−10.38 kcal/mol), Compound A5 (−9.34 kcal/mol), SSI-2 (−9.0 kcal/mol), SSI-1 (−7.49 kcal/mol), and SSI-4 (−7.32 kcal/mol). Previous docking-only based compound screening fell short of our desired screening and design expectations, which encouraged the use of a Z-scoring method for combining Shape and QSAR with Docking into a rubric for synthesis selection.

Multiple SCD1 Novel Inhibitors Screened Via in Silico Docking

With SCD1, the binding poses for known inhibitors (>20) were determined using the Glide method outlined. The binding pocket for SCD1 is a long funnel-shaped deep pocket (FIG. 1A), which may easily accommodate stearoyl co-A binding. As shown in FIG. 1A-B, the region of SCD1 is highly alpha-helical in nature and has indicated electrostatic distribution for lipid binding. Here, all commercial inhibitors (Merck, Abbott, Sanofi Aventis, GSK, etc) are shown rendered in licorice style CPK molecules, which include A939572, GSK993, MF-238, ChemBL375265, and SAR707, and each structure is docked with the identified SCD1 binding pocket (FIG. 1A). These docking poses are overlaid to illustrate their distribution throughout the binding region. Additionally, shown in pink wire frame are the designed ligands that survived the Z-scoring filter (>240) (FIG. 1A). The compounds shown in green stick rendering are 41 synthesized compounds.

For better clarity, the top 260 compounds are removed from FIG. 1B to better illustrate the synthesized compounds position relative to the known inhibitors A939572 (Human $IC_{50}$ 37 nM) and ChemBL375265 (Human $IC_{50}$ 400 nM). FIG. 1B shows the structure-based reductive filter for SCD1 specific compounds. The Z-scoring filter operates in three iterative steps: Shape filter, Docking filter, and QSAR filter. The shape filter generates 100s of conformers for each of the thousands of compounds generated to best fit either SAR707 or A939572. Best fit of compounds with SAR707 had most surviving compounds (>800), thus selected for next filter, docking. Docking filter was applied to >800 compounds from the shape filter. Glide-XP docking retaining top 50% and addition of known inhibitors yields a pool of 286 compounds for QSAR filtering. A QSAR model was made from over 20,000 pharmacophore hypotheses based on a set of 32 known compounds ranging from low nanomolar activity to high milimolar (no activity). The QSAR model trained on this dataset generating a final pool of compounds with good predicted $IC_{50}$. The algorithm for ranking these final 242 compounds is shown.

Top Performing Experimental Inhibitors with in Silico Docking

All SCD1 inhibitors fit deep into a tunnel-like crevice inside SCD1 that includes the following residues within 4.5 Å of small molecules SSI-3, SSI-2, SSI-1, and SSI-4: Met79, Val339, Ile115, Thr231, Leu232, Tyr334, Ala343, Arg347, and Ile348.

De Novo Compounds 3D-QSAR Scoring

Greater than 20,000 pharmacophore models were tested and filtered, yielding the following statistics for the top three performing hypothesis models AAHHRR.1870, AAAHHR.4252, and AAAHHR.5952, which resulted in the following hypotheses values: survival of 2.885, 2.736, 2.478; survival-inactives of 1.262, 1.141, 1.190; Post-hoc of 3.259, 3.036, 2.493; Site of 0.43, 0.46, 0.25; Vector of 0.897, 0.755, 0.723; Volume of 0.552, 0.517, 0.517; Selectivity of 2.624, 2.442, 2.498; number of matches of 6, 10, 7; energy of 0.511, 1.208, 5.247; activity of 8.155, 7.292, 8.155; inactive of 1.623, 1.595, 1.288, respectively. With a PLS set at three, the QSAR results for the two top-performing models (AAAHHR.5952 and AAAHHR.4252) are Std Dev of 0.148, 0.1167; $R^2$ of 0.9886, 0.9952; F of 896.3, 1172.6; P of 3.438e-30, 6.798e-20; Stability of 0.4859, −0.1098; and RMSE of 5.5806, 1.077.

De Novo Compounds Combined Z-Score Ranking

The de novo compounds were inputted into the Z-scoring matrix outlined (Methods). The ranked pool of top compounds was sorted and all scored compounds that survived through QSAR were taken to the next step. Compounds were synthesized from this list and tested experimentally.

Compounds

Literature Compounds

A939572 was purchased from BioFine International. MF-438 (2-methyl-5-(6-(4-(2-(trifluoromethyl)phenoxy)piperidin-1-yl)pyridazin-3-yl)-1,3,4-thiadiazole) was synthesized by the medicinal chemistry group at Sanford-Burnham according to the published procedure, and was determined to by >95% pure by LC-MS. Carfilzomib and bortezomib were purchased from Selleck Chemicals.

SYNTHESIS

Example 1—SSI-1

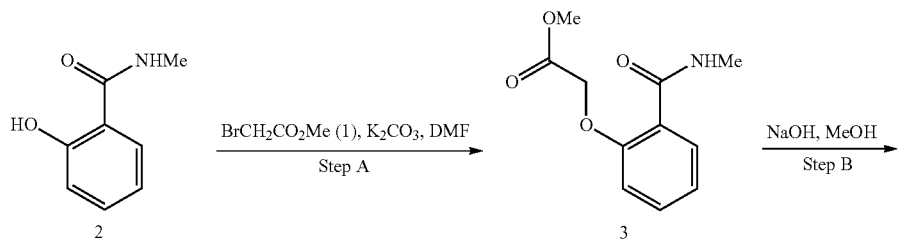

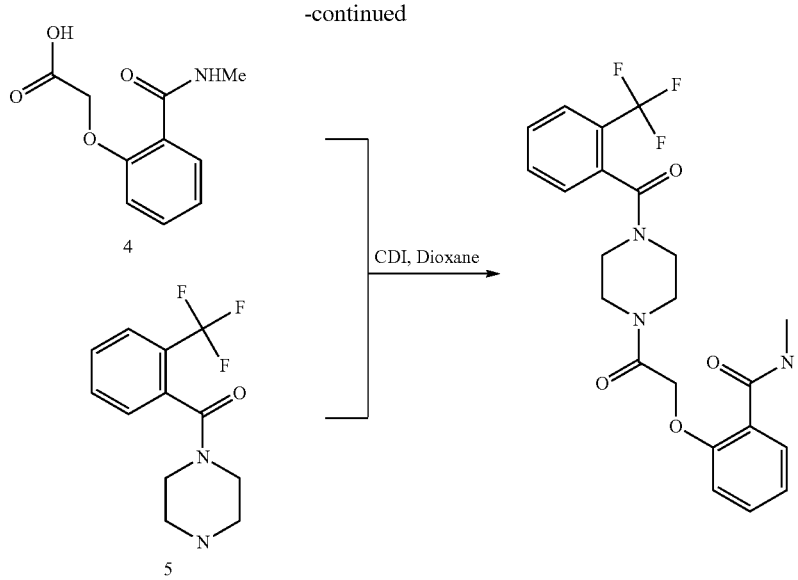

Step A

Potassium carbonate (2.76 g, 20 mmol) was added to a mixture of methyl bromoacetate (compound 1, 1.68 g, 11 mmol) and compound 2 (1.51 g, 0.01 mol) in DMF (50 mL) under vigorous stirring. The reaction mixture was stirred at r.t. for 24 h and then treated with water (200 mL) and extracted by $CH_2Cl_2$ (3×30 mL). The organic layer was washed with brine and dried under $Na_2SO_4$. The solvent was removed in vacuum giving compound 3 which was used for the next step without purification. Yield: 1.56 g (70%).

Step B

Compound 3 (1.56 g, 7 mmol) in MeOH (20 mL) of was added to 10% NaOH (5 mL). The reaction mixture was stirred at r.t for 8 h and then treated with 5% HCl until pH~3. The precipitate formed was filtered, dried and used for the next step without purification. Yield: 1.33 g (91%).

Step C CDI (117 mg, 0.72 mmol) was added to a solution of compound 4 (125 mg, 0.6 mmol) in dioxane (15 mL) under stirring and the mixture was heated at 50° C. for 30 minutes until end of liberation of gas. Then compound 5 (155 mg, 0.6 mmol) was added and the mixture was left stirring at 60° C. for 2 days (reaction is monitored by TLC). When reaction completed the mixture was treated with water (150 mL), extracted by $CH_2Cl_2$ (3×30 mL) washed with 5% $Na_2CO_3$ (30 mL), water (30 mL) and brine (30 mL), dried under $Na_2SO_4$. Then the solvent was removed in vacuum and the obtained residue was purified by flash chromatography to afford SSI-1. Yield: 135 mg (50%).

$^1$H NMR and LC/MS data for SSI-1 are shown in Exhibits A and B, incorporated herein in their entirety.

Example 2—SSI-2

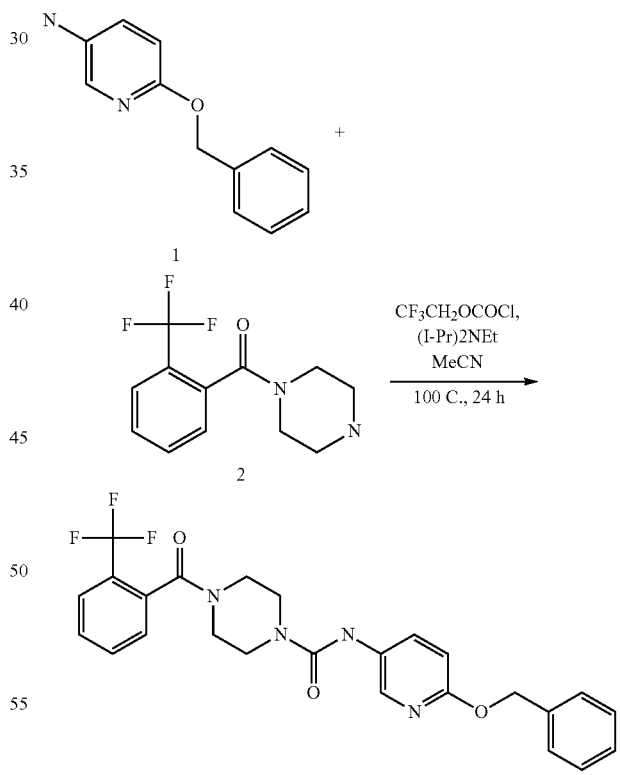

To a solution of compound 1 (200 mg, 1 mmol) in $CH_3CN$ (20 mL) trifluoroethyl chlorocarbonate (240 mg, 1.2 mmol) and DIPEA (322 mg, 2.5 mmol) were added under stirring at r.t. After 30 min of stirring amine 2 (258 mg, 1 mmol) the reaction mixture was heated at 100° C. for 24 h, then cooled, treated with water (250 mL) and extracted by $CH_2Cl_2$ (3×30 mL), washed with water (30 mL) and brine (30 mL), dried under $Na_2SO_4$. Then the solvent was removed in vacuum and the obtained residue was purified by flash chromatography giving pure SSI-2. Yield: 266 mg (50%).

Example 3—SSI-3

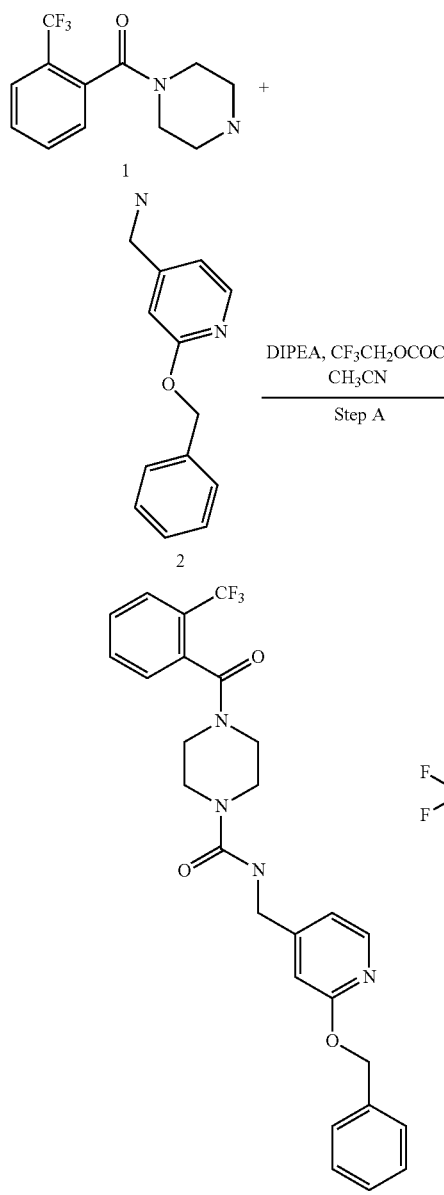

To a solution of compound 2 (214 mg, 1 mmol) in CH₃CN (30 mL) trifluoroethyl chloroformate (195 mg, 12 mmol) was added under stirring. Then diisopropyl ethyl amine (150 g, 2.5 mmol) and amine 3 (258 mg, 1 mmol). The reaction mixture was stirred at 100 C for 24 h. Then the mixture was treated with water (100 mL) and extracted by CH₂Cl₂ (3×30 mL). The organic layer was washed with water (30 mL) and brine (30 mL) and dried under Na₂SO₄. The solvent was removed in vacuum and the residue was purified by flash chromatography to give SSI-3. Yield: 314 mg (63%).

¹H NMR and LC/MS data for SSI-3 are shown in Exhibits C and D, incorporated herein in their entirety.

Example 4—SSI-4

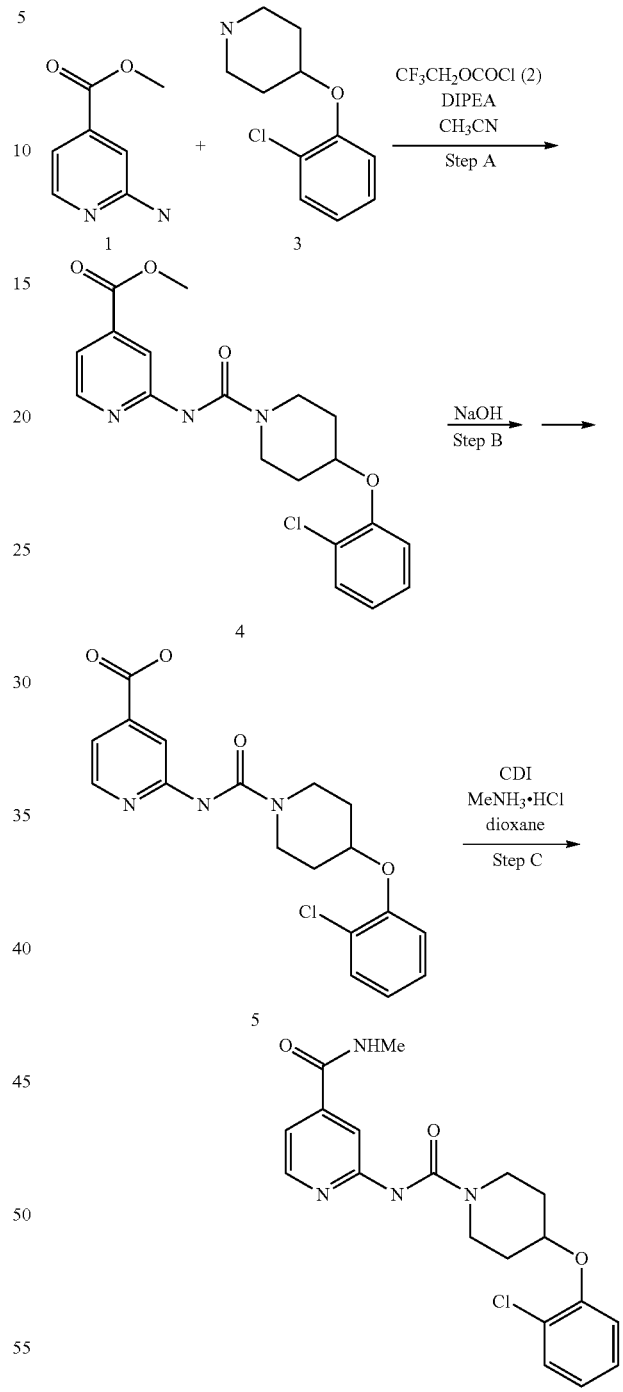

Step A

To a solution of compound 1 (1.52 g, 10 mmol) in CH₃CN (30 mL), compound 2 (1.95 g, 12 mmol) was added under stirring. Then diisopropyl ethyl amine (1.5 g, 25 mmol) and amine 3 (2.11 g, 10 mmol). The reaction mixture was stirred at 100° C. for 24 h. Then the mixture was treated with water (150 mL) and extracted by CH₂Cl₂ (3×30 mL). The organic layer was washed with water (30 mL) and brine (30 mL) and dried under Na₂SO₄. The solvent was removed in vacuum giving product 4 which was used for the next step without purification. Yield: 3.12 g (80%).
Step B
Compound 4 (2.73 g, 7 mmol) in MeOH (20 mL) of was added to 10% NaOH (5 mL). The reaction mixture was stirred at r.t for 8 h and then treated with 5% HCl until pH~3. The precipitate formed was filtered, dried giving compound 5 which was used for the next step without purification. Yield: 2.24 g (85%).
Step C
To a solution of compound 5 (376 mg, 1 mmol) in dioxane (20 mL) CDI (194 mg, 1.2 mmol) was added and heated at 50° C. for 30 min until completion of gas liberation. Then methyl amine hydrochloride (96 mg, 3 mmol) was added and the mixture was stirred at 60 C for 2 h. Then the reaction mixture was cooled and treated with water (100 mL) and extracted by $CH_2Cl_2$. The organic layer was washed with 10% $Na_2CO_3$ (20 mL), brine (20 mL) and dried under $Na_2SO_4$. The solvent was removed in vacuum and the residue was purified by flash chromatography to afford SSI-4. Yield: 148 mg (38%).

$^1$H NMR and LC/MS data for SSI-4 are shown in Exhibits E and F, incorporated herein in their entirety.
Methods of Use
General Materials and Methods
DNA Isolation and STR Analysis Genomic DNA was extracted from previously established cell lines (MDA-MB-468, MDA-MB-231, A375, HovTax2, OVCA420, Capan-2, MiaPaca2, DU-145, LNCAP, CaCo2, HT29, SNU449, A549, H1792), and cell lines established in the Copland laboratory (THJ16T, THJ29T, BCJ4T, and Mela15) using Purelink™ Genomic DNA mini kit (Invitrogen).

Sixteen STR markers were PCR amplified using fluorescently labeled primers from ABI (Applied Biosystems), and were analyzed using ABI 3130 (Applied Biosystems). Peak sizes were calculated versus a co-injected size standard using Gene Marker (Soft Genetics, State College, Pa.).
DNA Microarray RNA purified from subject tissues were sent to Mayo Clinic Advanced Genomic Technology Center Gene Expression Core for gene-array expression analysis using Affymetrix Human Genome U133 Plus 2.0 Array chips. Expression data is deposited at Gene Expression Omnibus Database (Accession #GSE-TBD). Details of data processing and methodology are previously described (Tun H W, Marlow L A, von Roemeling C A, Cooper S J, Kreinest P, Wu K, Luxon B A, Sinha M, Anastasiadis P Z, Copland J A. Pathway signature and cellular differentiation in clear cell renal cell carcinoma. PLoS One. 2010; 5(5):e10696). Genespring GX 7.3.1 (Agilent Technologies) was used to create heatmaps using Affymetrix default analysis settings and standard Genespring normalizations. Ingenuity® Systems was used to model signaling pathways.
Growth Assays Cells were seeded at 5,000 cells/well in clear-bottom 96-well plates in triplicate in Maintenance Media. Drug treatment was applied at a concentration of 1:1000 in reduced serum (3%) Maintenance Media. After 72 hours, cells were washed with PBS, and stored at −80° C. prior to analysis using CyQuant® Proliferation Analysis Kit (Invitrogen) as per manufacturers' protocol for relative fluorescence units. Alternatively, cells were plated $2\times10^5$/well in 12-well plates (Midwest Scientific) in triplicate prior to drug treatment. After 120 hour treatment, cell number was established using a Coulter Particle Counter (Beckman). Or, cells were plated (0.5 or $1\times10^5$/well) in 24-well plates (Midwest Scientific), 3×. After 72 hour treatment, cell number established using Coulter Particle Counter (Beckman). Oleic acid-albumin (Sigma Aldrich) was added to media at 5 μM, and was applied adjuvant to drug treatment. Drug stocks were prepared in DMSO (Sigma) at 1000×. $EC_{50}$ dosing per cell line was calculated using CalcuSyn® analytical software.
Luciferase Assay A498 and ACHN cells were transiently transfected with p5xATF6-GL3 UPR luciferase reporter (Addgene plasmid #11976) and pRL-CMV-renilla (Promega) using Lipofectamine 2000 (Invitrogen). Cells were treated as indicated for 24H, prior to collection and analysis using Promega Dual Luciferase assay kit per manufacturer's specifications. Luciferase activity was measured using Veritas Luminometer (Promega); and results are reported as relative luminescence.
Western Blot Analysis Protein extraction and western blot analysis was performed as previously described (Copland J A, Marlow L A, Kurakata S, et al. Novel high-affinity PPARgamma agonist alone and in combination with paclitaxel inhibits human anaplastic thyroid carcinoma tumor growth via p21WAF1/CIP1. Oncogene. Apr. 13, 2006; 25(16):2304-2317). Primary antibodies included SCD1 (Sigma-Aldrich, #HPA012107), BiP (Cell Signaling, #3183), CHOP (Cell Signaling, #2895), sXBP1 (Santa Cruz Biotechnology, #sc-7160), PARP (Cell Signaling, #9542), and (3-actin (Sigma-Aldrich, #A5441).
Meta Analysis Meta Analysis was performed as previously described (Kupershmidtl, SuQ J et al. Ontology-based meta-analysis of global collections of high-throughput public data. PLoS One 2010). The online platform Gene expression-based Outcome for Breast cancer Online (GOBO), including data from 1,881 patients and 11 studies employing Affimetrix U133A microarrays, was used for assessment of differential SCD1 expression in different breast cancer subtypes. Relationship between SCD1 expression and patient survival in different cancer subtypes was determined using KMPlotter, for lung and breast cancer. Affymetrix probe ID 200832 was identified as optimal probe for SCD1 analysis using jetset analysis was performed for relapse-free survival, patients split by median expression with best cutoff selected, no censoring for follow up threshold selected.
RNA Isolation and QPCR RNA isolation, preparation of cDNA, and QPCR performed as previously described (Tun H W, Marlow L A, von Roemeling C A, Cooper S J, Kreinest P, Wu K, Luzon B A, Sinha M, Anastasiadis P Z, Copland J A. Pathway signature and cellular differentiation in clear cell renal cell carcinoma. PLoS One. 2010; 5(5):e10696). TaqMan®FAM™ dye-labeled probes: GAPDH (Hs99999905_m1), POLR2A (Hs00172187_m1), SCD1 (Hs01682761_m1), HSPA5 (Hs99999174_m1), GADD45A (Hs00169255_m1), DD/T3 (Hs01090850_m1), and HERPUD1 (Hs01124269_m1). Fold-change comparisons between normal vs. tumor, and DMSO vs. drug treated samples calculated using the ΔΔCt method (Schmittgen T D, Livak K J. Analyzing real-time PCR data by the comparative C(T) method. Nat Protoc. 2008; 3(6):1101-8).
Immunohistochemistry and Immunofluorescence Analysis Formalin-fixed, paraffin-embedded subject tissues were mounted on slides, blocked with Diluent (DakoCytomation) for 30 min, and then probed for SCD (Sigma-Aldrich, #HPA012107). IHC scoring was performed as previously described (von Roemeling C A, Marlow L A, Wei J J, et al.

Stearoyl-CoA desaturase 1 is a novel molecular therapeutic target for clear cell renal cell carcinoma. *Clin Cancer Res.* May 1, 2013; 19(9):2368-2380). Cases where insufficient tumor tissue presented were excluded. 20× images were obtained using Scanscope XT and Imagescope software.

Cells were plated in 4-chamber slides (Thermo Scientific) prior to drug treatment. After 24 H drug treatment, cells were fixed using 4% paraformaldehyde (Sigma), permeabilized using 0.1% Triton X-100, and blocked with Diluent (Dako-Cytomation) for 1 H. Primary antibody was applied: ATF6 and HERPUD1 (Lifespan, #ABIN466153). Species specific secondary was applied (Jackson Labs). VECTASHIELD mounting media (Vector Labs) containing DAPI was used. Negative sections were prepared by incubating the slides in the absence of the primary antibody.

Flow Cytometry

After treatment, adhered and floating cells were collected using Accutase (Innovative Cell Technologies, Inc.), washed with PBS, and were suspended in 1× cold binding buffer (BD Pharmingen) at $1 \times 10^6$ cells/mL. Cells were stained with Propidium Iodide (BD Pharmingen). Analysis was performed using Accuri C6 flow cytometer. Unstained DMSO cells were used to set population parameters.

In Vivo Analysis $1 \times 10^6$ THJ16T ATC cells were subcutaneously injected in female athymic nu/nu mice (Harlan Laboratories). Treatment was initiated once tumor volumes reached 50-100 mm$^3$. MF-438 was suspended in 0.5% carboxymethylcellulose containing strawberry drink flavoring (0.1 g/mL) in sterilized H$_2$O at 25 mg/kg in a 100 µl dose, and administered via oral gavage once daily. Carfilzomib was solubilized in DMSO (4% of FC), suspended in 100% corn oil at 4 mg/kg per 50 uL dose and administered via intraperitoneal injection twice weekly on consecutive days. Tumor volume (0.5236[L*W*H]) and body weight were measured 2×/week. N=10 mice/group.

Biological Assays: Statistical Analysis

Data values are presented as fold change or percent of control±standard deviation unless otherwise specified. Fold change values 1.5< are considered statistically significant. Treatment group comparisons were analyzed using two-tailed paired Student's t-test with p<0.05 being considered statistically significant, and is indicated by asterisk (*). Drug synergy determined using CalcuSyn® (Chou T C, Hayball M P. CalcuSyn for Windows: multiple-drug dose effect analyzer and manual. Biosoft. 1997; Cambridge (UK)).

Example 5— Cell Activity of Compounds

In order to identify potential SCD1 inhibitors, a high-throughput proliferative-based screening method was used, with four ccRCC cell lines including A498, ACHN, Caki1, and Caki2. The SCD1 inhibitor MF-438 was included as a positive control. Known compounds ChemBL375265 (Liu G, Lynch J K, Freeman J, et al. Discovery of potent, selective, orally bioavailable stearoyl-CoA desaturase 1 inhibitors. *Journal of medicinal chemistry*. Jun. 28, 2007; 50(13): 3086-3100) (SetA.100) and SAR707 (Voss M D, Zoller G, Matter H, et al. Discovery and pharmacological characterization of SAR707 as novel and selective small molecule inhibitor of stearoyl-CoA desaturase (SCD1). *European journal of pharmacology*. May 5, 2013; 707(1-3): 140-146) (TC03.100) were included as single-blinded positive controls, and are indicated with an asterisk (*).

FIG. 1 shows the $EC_{50}$ values of known (ChemBL375265) and novel (SSI-1, SSI-4, SSI-3, SSI-2) SCD1 inhibitors generated using linear regression modeling. Concentrations effective to decrease cell proliferation by 50% ($EC_{50}$) were established for ChemBL375265, SSI-1, SSI-4, SSI-3, SSI-2 based on linear regression models generated using Calcusyn® analytical software.

Figure 2B:
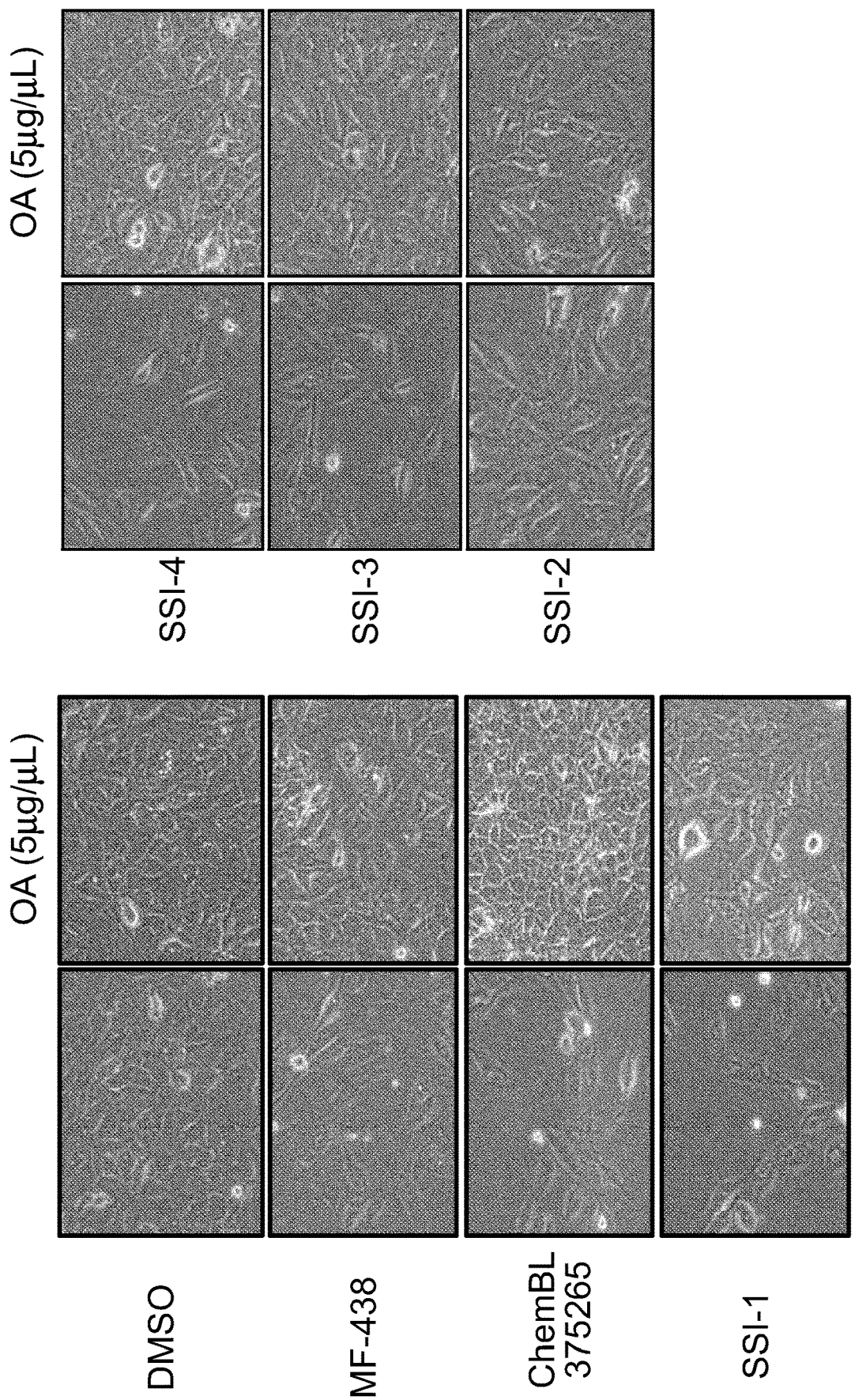

Exogenous application of OA (oleic acid), the primary product of SCD1 enzymatic activity, demonstrates rescue of the proliferative defects induced by SCD1 inhibitors (Roongta U V, Pabalan J G, Wang X, et al. Cancer cell dependence on unsaturated fatty acids implicates stearoyl-CoA desaturase as a target for cancer therapy. *Mol Cancer Res.* November 2011; 9(11):1551-1561). A498, ACHN, and Caki1 cell lines were treated with the $EC_{50}$ dose of each MF-438, ChemBL375265, SSI-1, SSI-4, SSI-3, and SSI-2 with or without concomitant application of OA (5 µg/µL). Near total rescue of cell proliferation was observed with OA in all three cell lines treated with MF-438, ChemBL375265, SSI-1, SSI-4, SSI-3, and SSI-2 (FIG. 2A). Representative images of A498 cell morphology and density treated with each compound+/−OA are shown in (FIG. 2B).

Example 6— Functional Characterization of Novel Compounds

Activating transcription factor 6 (ATF6) is a key regulator of the unfolded protein response (UPR) that recognizes unfolded protein response elements (UPRE) in the promoter regions of several key mediators of the ER stress response, initiating their transcription (Wang Y, Shen J, Arenzana N, Tirasophon W, Kaufman R J, Prywes R. Activation of ATF6 and an ATF6 DNA binding site by the endoplasmic reticulum stress response. *J Biol Chem. Sep.* 1, 2000; 275(35): 27013-27020). A498 and ACHN transfected with an ATF6-UPRE luciferase reporter were treated with the $EC_{50}$ doses of ChemBL375265, SSI-1, SSI-4, SSI-3, and SSI-2 with or without OA supplementation were evaluated in order to determine whether the identified compounds could recapitulate activation of the UPR. ChemBL375265, SSI-1, SSI-4, and SSI-2 treatment resulted in a significant upregulation of luciferase activity in both cell lines that was completely blocked with exogenous application of OA (FIG. 3A). SSI-3 also induced reversible luciferase activity in ACHN cells (FIG. 3A). Upregulation of the UPR markers BiP (heat shock 70 kDa protein, GRP78) and CHOP (damage inducible transcript 3, DDIT3) was evaluated by Western blot in A498 and ACHN cells treated with the $EC_{50}$ doses of ChemBL375265, SSI-1, SSI-4, SSI-3, and SSI-2 with or without OA supplementation. ChemBL375265, SSI-1, SSI-4, SSI-3 and SSI-2 strongly induced both BiP and CHOP expression in both cell lines that was blocked with concomitant OA treatment (FIG. 3B).

Example 7—SCD1 Expression Profile in Aggressive Malignancies

Meta analysis was performed using public gene arrays that included normal and tumor datasets in order to evaluate SCD1 transcript expression. Multiple datasets were queried per cancer type for SCD1 transcript expression. These results revealed an overall trend for aberrant SCD1 expression in tumor versus normal, with elevated expression observed in several aggressive malignancies such as kidney, liver, breast, lung, and pancreatic cancer.

The meta analysis of published gene array datasets compared tumor versus normal controls. Cancer types are listed by score where SCD1 transcript expression is unregulated, in descending order. Gene scoring is established by numerical score, where a gene is ranked based on statistical significance and consistency of expression across queried biosets. A numerical score of 100 is assigned to the highest ranked gene, and all other scores are then normalized to that gene. Number of queried datasets, and the predominant trend of SCD1 expression per cancer type is given.

Unregulated SCD1 transcript expression was found in the following cancers: kidney cancer, liver cancer, breast cancer, adrenal cancer, some forms of lymphoma, malignant tumor of muscle, thymus cancer, uterine cancer, gastric cancer, thyroid cancer, secondary malignant neoplastic disease, cancer of the head and neck, lung cancer, pancreatic cancer, primary malignant neoplasm of the bone, and ovarian cancer. Downregulated SCD1 transcript expression was found in the following cancers: some forms of leukemia, T-cell lymphoma, myeloid leukemia, brain cancer, prostate cancer, bladder cancer, lymphoid leukemia, neuroendocrine tumor, skin cancer, B-cell lymphoma, esophageal cancer, testicular cancer, and multiple myeloma/plasmacytoma.

Figure 5:
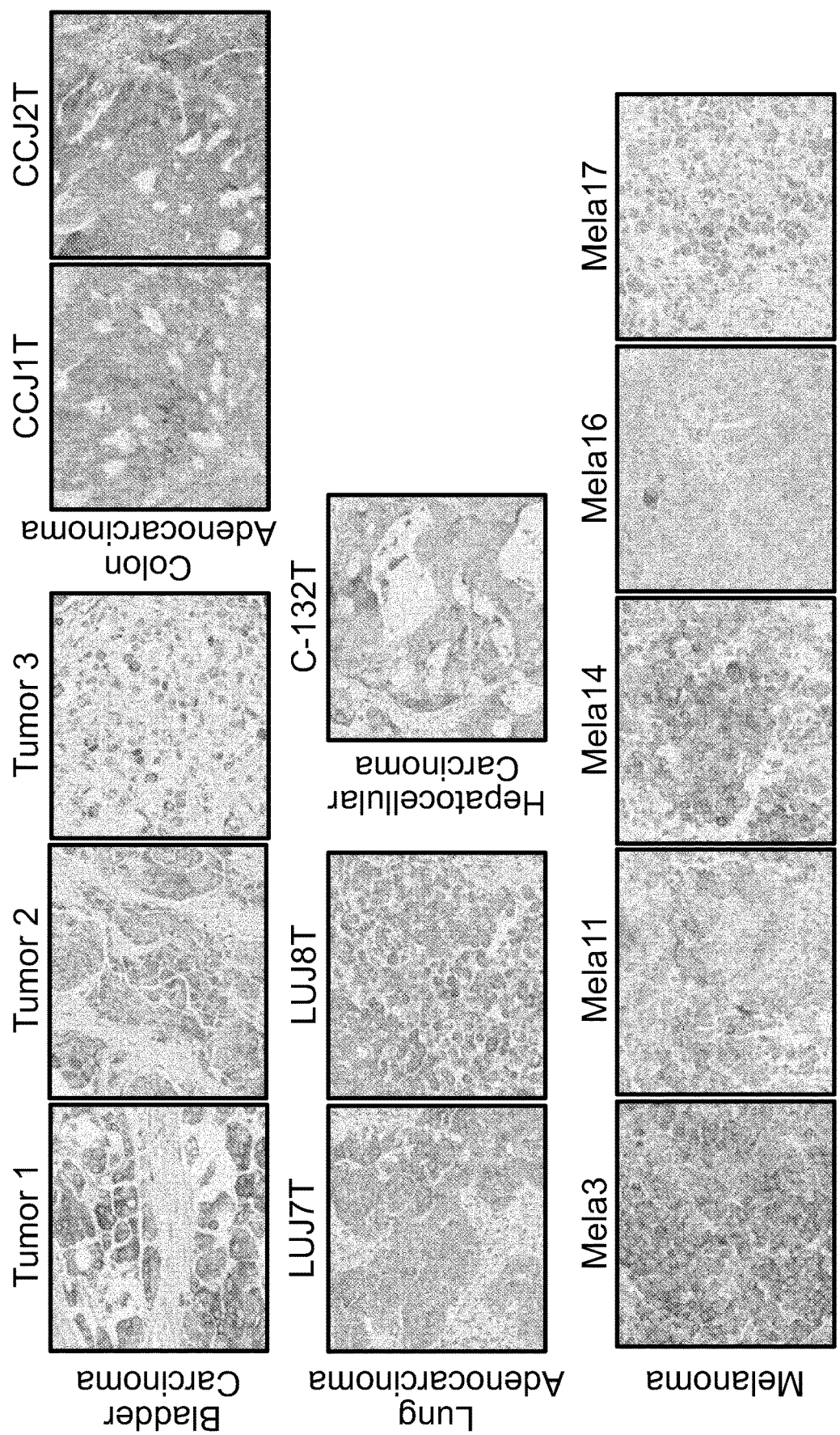
FIG. 5 shows IHC of subject primary tumor tissues for SCD1 protein expression in bladder, colon, lung, hepatocellular carcinomas, and melanoma.
Figure 6:
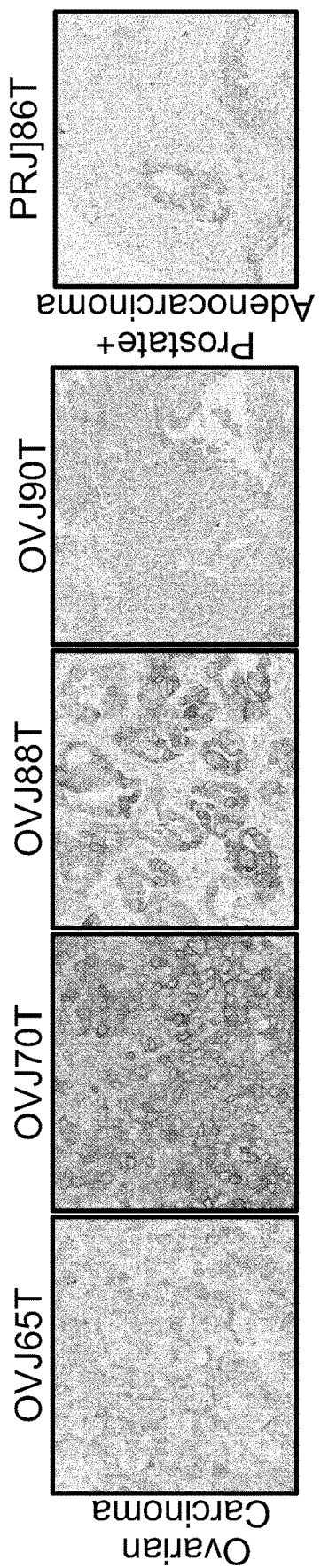
FIG. 6 shows IHC of subject primary tumor tissues for SCD1 protein expression in ovarian and prostate cancers.
Figure 7:
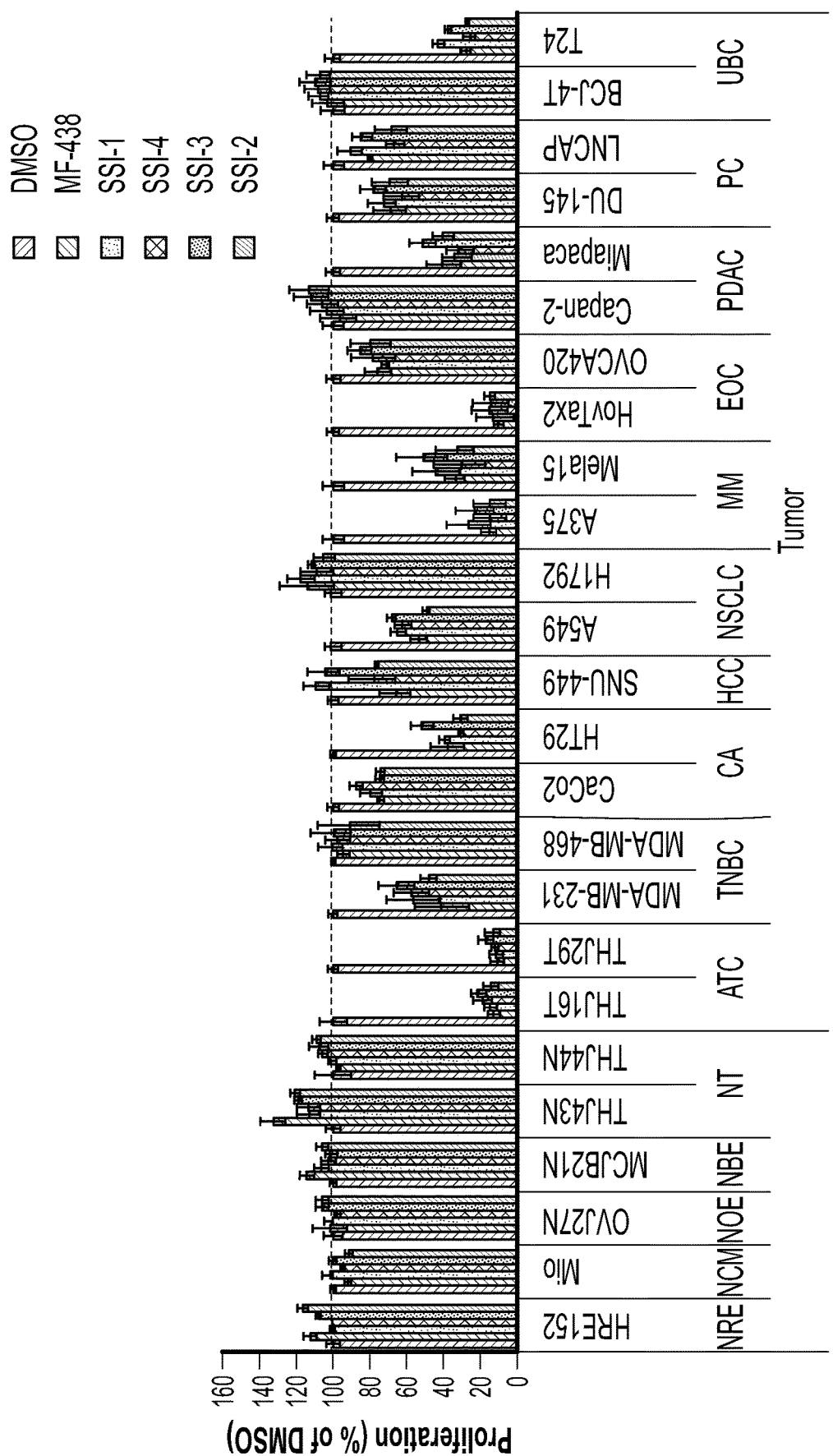
FIG. 7 shows effects of compounds on proliferation in various tissues. Selective SCD1 inhibitors (SSI) are shown in the Figure as follows: SSI-1, SSI-2, SSI-3, SSI-4. NRE=Normal Renal Epithelium; NCM=Normal Colon Myometrium; NOE=Normal Ovarian Epithelium; NBE=Normal Breast Epithelium; NT=Normal Thyroid; ATC=Anaplastic Thyroid Carcinoma; UBC=Urothelial Transitional Cell Bladder Carcinoma; TNBC=Triple Negative Breast Carcinoma; CA=Colorectal Adenocarcinoma; HCC=Hepatocellular Carcinoma; NSCLC=Non-small cell Lung Adenocarcinoma; MM=Malignant Melanoma; EOC=Epithelial Cell Ovarian Carcinoma; PDAC=Pancreatic Ductal Adenocarcinoma; PC=Prostatic Carcinoma.
Figure 8:
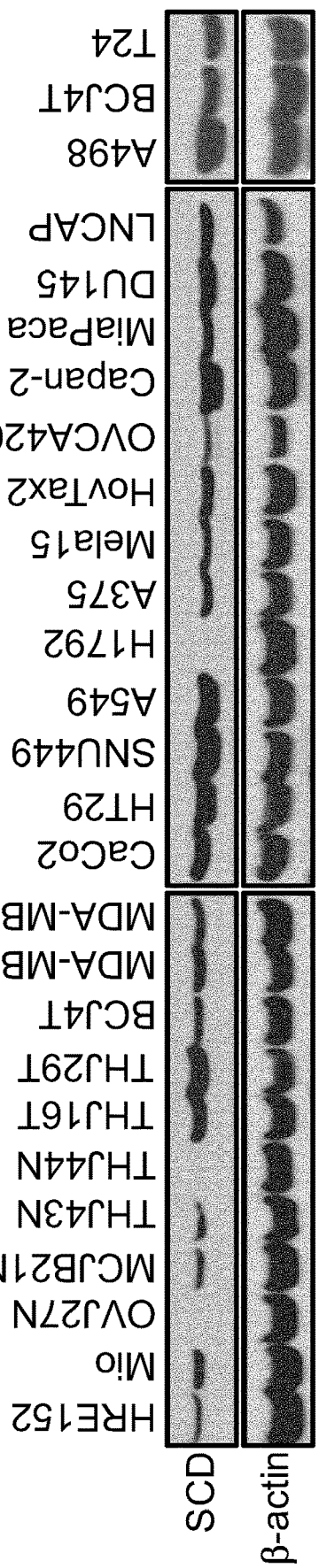
FIG. 8 shows a Western blot for SCD1 protein expression for all cell lines used in the high-throughput proliferative screen.

Immunohistochemistry (IHC) of subject primary tumor tissues including bladder carcinoma, colon adenocarcinoma, lung adenocarcinoma, hepatocellular carcinoma, malignant melanoma, ovarian carcinoma, and prostate adenocarcinoma revealed strong positive staining in a large proportion of the samples examined (FIGS. 5 and 6). Cell lines established from a cohort of aggressive malignancies as well as a representative group of non-cancerous cells were examined for proliferative response to SSI-1, SSI-4, SSI-3, and SSI-2 as well as the known SCD1 inhibitor, MF-438, using the high-throughput format employed. Of the non-cancerous cells tested, a reduction in cell proliferation of approximately 20% was observed in HK2, a transformed renal epithelial cell line, with MF-438, SSI-4, and SSI-2 treatment. Significant reductions in tumor cell proliferation were observed in tumor cells treated with the compounds of the disclosure that were comparable to MF-438. These include THJ16T, THJ29T, MDA-MB-231, CaCo2, HT29, SNU-449, A549, A375, Mela15, HovTax2, OVCA420, MiaPaca, Du-145, and LNCAP. Western blot for SCD1 protein expression revealed elevated SCD1 in the majority of tumor cell lines screened as compared to normal cell line expression, except for the HK2 cells which also demonstrate abundant SCD1 protein (FIG. 8).

Example 8—Gene-Array Analysis in Thyroid Tissue

Figure 9A:
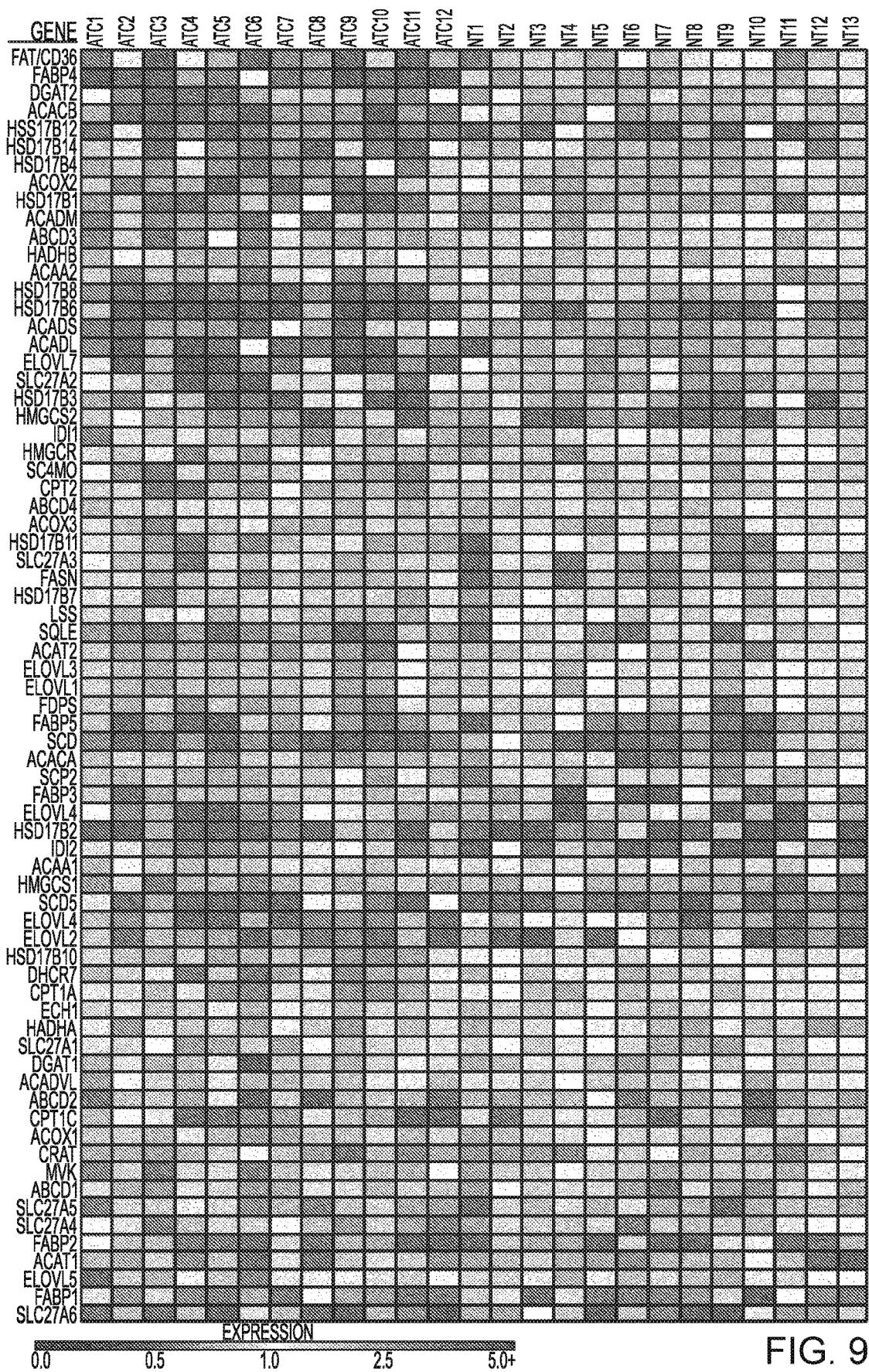

Gene-array analysis was performed using 12 ATC (anaplastic thyroid cancer) tumor and 13 normal thyroid (NT) tissue specimens. Results revealed altered expression in fatty acid metabolism including fatty acid synthesis, cholesterol synthesis, mitochondrial and peroxisomal fatty acid oxidation, and cellular uptake of fatty acids. Findings are depicted in the heatmap in FIG. 9A, and mean fold-change values compared to normal thyroid tissue is presented in supplementary table 1 (ST1). SCD expression was consistently elevated in tumor samples, induced by 8.8 and 2.4-fold for SCD1 and SCD5, respectively (FIG. 9A and Table 1).

TABLE 1

Change in Fatty Acid Synthesis in Thyroid Cancer Tissue

| | Gene Symbol | Fold Change |
|---|---|---|
| Fatty Acid Synthesis | | |
| Acetyl-CoA Carboxylase | ACACA | 1.74* |
| | ACACB | 0.69 |

TABLE 1-continued

Change in Fatty Acid Synthesis in Thyroid Cancer Tissue

| | Gene Symbol | Fold Change |
|---|---|---|
| Fatty Acid Synthase | FASN | 1.36 |
| Elongation of very long chain fatty acids | ELOVL1 | 1.28 |
| | ELOVL4 | 2.22* |
| | ELOVL5 | 0.82 |
| | ELOVL7 | 0.30 |
| Stearoyl-CoA Desaturase | SCD | 8.84* |
| | SCD5 | 2.38* |
| Diacylglycerol O-acyltransferase | DGAT2 | 1.36 |
| Cholesterol Synthesis | | |
| HMG-CoA Synthase | HMGCS1 | 1.04 |
| HMG-CoA Reductase | HMGCR | 0.72 |
| Mevalonate Kinase | MVK | 0.89 |
| Isopentenyl Diphosphate-Isomerase | IDI1 | 0.96 |
| | IDI2 | 2.19* |
| Farnesyl Diphosphate Synthetase | FDPS | 1.38 |
| Squalene Epoxidase | SQLE | 2.72* |
| Lanosterol Synthase | LSS | 1.15 |
| Sterol C4-methyl Oxidase | SC4MO | 0.97 |
| 7-Dehydrocholesterol Reductase | DHCR7 | 0.93 |
| Hydroxysteroid (17-beta) Dehydrogenase | HSD17B1 | 0.71 |
| | HSD17B4 | 0.44 |
| | HSD17B6 | 0.10 |
| | HSD17B7 | 0.99 |
| | HSD17B8 | 0.25 |
| | HSS17B12 | 0.82 |
| Mitochondrial Fatty Acid Oxidation | | |
| Carnitine palmitoyltransferase 2 | CPT1A | 1.38 |
| Carnitine palmitoyltransferase 2 | CPT2 | 1.03 |
| Trifunctional protein | HADHA | 1.02 |
| | HADHB | 0.75 |
| Acyl-CoA dehydrogenases | ACADS | 0.32 |
| | ACADM | 0.60 |
| | ACADL | 0.24 |
| | ACADVL | 0.90 |
| Acetyl-CoA acetyltransferase | ACAT1 | 1.16 |
| | ACAT2 | 1.73* |
| Peroxisomal Fatty Acid Oxidation | | |
| Peroxisomal acyl-CoA oxidase 1 | ACOX1 | 0.85 |
| | ACOX2 | 0.40 |
| | ACOX3 | 1.09 |
| ATP-Binding cassette, Sub-family D | ABCD1 | 0.85 |
| | ABCD3 | 0.73 |
| | ABCD4 | 0.85 |
| Acetyl-CoA acyltransferase 1 | ACAA1 | 1.02 |
| Acetyl-CoA acyltransferase 2 | ACAA2 | 0.88 |
| Sterol carrier protein | SCP2 | 1.16 |
| Carnitine acetyl transferase | CRAT | 1.03 |
| 2-Enoyl-CoA hydratase | ECH1 | 0.98 |
| Cellular Uptake of Fatty Acids | | |
| Fatty acid translocase | FAT/CD36 | 2.80* |
| Fatty acid binding protein | FABP2 | 0.60 |
| | FABP4 | 6.03* |
| | FABP5 | 4.33* |
| Solute carrier Family (Fatty acid transporter) | SLC27A1 | 0.86 |
| | SLC27A2 | 0.36 |
| | SLC27A3 | 1.96* |
| | SLC27A4 | 0.80 |

Figure 9B:
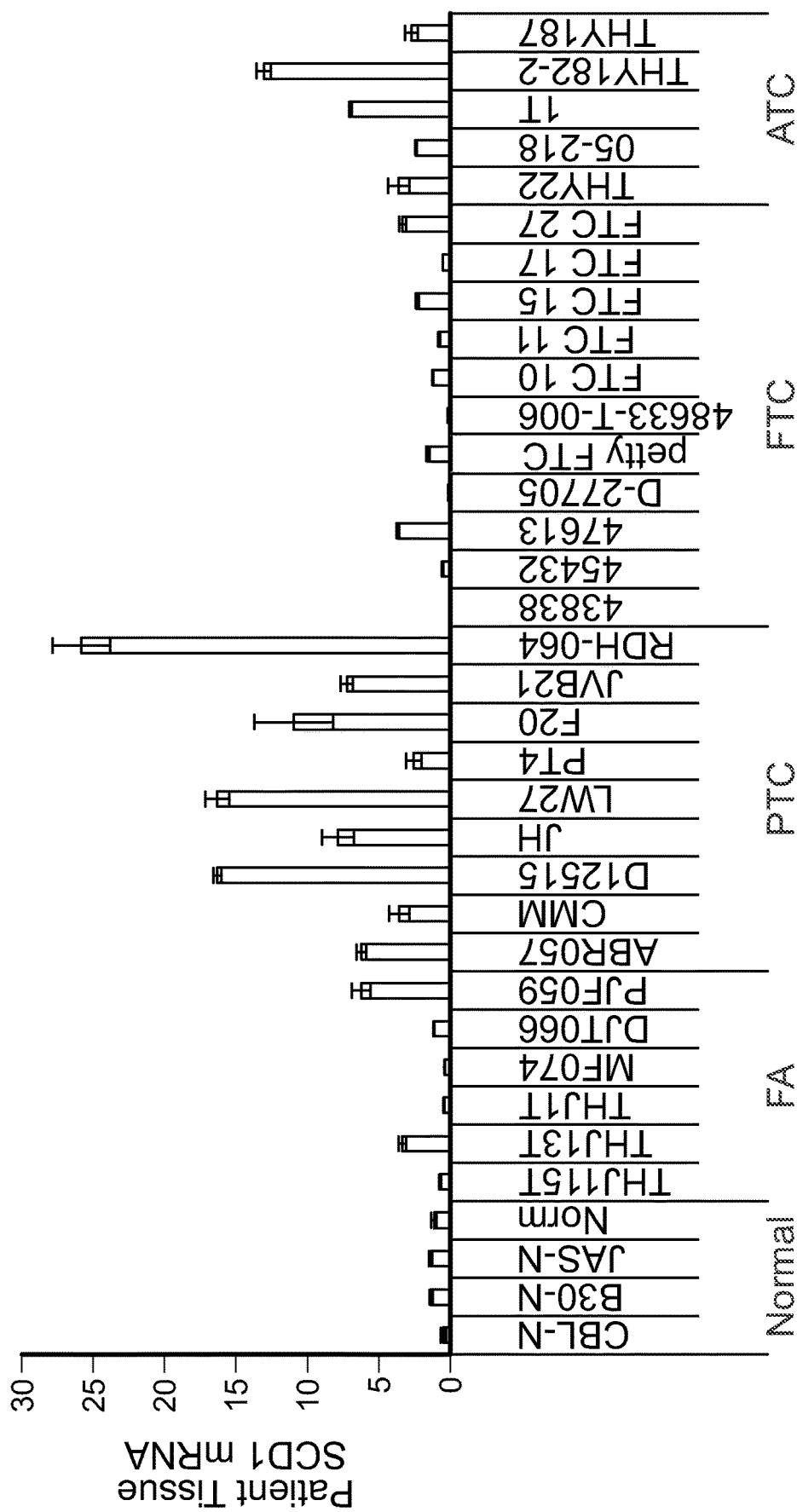
Figure 9C:
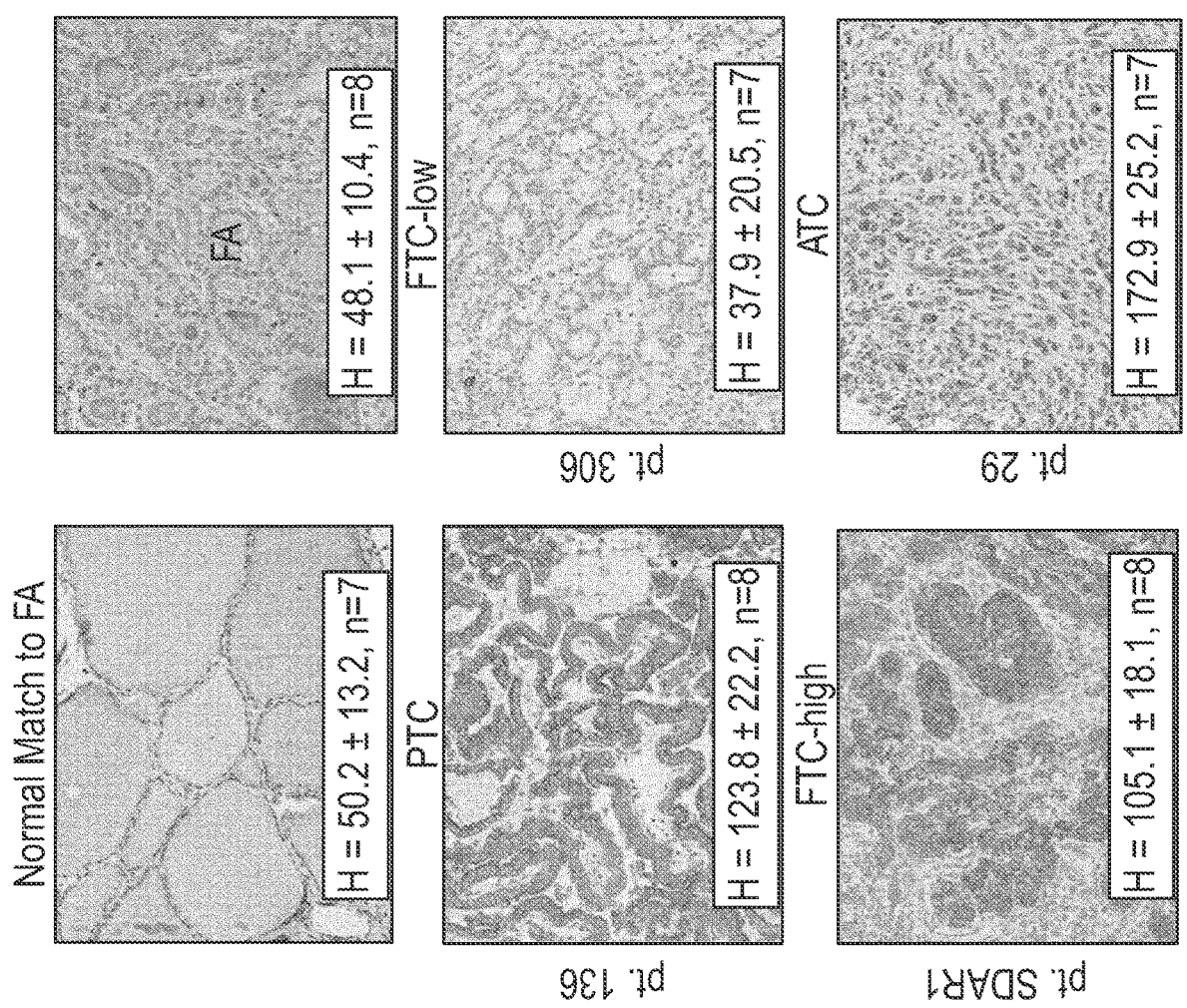

In order to evaluate the expression profile of SCD1 in thyroid malignancy, quantitative PCR (QPCR) as well as immunohistochemistry (IHC) of subject samples was performed. SCD1 was transcriptionally upregulated in all ATC and papillary thyroid carcinoma (PTC) samples examined, as well as several samples of follicular adenoma (FA) and follicular thyroid carcinoma (FTC) (FIG. 9B). IHC analysis confirmed elevated SCD1 protein in ATC, PTC, and high grade FTC lesions (invasive), where low SCD1 expression was observed in low grade FTC lesions (local, non-invasive), FA, and NT tissue (FIG. 9C). In order to evaluate whether cell line models recapitulate SCD1 expression patterns observed in subject tissue, representative subject-derived cells from normal, benign, well-differentiated, and ATC tissues were examined. Available subject TMN classifications are provided (FIG. 9D). SCD1 was found to be consistently over-expressed in ATC and FTC cells, both transcriptionally and at the protein level (FIGS. 9E-F). As the majority of established FTC cell models are derived from advanced lesions, these results are consistent with those observed in tissue samples. Surprisingly, low levels of SCD1 were observed in PTC cell lines (FIGS. 9E-F).

Gene-array analysis of ATC subject samples illuminates significant alterations in fatty acid metabolism in these tumors (FIG. 9A and Table 1), presenting an innovative therapeutic opportunity for this aggressive malignancy. Of the genes evaluated, SCD1 was not only the most highly over-expressed, but it was also consistently elevated in all tumor samples as compared to normal levels (FIG. 9 and Table 1). While other thyroid malignancies also demonstrate SCD1 upregulation both transcriptionally and at the protein level (FIG. 9).

Example 9— Effect of SCD1 Inhibitor on Proliferation of Thyroid Cancer Cells

The efficacy of pharmacologic inhibition of this enzyme on tumor cell proliferation after a 72H treatment was determined, using A939572—a commercially available small molecule SCD1 inhibitor (Xin Z, Zhao H, Serby M D, Liu B, Liu M, Szczepankiewicz B G, Nelson L T, Smith H T, Suhar T S, Janis R S, Cao N, Camp H S, Collins C A, Sham H L, Surowy T K, Liu G. Discovery of piperidine-aryl urea-based stearoyl-CoA desaturase 1 inhibitors. Bioorg Med Chem Lett. 2008; 18(15):4298-302). No response was observed in either NT or FA cells (FIG. 10A-B). A minimal response was observed in 2/5 PTC cells at high doses of A939572 (FIG. 10C). Despite conspicuous SCD1 expression in 4 of the 5 FTC cells tested, no response to A939572 was observed (FIG. 10D). All ATC cells exhibited a dose-dependent decrease in proliferation (FIG. 10E), with 50% effective concentrations ($EC_{50}$) in the low nanomolar dose range. MF-438 (Leger S, Black W C, Deschenes D, Dolman S, Falgueyret J P, Gagnon M, Guiral S, Huang Z, Guay J, Leblanc Y, Li C S, Masse F, Oballa R, Zhang L. Synthesis and biological activity of a potent and orally bioavailable SCD inhibitor (MF-438). Bioorg Med Chem Lett. 2010; 20(2):499-502), a potent and orally bioavailable SCD1 inhibitor that has been shown to be effective in rodent models for diabetes and obesity and is chemically distinct from A939572, similarly produced a dose-dependent decrease in ATC proliferation with $EC_{50}$ values in the low nanomolar dose range (FIG. 10F).

Figures 11D, 11E:
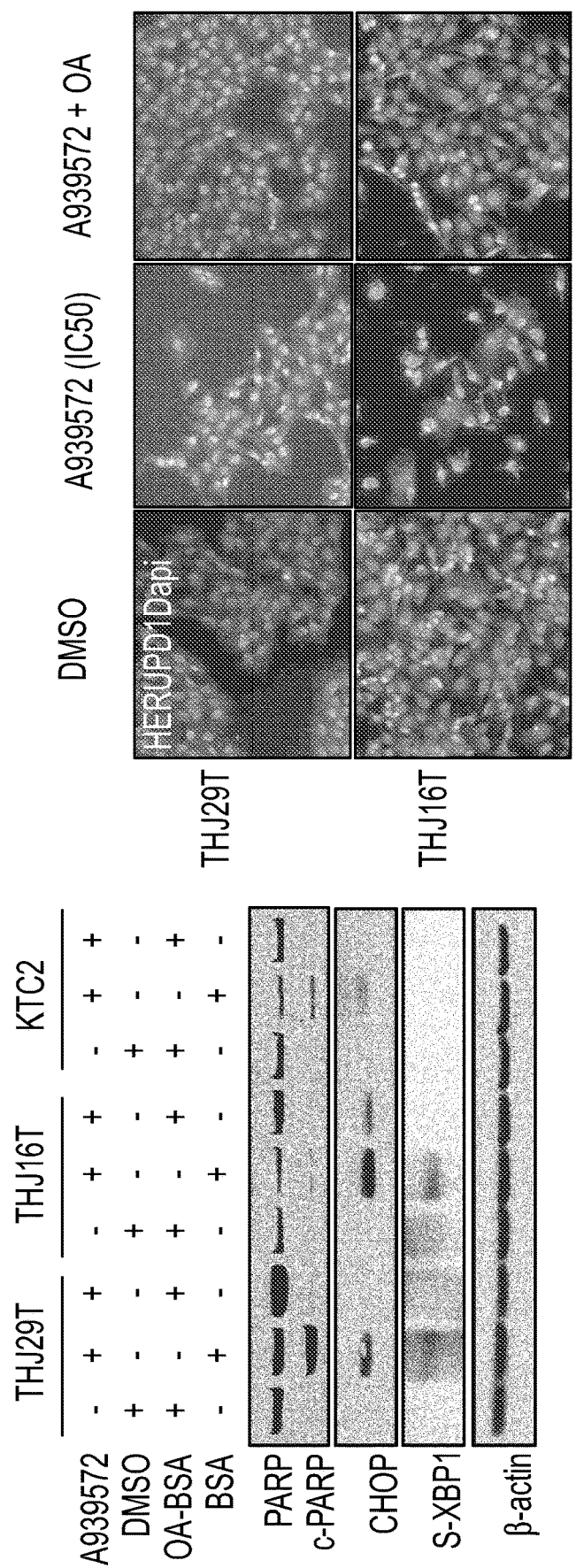

Exogenous application of MUFAs, such as oleic or palmitoleic acid, can rescue the proliferative defects generated by SCD1 inhibition as these are the primary products of SCD1 enzymatic activity (Roongta U V, Pabalan J G, Wang X, Ryseck R P, Fargnoli J, Henley B J, Yang W P, Zhu J, Madireddi M T, Lawrence R M, Wong T W, Rupnow B A. Cancer cell dependence on unsaturated fatty acids implicates stearoyl-CoA desaturase as a target for cancer therapy. Mol Cancer Res. 2011; 9(11):1551-61). THJ29T, THJ16T and KTC2 cells were treated with the $EC_{50}$ dose of A939572 or MF-438 for 72 H with or without 5 µM of oleic acid (OA). Concomitant treatment of cells using either SCD1 inhibitor with OA resulted in complete rescue of proliferation (FIGS. 11A-B). In previous work evaluating RCC cellular response to targeted inhibition of SCD1, the ER stress pathway, or UPR, was determined to be activated (von Roemeling C A, Marlow L A, Wei J J, Cooper S J, Caulfield T R, Wu K, Tan W W, Tun H W, Copland J A. Stearoyl-CoA desaturase 1 is a novel molecular therapeutic target for clear cell renal cell carcinoma. Clin Cancer Res. 2013; 19(9):2368-80). SCD1 inhibitor treated ATC cells were examined for UPR activation to evaluate whether or not these cells were responding similarly. THJ29T, THJ16T, and KTC2 were treated with a 10 µM dose of A939572 with or without 5 µg/µL OA for 24 hours. Transcriptional upregulation of UPR markers including GADD45α (Growth arrest and DNA damage inducible transcript 1, DDIT1), DDIT3 (DNA damage inducible transcript 3, CHOP), and HERPUD1 homocysteine-inducible, ER stress inducible, ubiquitin-like-1) were evaluated by QPCR. All three were transcriptionally upregulated in response to A939572 in all cell lines, where simultaneous treatment with OA restored expression back to control levels (FIG. 11C). Additionally, treatment of all three ATC cells with A939572 ($EC_{50}$ dose) for 72H induced apoptosis as evaluated by PARP cleavage; this was abrogated with OA treatment. Similarly, protein expression of UPR factors CHOP, spliced XBP-1 (X-box binding protein 1, s-XBP1) (FIG. 11D), and HERPUD1 (FIG. 11E) could be reversibly induced with SCD1 inhibitor treatment in ATC cells.

Example 10— SCD1 Inhibitor Synergy in Combination with Proteasome Inhibitors

The UPR pathway is activated by a variety of cellular stressors which leads to accumulation of mis-folded proteins within the ER. There are three transmembrane ER resident master regulators of the UPR: PERK (Eukaryotic translation initiation factor 2-alpha kinase 3, EIF2AK3), IRE1 (Endoplasmic to nucleus signaling 1, ERN1), and ATF6 (Activating transcription factor 6) (Xu C, Bailly-Maitre B, Reed J C. Endoplasmic reticulum stress: cell life and death decisions. J Clin Invest. 2005; 115(10):2656-64; Walter P, Ron D. The unfolded protein response: from stress pathway to homeostatic regulation. Science. 2011; 334(6059):1081-6; Hetz C, Chevet E, Harding H P. Targeting the unfolded protein response in disease. Nat Rev Drug Discov. 2013; 12(9):703-19). PERK activation leads to repression of protein translation. IRE1 activation triggers endoribonuclease activity that splices XBP1, a molecular chaperone and transcriptional activator of other ER stress response proteins, leading to growth arrest or apoptosis. ATF6 is a transcription factor that is proteolytically processed at the Golgi into its active state, whereby it targets promoter regions containing UPR elements (UPRE; ER stress elements, ERSE). Altogether the UPR facilitates the attenuation of protein translation, molecular chaperone mediated protein refolding, and ERAD. The primary goal of this pathway is to restore cellular homeostasis; however in extreme or prolonged cases of stress it can also initiate cellular senescence or death (Kim I, Xu W, Reed J C. Cell death and endoplasmic reticulum stress: disease relevance and therapeutic opportunities. Nat Rev Drug Discov. 2008; 7(12):1013-30). Targeted inhibition of the ERAD component of the UPR using a proteosome inhibitor such as bortezomib or carfilzomib in conjunction with SCD1 inhibition may enhance cellular stress and drive tumor cells toward cell death in a synergistic manner.

Figure 13D:
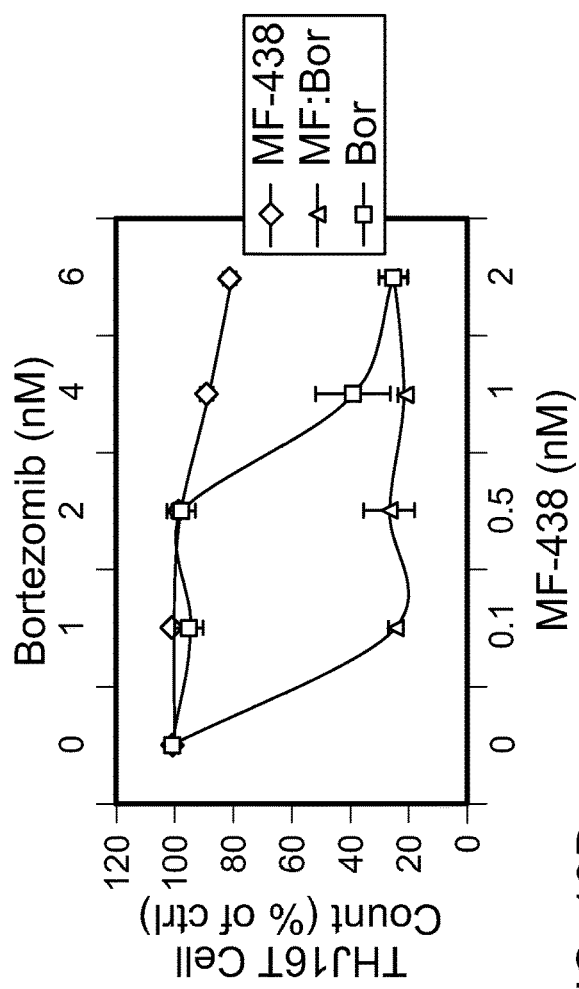
Figure 13E:
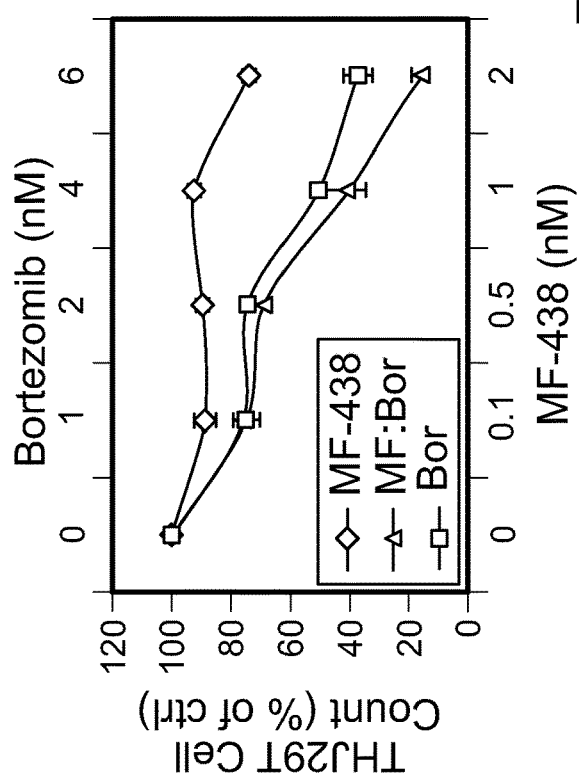

THJ29T, THJ16T, and KTC2 were treated with carfilzomib (FIG. 12A) or bortezomib for 72H in order to establish $EC_{50}$ values. All three cell lines responded in a dose-dependent manner to either inhibitor, yielding EC50's in the low nanomolar dose range. Anti-proliferative drug synergy was evaluated in THJ29T and THJ16T treated with either A939572 or MF-438 in combination with either bortezomib or carfilzomib for 48H. Synergy was assessed using CalcuSyn analytical software, which determines the combination index (CI) based on the Chou-Talalay method where CI values >1 represent an antagonistic effect and values <1 represent synergy, and lower values signify enhanced synergy (Chou T C, Talalay P. Analysis of Combined Drug Effects—a New Look at a Very Old Problem. Trends in Pharmacological Sciences. 1983; 4(11):450-4). Strong synergy was observed in both cell lines using A939572 together with either carfilzomib (FIG. 12B-C) or bortezomib (FIG. 13B-C), and similarly using MF-438 together with either carfilzomib (FIG. 12D-E) or bortezomib (FIG. 13D-E).

Anti-proliferative synergy was evaluated with increased cell death. THJ29T and THJ16T treated for 48H with $EC_{50}$ doses of either A939572 or MF-438 in combination with either carfilzomib or bortezomib were probed for PARP cleavage and CHOP expression, both markers indicative of apoptosis (FIGS. 14A-B, 15A-B). In THJ29T and THJ16T treated with either A939572 or MF-438 and carfilzomib, significant PARP cleavage was observed in both monotherapy and combinatorial groups as compared to DMSO control (FIGS. 14A-B), however a clear increase in PARP cleavage was only observed in the MF-438 and carfilzomib combinatorial treated groups as compared to monotherapy (FIG. 14B). Additionally, CHOP expression was synergistically increased in THJ16T MF-438/carfilzomib (FIG. 14B) as well as the A939572/bortezomib combinatorial group (FIG. 15B), however no clear increase was observed in the other treatment combinations or in THJ29T as compared to monotherapy. Cell death was additionally examined via flow cytometry using propidium iodide staining. THJ29T and THJ16T were treated for 48H with EC50 doses of either A939572 or MF-438 in combination with either carfilzomib or bortezomib prior to staining and analysis. Increased cell death in the combination group versus the control and either monotherapy was observed in both cell lines treated with MF-438 and carfilzomib, and in THJ29T treated with A939572 and carfilzomib (FIG. 14D). No additive increases in cell death were observed with either SCD1 inhibitor with bortezomib (FIG. 15C).

Example 11— SCD1 Inhibitor Synergy in Combination with mTor Inhibitors

Figure 16:
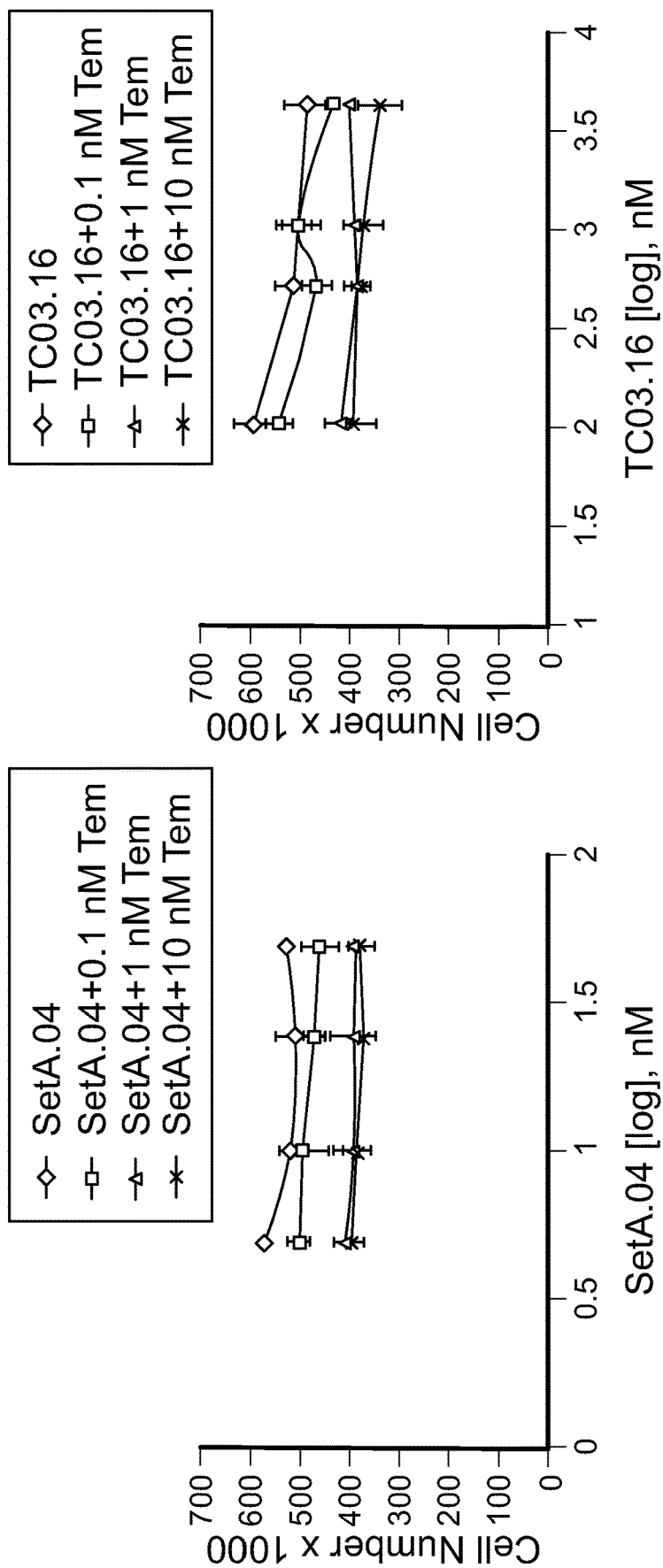
FIG. 16 shows synergy between compounds of the disclosure with an mTor inhibitor in kidney cancer cells. Top graph shows dosing with SSI-4 in the presence of 0, 0.1, 1, and 10 nM temsirolimus (Tem). Bottom graph shows dosing with SSI-2 in the presence of 0, 0.1, 1, and 10 nM temsirolimus (Tem).
Figure 17D:
Figure 17E:
Figure 17F:
Figure 17G:
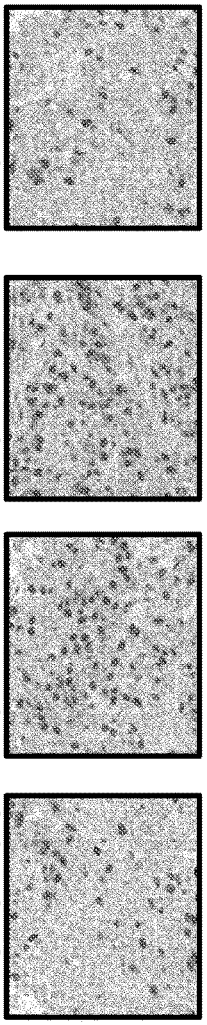

FIG. 16 shows the results of dosing with compounds of the disclosure in combination with known mTor inhibitor temsirolimus. The top graph showed that dosing with different concentrations of SSI-4 (SetA.04) with 0, 0.1, 1, and 10 nM temsirolimus reduced kidney cancer cell proliferation. At 1 and 10 nM temsirolimus, a significantly lower level of kidney cancer cells was observed. Similarly, the bottom graph showed that dosing with different concentrations of SSI-2 (TC03.16) with 0, 0.1, 1, and 10 nM temsirolimus reduced kidney cancer cell proliferation. At 1 and 10 nM temsirolimus, a statistically significant lower level of kidney cancer cells was observed.

Example 12— SCD1 Inhibitor in Combination with Proteasome Inhibitor in an In Vivo Model SCD1 inhibition in vivo using MF-438 fails to demonstrate tumor response as a monotherapy, yet effectively leads to decreased tumor growth when combined with carfilzomib (FIG. 17). MF-438 was tested in combination with carfilzomib in vivo in a THJ16T xenograft model. This cell line harbors mutations in TP53, RB, and PI3KCA, and also demonstrates elevated expression of survivin, a negative regulator of apoptosis that inhibits caspase activation (Marlow L A, D'Innocenzi J, Zhang Y, Rohl S D, Cooper S J, Sebo T, Grant C, McIver B, Kasperbauer J L, Wadsworth J T, Casler J D, Kennedy P W, Highsmith W E, Clark O, Milosevic D, Netzel B, Cradic K, Arora S, Beaudry C, Grebe S K, Silverberg M L, Azorsa D O, Smallridge R C, Copland JA. Detailed molecular fingerprinting of four new anaplastic thyroid carcinoma cell lines and their use for verification of RhoB as a molecular therapeutic target. J Clin Endocrinol Metab. 2010; 95(12):5338-47). A depiction of the treatment map is shown in FIG. 17A. Dehydration and acute inflammation characterized by redness and mild swelling at the tumor site was observed at days 4-5, and 11-12 in both the carfilzomib and combination groups. Saline was administered as necessary. These adverse events resolved 24-48 hours after the second administration of carfilzomib. Discharge from the eye and squinting was seen in groups treated with MF-438 by day 12 of the protocol. However, no other significant adverse events were observed. A regression in mean tumor volume was observed in the combination group beginning day 6, and continued until day 12 where tumor volume began to increase. Tumor growth appeared to temporarily plateau in the carfilzomib group by day 8, after which tumor growth continued (FIG. 17A). A 21% (p=0.32) and 43% (p=0.03) reduction in mean tumor burden as compared to the placebo control was observed in the carfilzomib and combination groups, respectively (FIG. 17A). At the dose tested, no tumor response with MF-438 monotherapy was observed. IHC analysis of tumors resected from each treatment group was performed. H&E stains are provided in FIG. 17B. Results revealed a trend of decreased ki67 staining in both carfilzomib and combination groups (FIG. 17C) and increased cleaved caspase-3 in all treatment groups as compared to placebo control (FIG. 17D), however, only the combination group achieved statistical significance. A trend toward decreased CD31, indicative of decreased tumor vascularization, was observed in both monotherapeutic and combination groups (FIG. 17E). Increased HER-PUD1, a marker for ER stress, was observed in all treatment groups as compared to placebo control (FIG. 17F); with statistically significant combinatorial values. Both MF-438 and carfilzomib induced survivin expression as single agents. Combinatorial therapy did not result in any significant changes in expression (FIG. 17G).

Figure 18A:
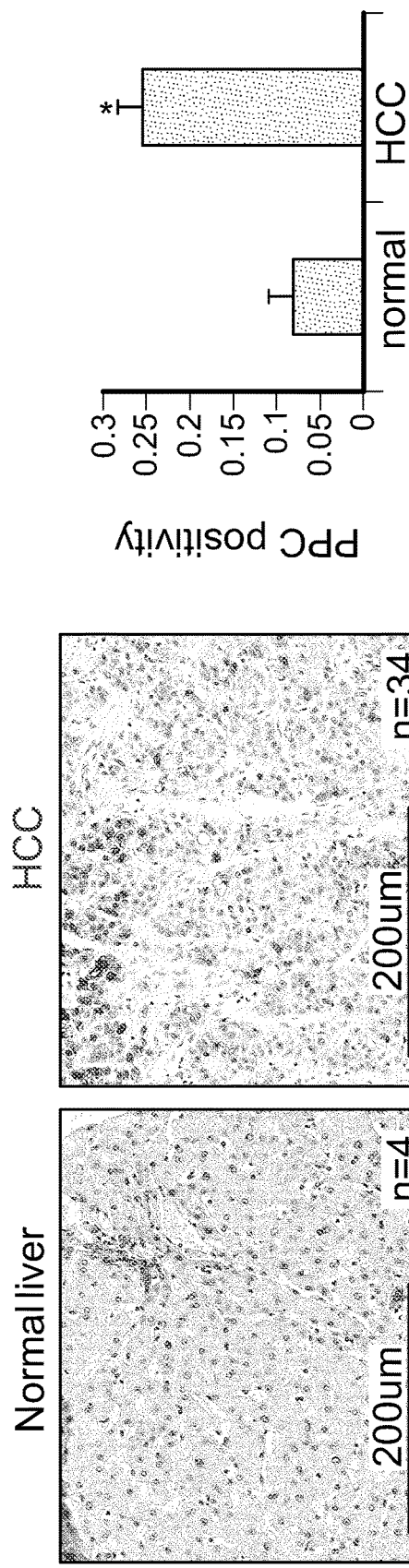
FIGS. 18A-18B illustrate the overexpression of SCD1 in hepatobiliary carcinoma (HCC) patient tissues and cell lines.
Figure 18B:
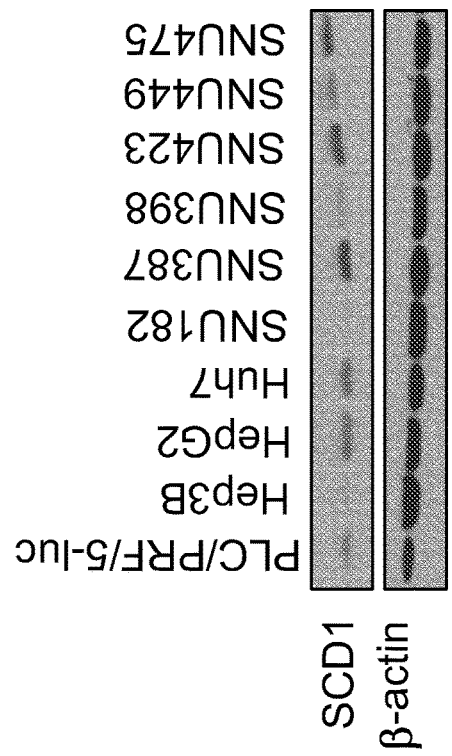

Example 13— Overexpression of SCD1 in HCC Cells and Synergy Observed with Combinations of an SCD1 Inhibitor and a Serine:Threonine:Tyrosine Kinase Inhibitor As shown in FIG. 18, stearoyl CoA desaturase 1 (SCD1) protein is overexpressed in hepatobiliary carcinoma (HCC) patient tissue and cell lines.

Figure 19:
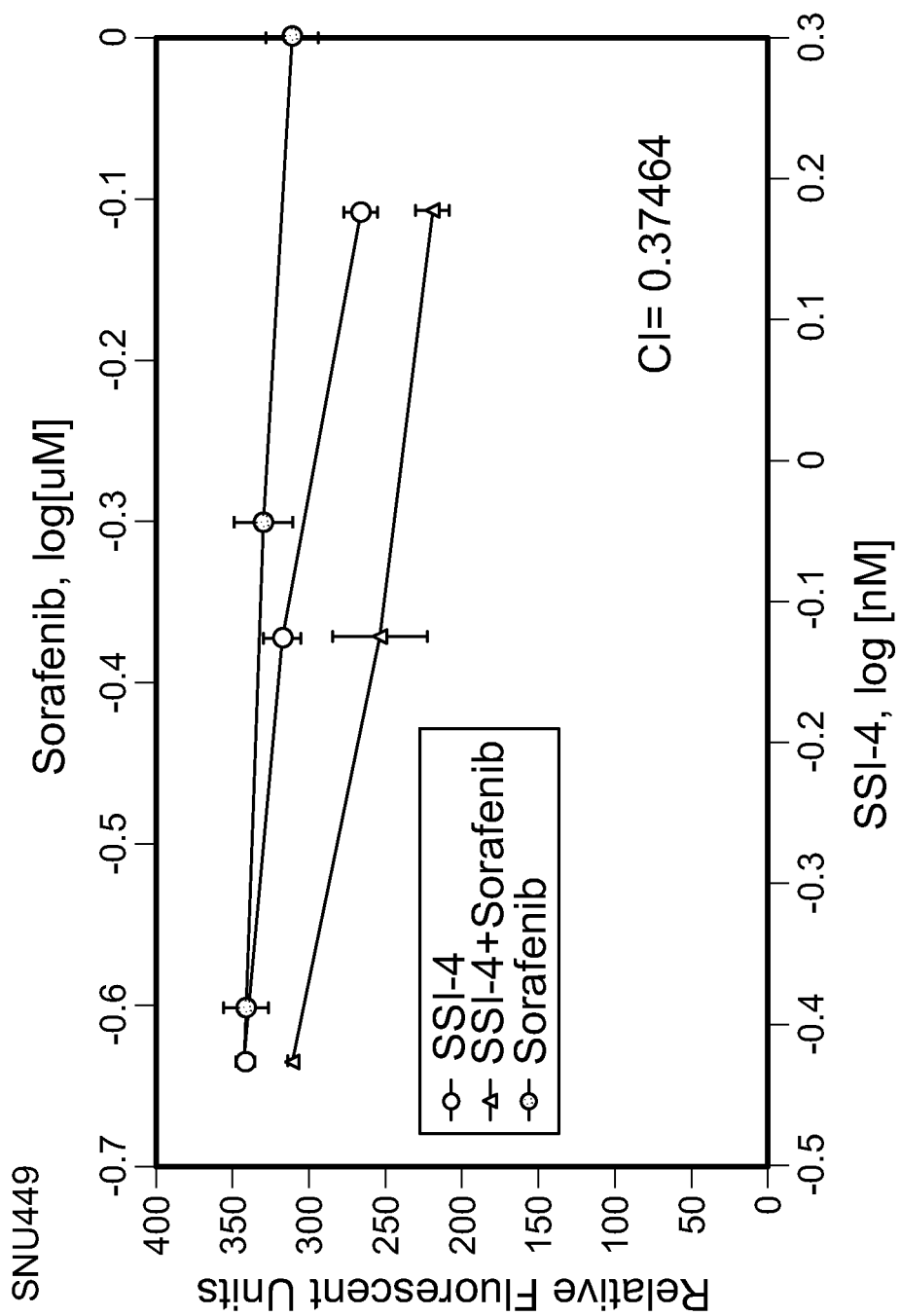
FIG. 19 demonstrates the observed synergy between SSI-4 with sorafenib in an HCC cell line.

SNU449 HCC cells were plated at 20,000 cells/well in 12-well plates. The next day, cells were treated with SSI-4, sorafenib or sorafenib plus SSI-4 at the indicated doses. The doses were chosen by first determining the $IC_{50}$ (dose at which 50% of cell proliferation is inhibited) concentrations for SSI-4 ($IC_{50}$=3.2 nM) and sorafenib ($IC_{50}$=2.0 μM). Using fixed ratios and dosing down from the $IC_{50}$ concentrations stepwise (25%, 12.5%, and 6.25%) was performed for each compound alone or in combination. On day 5, cells were frozen, DNA isolated and quantitated by immunofluorescence (Hoechst reagent) in a spectrophotometer. Cellular DNA is directly proportional to cell number and is commonly used as a measure of cell number. All doses are in replicates of three with the mean+/−standard deviation determined. Using the method of Chou and Talalay, combination index (CI) was used to determine whether these two compounds when combined act synergistically (<0.8), additively ((<1.1>0.8), or antagonistically (>1.1). Sorafenib is currently the only clinical standard of care for metastatic HCC. As seen in FIG. 19, combination SSI-4 plus sorafenib is synergistic in inhibiting SNU449 cell proliferation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims

What is claimed is:

1. A compound according to Formula (I):

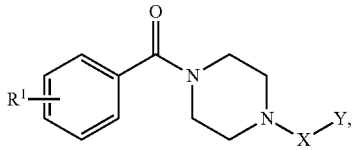

(I)

or a pharmaceutically acceptable salt thereof, wherein:

$R^1$ is an unsubstituted $C_{1-6}$alkyl or $C_{1-6}$haloalkyl;
X is

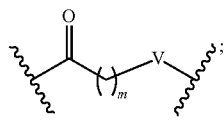

Y is selected from the group consisting of:

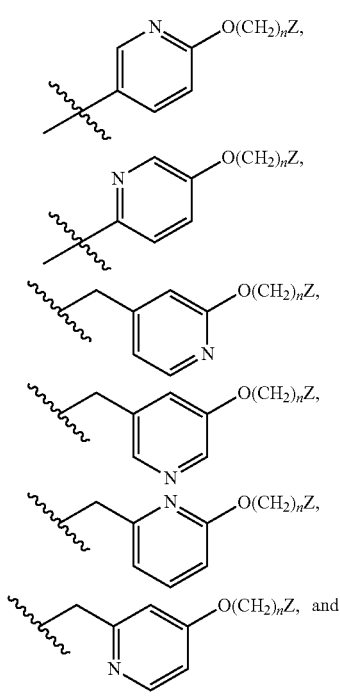

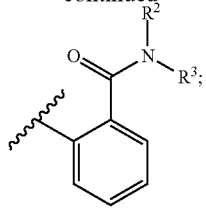

m is 0 or 1;
n is 0, 1, or 2;
V is $NR^4$ or O;
$R^2$, $R^3$, and $R^4$ are each independently H or an unsubstituted $C_{1-6}$alkyl; and
Z is an unsubstituted aryl.

2. The compound of claim 1, wherein the compound according to Formula (I) has the structure of Formula (Ia):

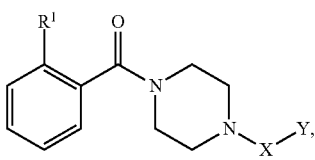

(Ia)

or a pharmaceutically acceptable salt thereof.

3. The compound of claim 1, wherein $R^1$ is $CF_3$.
4. The compound of claim 1, wherein m is 0.
5. The compound of claim 1, wherein V is NH.
6. The compound of claim 1, wherein Y is

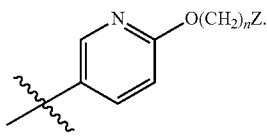

7. The compound of claim 1, wherein Y is

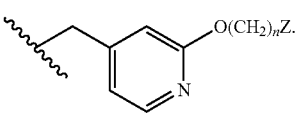

8. The compound of claim 1, wherein m is 1.
9. The compound of claim 1, wherein V is O.

10. The compound of claim 9, wherein Y is

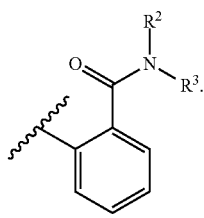

11. The compound of claim 1, wherein $R^2$ is H; and $R^3$ is $CH_3$.

12. The compound of claim 11, wherein Y is

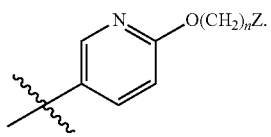

13. The compound of claim 1, wherein n is 1.

14. The compound of claim 1, wherein Z is phenyl.

15. The compound of claim 1, wherein the compound according to Formula (I) is selected from the group consisting of:

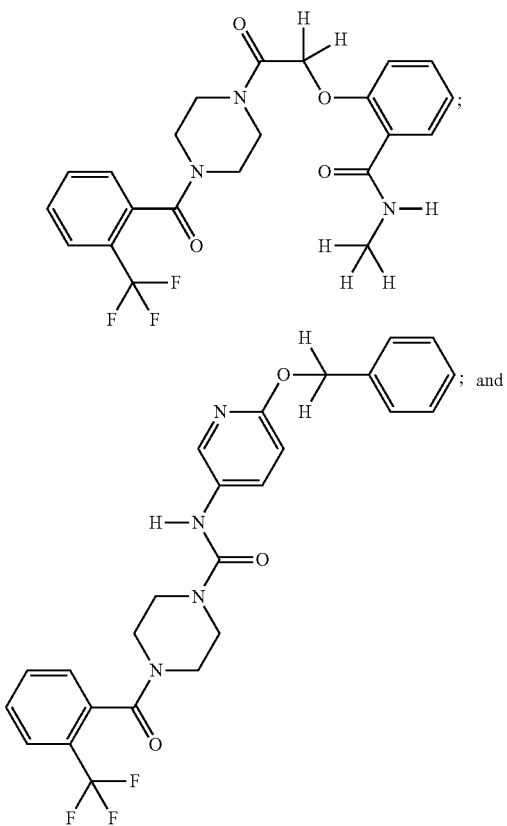

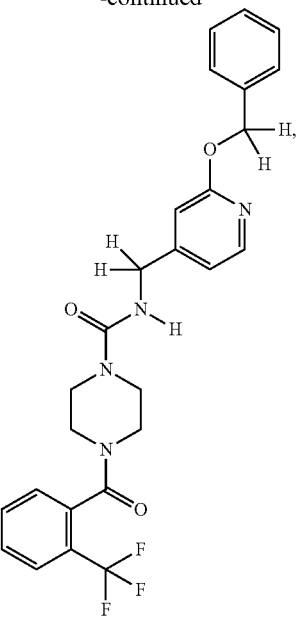

or a pharmaceutically acceptable salt thereof.

16. A pharmaceutical composition comprising a compound, or a pharmaceutically acceptable salt thereof, according to claim 1, and a pharmaceutically acceptable carrier.

17. A method for inhibiting SCD1 in a cancer cell, the method comprising contacting the cancer cell with an effective amount of a compound, or a pharmaceutically acceptable salt thereof, according to claim 1.

18. The method of claim 17, wherein the cancer cell is selected from a kidney cancer cell, a liver cancer cell, a breast cancer cell, a lung cancer cell, a pancreatic cancer cell, a bladder cancer cell, a colon cancer cell, a melanoma cell, a thyroid cancer cell, an ovarian cancer cell, and a prostate cancer cell.

19. A method for treating a cancer in a subject in need thereof, the method comprising administering to the subject a therapeutically effective amount of a compound, or a pharmaceutically acceptable salt thereof, according to claim 1.

20. The method of claim 19, wherein the cancer is selected from a kidney cancer, a liver cancer, a breast cancer, a lung cancer, a pancreatic cancer, a bladder cancer, a colon cancer, a melanoma, a thyroid cancer, an ovarian cancer, and a prostate cancer.

* * * * *

UNITED STATES PATENT AND TRADEMARK OFFICE
CERTIFICATE OF CORRECTION

| | | |
|---|---|---|
| PATENT NO. | : 12,286,413 B2 | Page 1 of 1 |
| APPLICATION NO. | : 17/713949 | |
| DATED | : April 29, 2025 | |
| INVENTOR(S) | : John A. Copland, III et al. | |

It is certified that error appears in the above-identified patent and that said Letters Patent is hereby corrected as shown below:

In the Claims

In Column 50, Line 47 (Approx.), In Claim 5, delete "Vis" and insert -- V is --.

In Column 50, Line 67 (Approx.), In Claim 9, delete "Vis" and insert -- V is --.

Signed and Sealed this
Twenty-first Day of October, 2025

John A. Squires
*Director of the United States Patent and Trademark Office*